(12) United States Patent
Tohata et al.

(10) Patent No.: US 9,650,623 B2
(45) Date of Patent: May 16, 2017

(54) IMPROVING THE SOLUBILITY OF AN ALKALINE PROTEASE IN A LIQUID DETERGENT BY AMINO ACID SUBSTITUTION

(71) Applicant: Kao Corporation, Chou-ku, Tokyo (JP)

(72) Inventors: Masatoshi Tohata, Utsunomiya (JP); Yumi Nishimura, Wakayama (JP); Yasunao Wada, Wakayama (JP); Katsuhisa Saeki, Utsunomiya (JP); Mitsuyoshi Okuda, Utsunomiya (JP)

(73) Assignee: Kao Corporation, Tokyo (JP)

( * ) Notice: Subject to any disclaimer, the term of this patent is extended or adjusted under 35 U.S.C. 154(b) by 250 days.

(21) Appl. No.: 14/383,708

(22) PCT Filed: Apr. 9, 2013

(86) PCT No.: PCT/JP2013/061141
§ 371 (c)(1),
(2) Date: Sep. 8, 2014

(87) PCT Pub. No.: WO2013/154201
PCT Pub. Date: Oct. 17, 2013

(65) Prior Publication Data
US 2015/0056681 A1    Feb. 26, 2015

(30) Foreign Application Priority Data

Apr. 10, 2012  (JP) ................................ 2012-089482
Feb. 21, 2013  (JP) ................................ 2013-031995

(51) Int. Cl.
*C11D 3/386* (2006.01)
*C12N 9/54* (2006.01)

(52) U.S. Cl.
CPC ............ *C12N 9/54* (2013.01); *C11D 3/38618* (2013.01)

(58) Field of Classification Search
None
See application file for complete search history.

(56) References Cited

U.S. PATENT DOCUMENTS

| | | | |
|---|---|---|---|
| 5,286,404 A | 2/1994 | Eriksen et al. | |
| 5,312,561 A | 5/1994 | Hoshino et al. | |
| 5,972,873 A | 10/1999 | Nielsen et al. | |
| 6,376,227 B1 | 4/2002 | Takaiwa et al. | |
| 6,803,222 B2 | 10/2004 | Hatada et al. | |
| 7,368,273 B2 | 5/2008 | Okuda et al. | |
| 7,371,839 B2 | 5/2008 | Hatada et al. | |
| 7,429,642 B2 | 9/2008 | Okuda et al. | |
| 7,473,544 B2 | 1/2009 | Okuda et al. | |
| 7,776,578 B2 | 8/2010 | Okuda et al. | |
| 8,609,811 B2 | 12/2013 | Andersen et al. | |
| 8,648,015 B2 | 2/2014 | Estell et al. | |
| 8,778,650 B2 | 7/2014 | Tohata et al. | |
| 8,883,970 B2 | 11/2014 | Andersen et al. | |
| 9,133,425 B2 | 9/2015 | Cascao-Pereira et al. | |
| 2002/0064854 A1 | 5/2002 | Takaiwa et al. | |
| 2003/0022351 A1 | 1/2003 | Hatada et al. | |
| 2004/0002432 A1 | 1/2004 | Okuda et al. | |
| 2004/0142837 A1 | 7/2004 | Takaiwa et al. | |
| 2004/0203129 A1 | 10/2004 | Hatada et al. | |
| 2005/0214922 A1 | 9/2005 | Okuda et al. | |
| 2006/0078978 A1 | 4/2006 | Okuda et al. | |
| 2007/0015240 A1 | 1/2007 | Svendsen et al. | |
| 2008/0004186 A1 | 1/2008 | Estell et al. | |
| 2008/0177040 A1 | 7/2008 | Okuda et al. | |
| 2008/0318271 A1 | 12/2008 | Nielsen et al. | |
| 2009/0082246 A1 | 3/2009 | Andersen et al. | |
| 2009/0203111 A1 | 8/2009 | Svendsen et al. | |
| 2010/0152092 A1 | 6/2010 | Nielsen et al. | |
| 2010/0216682 A1 | 8/2010 | Cascao-Pereira et al. | |
| 2010/0233780 A1 | 9/2010 | Aehle et al. | |
| 2010/0297727 A1 | 11/2010 | Aehle et al. | |
| 2011/0071068 A1 | 3/2011 | Nielsen et al. | |
| 2011/0082048 A1 | 4/2011 | Estell et al. | |
| 2011/0275136 A1 | 11/2011 | Andersen et al. | |
| 2012/0058928 A1 | 3/2012 | Tohata et al. | |
| 2014/0073553 A1 | 3/2014 | Andersen et al. | |
| 2014/0187440 A1 | 7/2014 | Estell et al. | |

(Continued)

FOREIGN PATENT DOCUMENTS

| | | |
|---|---|---|
| CN | 1446910 A | 10/2003 |
| CN | 1539966 A | 10/2004 |

(Continued)

OTHER PUBLICATIONS

Saeki et al, Novel oxidatively stable subtilisin-like serine proteases from alkaliphilic *Bacillus* spp.: enzymatic properties, sequences, and evolutionary relationships. Biochem. Biophys. Res. Commun. 279 (2), 313-319 (2000).*

NCBI database Acc#BAB21269 from Saeki et al, Biochem. Biophys. Res. Commun. 279 (2), 313-319 (2000). Alignment with SEQ ID No. 2.*

International Search Report (ISR) for PCT/JP2013/061141; I.A. fd: Apr. 9, 2013, mailed Nov. 8, 2013 from the European Patent Office, Rijswijk, Netherlands.

International Preliminary Report on Patentability, Chapter I of the Patent Cooperation Treaty (PCT Rule 44*bis*), including the Written Opinion of the International Searching Authority, for PCT/JP2013/061141; I.A. fd: Apr. 9, 2013, issued Oct. 14, 2014, by the International Bureau of WIPO, Geneva, Switzerland.

(Continued)

*Primary Examiner* — Sheridan Swope
(74) *Attorney, Agent, or Firm* — Sterne, Kessler, Goldstein & Fox P.L.L.C.

(57) ABSTRACT

Providing an alkaline protease exhibiting an improved solubility in a liquid detergent. A mutant alkaline protease consisting of the amino acid sequence represented by SEQ ID No: 2 or an amino acid sequence having 80% or more sequence identity therewith, in which at least one amino acid residue selected from the group consisting of the amino acid residues at predetermined positions of the amino acid sequence represented by SEQ ID No: 2 or corresponding positions thereto are substituted.

11 Claims, No Drawings

(56) References Cited

U.S. PATENT DOCUMENTS

| | | |
|---|---|---|
| 2015/0152361 A1 | 6/2015 | Andersen et al. |
| 2016/0032267 A1 | 2/2016 | Cascao-Pereira et al. |

FOREIGN PATENT DOCUMENTS

| | | |
|---|---|---|
| CN | 1757721 A | 4/2006 |
| CN | 101532000 A | 9/2009 |
| CN | 101560509 A | 10/2009 |
| CN | 101778940 A | 7/2010 |
| EP | 1 347 044 A2 | 9/2003 |
| EP | 1 466 962 A1 | 10/2004 |
| EP | 1 645 632 A2 | 4/2006 |
| EP | 2 204 450 A1 | 7/2010 |
| JP | 05-500977 A | 2/1993 |
| JP | 11-507680 A | 7/1999 |
| JP | 2000-506933 A | 6/2000 |
| JP | 2002-218989 A | 8/2002 |
| JP | 2004-000122 A | 1/2004 |
| JP | 2004-505606 A | 2/2004 |
| JP | 2006-521795 A | 9/2006 |
| JP | 2009-034062 A | 2/2009 |
| JP | 2009-034063 A | 2/2009 |
| JP | 2010-529842 A | 9/2010 |
| JP | 2010-273672 A | 12/2010 |
| JP | 2010-273673 A | 12/2010 |
| WO | WO 96/41859 A1 | 12/1996 |
| WO | WO 98/13462 A1 | 4/1998 |
| WO | WO 99/18218 A1 | 4/1999 |
| WO | WO 01/66712 A1 | 9/2001 |
| WO | WO 01/66712 A2 | 9/2001 |
| WO | WO 2004/083362 A2 | 9/2004 |
| WO | WO 2006/032277 | 3/2006 |
| WO | WO 2008/153925 A2 | 12/2008 |
| WO | WO 2008/153925 A9 | 12/2008 |
| WO | WO 2008/153934 A2 | 12/2008 |
| WO | WO 2010/126156 A2 | 11/2010 |
| WO | WO 2011/036264 A1 | 3/2011 |

OTHER PUBLICATIONS

Saeki, K et al., "Novel oxidatively stable subtilisin-like serine proteases from alkaliphilic *Bacillus* spp.: enzymatic properties, sequences, and evolutionary relationships," Biochem Biophys Res Commun, Dec. 2000; 279(2): 313-319, Academic Press, San Diego, CA.

Ohta, M et al., "A dextran-protease conjugate for cosmetic use," Cosmetics & Toiletries magazine, Jun. 1996; 111:79-88, Allured Publishing Corporation, Carol Stream, IL.

* cited by examiner

IMPROVING THE SOLUBILITY OF AN ALKALINE PROTEASE IN A LIQUID DETERGENT BY AMINO ACID SUBSTITUTION

The content of the electronically submitted substitute sequence listing, file name 2537_1020002_SequenceListing_ST25.txt, size 68,479 bytes; and date of creation Sep. 2, 2014, filed herewith, is incorporated herein by reference in its entirety.

FIELD OF THE INVENTION

The present invention relates to a method for improving solubility of an alkaline protease in a liquid detergent.

BACKGROUND OF THE INVENTION

Protease has for a long time been used in the industrial field and applied to an extremely wide variety of products such as detergents including fabric detergents, fiber-reforming agents, leather treatment agents, cosmetics, bath salts, food reforming agents and medicinal products. Among them, the protease for detergent use is industrially produced in the largest amount. For example, Alcalase, Savinase (registered trade mark; Novozymes), Maxacal (registered trade mark; Genencor), BLAP (registered trade mark; Henkel) and KAP (Kao Corp.) are generally known.

A purpose for adding a protease to a detergent is to decompose stain mainly constituted of proteins attached to a clothing material into low-molecular substances, thereby accelerating solubilization with a surfactant. However, stain is actually a composite which contains not only proteins but also a plurality of components including organic substances and inorganic substances (such as lipids derived from sebum and solid particles) in combination. Then, alkaline proteases of about 43,000 in molecular weight exhibiting excellent washing performance against composite stain (i.e. containing not only protein but also sebum and others) have been developed and patent applicated (see Patent Document 1). The alkaline proteases differ from subtilisin, which is a conventionally known serine protease derived from a *Bacillus* genus bacteria, having different molecular weight, primary structure and enzymatic properties, and particularly differ from subtilisin in that the alkaline proteases have extremely strong oxidant resistance. Accordingly, it has been proposed that the alkaline proteases are classified into a new subfamily of subtilisin (Non Patent Document 1).

Detergents can be classified into both a powder detergent and a liquid detergent based on their forms. The liquid detergent has excellent solubility compared to the powder detergent. The liquid detergent has a merit since an undiluted liquid detergent can be directly applied to stains. Also recently, a liquid detergent (so called, a concentrated liquid detergent), which functions equivalently to a conventional liquid detergent by using a half amount, has been commercially available. Since such a concentrated liquid detergent is contained in a small container, it does not require a large storage space or a large amount of fuel for transportation. In addition to these advantages, based on thorough reconsideration of washing mechanism, some products show improved rinsing performance. In this manner, time required for laundry can be reduced and water required can be saved.

In order to constantly maintain a predetermined enzymatic activity of an enzyme-containing liquid detergent, it is necessary to stabilize the enzyme such as a protease dissolved in the liquid detergent. Furthermore, to enhance the detergency of a detergent, it is desirable to add an enzyme to the detergent as much as possible. However, it is widely known that it is technically difficult to stably mix an enzyme with a liquid detergent. For example, storing an enzyme in a liquid at normal temperature easily cause denaturation of a protein. In addition, a surfactant, a fatty acid, a solvent and others are contained in a liquid detergent and the pH thereof is weak alkali. Thus, the liquid detergent is extremely severe environmental conditions for an enzyme. Furthermore, a protease is a proteolytic enzyme. Because of the feature, protease suffers from autodigestion, which makes it further difficult to stably store the protease in a liquid detergent. Moreover, low water content of the concentrated liquid detergent (concentrated compared to a conventional liquid detergent) makes it difficult to dissolve a large amount of enzyme.

As a technique for stably maintaining enzymatic activity in a liquid detergent, it is known to add an enzyme stabilizer such as a calcium ion, borax, boric acid, a boron compound, a carboxylic acid such as formic acid, and a polyol. Furthermore, overcoming autodigestion by inhibiting protease activity has been studied. Methods of stabilizing a protease by reversible inhibition of the protease by 4-substituted phenyl boronic acid (Patent Document 2) and by a certain peptide aldehyde and a boron composition (Patent Document 3) have been reported. Moreover, it is reported that a protease chemically modified with dextran can be improved in stability in an aqueous solution containing a surfactant (Non Patent Document 2). In addition, a protease mutant improved in stability to a surfactant is also known (Patent Documents 4 to 6).

In contrast, a technique for improving solubility of an enzyme to a liquid detergent has not yet been developed up to the present.

CITATION LIST

Patent Documents

[Patent Document 1] WO 99/18218 A
[Patent Document 2] JP-A-11-507680
[Patent Document 3] JP-A-2000-506933
[Patent Document 4] JP-A-2009-034062
[Patent Document 5] JP-A-2009-034063
[Patent Document 6] WO 2010/126156 A Non Patent Document

[Non-Patent Document 1] Saeki et al., Biochem. Biophys. Res. Commun., 279, 313-319, 2000.
[Non-Patent Document 2] Cosmetics & Toiletries magazine, 111, p 79-88, 1996.

SUMMARY OF THE INVENTION

More specifically, in one embodiment, the present invention provides a method of improving solubility of an alkaline protease in a liquid detergent, the method comprising, in an alkaline protease consisting of the amino acid sequence represented by SEQ ID No: 2 or an amino acid sequence having 80% or more identity therewith, substituting at least one amino acid residue selected from the group consisting of the amino acid residues at positions described in column (i) of Tables 1-1 and 1-2 of the amino acid sequence represented by SEQ ID No: 2 or the positions corresponding thereto, with an amino acid residue described in column (ii) of Tables 1-1 and 1-2.

TABLE 1-1

| | (i) Position | (ii) Amino acid residue |
|---|---|---|
| (A) | 405 | leucine, tryptophan, phenylalanine, isoleucine, proline or valine |
| (B) | 81 | leucine, proline, tyrosine, tryptophan, phenylalanine, isoleucine or glutamine |
| (C) | 40 | isoleucine, phenylalanine, leucine, valine or tryptophan |
| (D) | 191 | leucine, valine, phenylalanine, isoleucine or tryptophan |
| (E) | 59 | valine, isoleucine, leucine, phenylalanine, methionine or tryptophan |
| (F) | 11 | glycine, asparagine or serine |
| (G) | 16 | isoleucine, leucine, valine or tryptophan |
| (H) | 20 | alanine |
| (I) | 22 | tryptophan |
| (J) | 23 | asparagine |
| (K) | 37 | threonine |
| (L) | 41 | isoleucine |
| (M) | 52 | glycine or serine |
| (N) | 53 | alanine, isoleucine or valine |
| (O) | 56 | valine |
| (P) | 60 | phenylalanine, isoleucine, leucine, valine or tryptophan |
| (Q) | 63 | aspartic acid or leucine |
| (R) | 80 | alanine or histidine |
| (S) | 82 | glutamine |
| (T) | 91 | cysteine |
| (U) | 100 | phenylalanine, isoleucine, leucine or tryptophan |
| (V) | 101 | phenylalanine, isoleucine, leucine, valine, tryptophan or tyrosine |
| (W) | 109 | phenylalanine, isoleucine or leucine |
| (X) | 113 | leucine or tryptophan |
| (Y) | 120 | phenylalanine, isoleucine, tryptophan or tyrosine |
| (Z) | 135 | leucine |
| (AA) | 140 | phenylalanine, leucine or tryptophan |
| (AB) | 151 | phenylalanine |
| (AC) | 166 | phenylalanine, isoleucine, leucine, valine or tryptophan |
| (AD) | 194 | tyrosine |
| (AE) | 200 | tryptophan |
| (AF) | 204 | isoleucine, leucine, valine or methionine |
| (AG) | 212 | leucine, valine or tryptophan |

TABLE 1-2

| | (i) Position | (ii) Amino acid residue |
|---|---|---|
| (AH) | 233 | isoleucine, leucine or tryptophan |
| (AI) | 238 | leucine |
| (AJ) | 243 | isoleucine, leucine or tyrosine |
| (AK) | 246 | phenylalanine, leucine, valine, tryptophan or tyrosine |
| (AL) | 275 | phenylalanine, leucine or tryptophan |
| (AM) | 277 | phenylalanine, isoleucine, leucine or valine |
| (AN) | 297 | phenylalanine, leucine or tryptophan |
| (AO) | 326 | tryptophan |
| (AP) | 330 | phenylalanine, methionine or tryptophan |
| (AQ) | 332 | glycine, threonine, or valine |
| (AR) | 334 | leucine |
| (AS) | 342 | glutamic acid, leucine, threonine or tryptophan |
| (AT) | 343 | threonine |
| (AU) | 357 | leucine |
| (AV) | 359 | phenylalanine, isoleucine, leucine or glycine |
| (AW) | 361 | isoleucine, valine or tryptophan |
| (AX) | 376 | tryptophan |
| (AY) | 378 | leucine or tryptophan |
| (AZ) | 385 | methionine, proline or tyrosine |
| (BA) | 386 | alanine, isoleucine, leucine or methionine |
| (BB) | 387 | phenylalanine, glycine, isoleucine, leucine, methionine, valine or tryptophan |
| (BC) | 390 | phenylalanine, glycine, serine, threonine or tyrosine |
| (BD) | 393 | glutamine |
| (BE) | 396 | glycine |
| (BF) | 403 | lysine or threonine |
| (BG) | 406 | phenylalanine, valine or tryptophan |
| (BH) | 407 | cysteine or glycine |
| (BI) | 408 | isoleucine, asparagine, tryptophan or tyrosine |
| (BJ) | 409 | tryptophan or tyrosine |
| (BK) | 411 | alanine, leucine, proline or valine |
| (BL) | 427 | valine |
| (BM) | 433 | leucine |

In another embodiment, the present invention provides a mutant alkaline protease consisting of the amino acid sequence represented by SEQ ID No: 2 or an amino acid sequence having 80% or more identity therewith, in which at least one amino acid residue selected from the group consisting of the amino acid residues at positions described in column (i) of Tables 2-1 and 2-2 of the amino acid sequence represented by SEQ ID No: 2 or the positions corresponding thereto is an amino acid residue described in column (ii) of Tables 2-1 and 2-2.

TABLE 2-1

| | (i) Position | (ii) Amino acid residue |
|---|---|---|
| (A') | 405 | leucine, tryptophan, phenylalanine, isoleucine, proline or valine |
| (B') | 81 | leucine, proline, tyrosine, tryptophan, phenylalanine, isoleucine or glutamine |
| (C') | 40 | isoleucine, phenylalanine, leucine, valine or tryptophan |
| (D') | 191 | leucine, valine, phenylalanine, isoleucine or tryptophan |
| (E') | 59 | valine, isoleucine, leucine, phenylalanine, methionine or tryptophan |
| (F') | 11 | glycine, asparagine or serine |
| (G') | 16 | leucine or tryptophan |
| (H') | 20 | alanine |
| (I') | 22 | tryptophan |
| (J') | 23 | asparagine |
| (K') | 37 | threonine |
| (L') | 41 | isoleucine |
| (M') | 52 | glycine or serine |
| (N') | 53 | alanine, isoleucine or valine |
| (O') | 56 | valine |
| (P') | 60 | phenylalanine, isoleucine, leucine, valine or tryptophan |
| (Q') | 63 | aspartic acid or leucine |
| (R') | 80 | alanine or histidine |
| (S') | 91 | cysteine |
| (T') | 100 | phenylalanine, isoleucine, leucine or tryptophan |
| (U') | 109 | phenylalanine, isoleucine or leucine |
| (V') | 113 | leucine or tryptophan |
| (W') | 120 | phenylalanine, isoleucine, tryptophan or tyrosine |
| (X') | 135 | leucine |
| (Y') | 140 | phenylalanine, leucine or tryptophan |
| (Z') | 151 | phenylalanine |
| (AA') | 166 | phenylalanine, isoleucine, leucine, valine or tryptophan |
| (AB') | 200 | tryptophan |
| (AC') | 204 | leucine or methionine |
| (AD') | 212 | leucine, valine or tryptophan |
| (AE') | 233 | isoleucine, leucine or tryptophan |
| (AF') | 238 | leucine |
| (AG') | 243 | isoleucine, leucine or tyrosine |

TABLE 2-2

| | (i) Position | (ii) Amino acid residue |
|---|---|---|
| (AH') | 246 | phenylalanine, leucine, valine, tryptophan or tyrosine |
| (AI') | 275 | phenylalanine, leucine or tryptophan |
| (AJ') | 277 | phenylalanine, isoleucine, leucine or valine |
| (AK') | 297 | phenylalanine, leucine or tryptophan |
| (AL') | 326 | tryptophan |

TABLE 2-2-continued

| | (i) Position | (ii) Amino acid residue |
|---|---|---|
| (AM') | 330 | phenylalanine, methionine or tryptophan |
| (AN') | 332 | glycine, threonine, or valine |
| (AO') | 334 | leucine |
| (AP') | 343 | threonine |
| (AQ') | 357 | leucine |
| (AR') | 359 | phenylalanine or glycine |
| (AS') | 361 | isoleucine, valine or tryptophan |
| (AT') | 376 | tryptophan |
| (AU') | 378 | leucine or tryptophan |
| (AV') | 385 | methionine, proline or tyrosine |
| (AW') | 386 | alanine, isoleucine, leucine or methionine |
| (AX') | 387 | phenylalanine, glycine, isoleucine, leucine, methionine, valine or tryptophan |
| (AY') | 390 | phenylalanine, glycine, serine, threonine or tyrosine |
| (AZ') | 393 | glutamine |
| (BA') | 396 | glycine |
| (BB') | 403 | lysine or threonine |
| (BC') | 406 | phenylalanine, valine or tryptophan |
| (BD') | 407 | cysteine or glycine |
| (BE') | 408 | isoleucine, asparagine, tryptophan or tyrosine |
| (BF') | 409 | tryptophan or tyrosine |
| (BG') | 411 | alanine, leucine, proline or valine |
| (BH') | 427 | valine |
| (BI') | 433 | leucine |

In another embodiment, the present invention provides a gene encoding the mutant alkaline protease.

In another embodiment, the present invention provides a recombinant vector comprising the gene.

In another embodiment, the present invention provides a transformant comprising the recombinant vector.

In another embodiment, the present invention provides a method for producing a mutant alkaline protease by using the transformant.

In another embodiment, the present invention provides a liquid detergent composition comprising the mutant alkaline protease.

DETAILED DESCRIPTION OF THE INVENTION

In the specification, the "amino acid residue" refers to any of 20 amino acid residues constituting a protein including alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

In the specification, the "identity (of amino acid sequences)" refers to the ratio (%) of the number of positions at which the same amino acid residue is present in two amino acid sequences relative to the number of full-length amino acid residues when the two amino acid sequences are aligned so as to obtain the largest identity. More specifically, the ratio can be calculated in accordance with the Lipman-Pearson method (Science, 227, 1435, (1985)) and computationally obtained through a homology analysis (Search homology) program of gene information processing software, Genetyx-Win (Ver. 5.1.1; Software Development) by setting the Unit size to compare (ktup) at 2.

The present invention relates to providing a method for improving solubility of an alkaline protease in a liquid detergent and a mutant alkaline protease exhibiting an improved solubility in a liquid detergent. The present invention also relates to providing a liquid detergent composition comprising the alkaline protease mutant.

The present inventors found that the solubility in a liquid detergent of alkaline protease KP43 having a molecular weight of about 43,000 is improved by substituting a predetermined amino acid residue with another amino acid residue.

According to the present invention, it is possible to provide an alkaline protease easily soluble in a liquid detergent. The alkaline protease mutant of the present invention has an improved solubility in a liquid detergent, particularly, in a concentrated liquid detergent and can be added in a larger amount to these detergents. Accordingly, a liquid detergent comprising the alkaline protease of the present invention has higher enzymatic activity compared to a conventional liquid detergent and can exhibit high detergency.

The present invention provides a method for improving the solubility of an alkaline protease. The alkaline protease to be desired by the method of the present invention is an alkaline protease consisting of the amino acid sequence represented by SEQ ID No: 2 or an amino acid sequence having 80% or more identity therewith. In the specification, these are each sometimes referred to as a "parent alkaline protease". In other words, in the specification, the "parent alkaline protease" is an alkaline protease to be modified into a mutant alkaline protease exhibiting an improved solubility by providing a predetermined mutation to the amino acid residue thereof.

As the parent alkaline protease consisting of the amino acid sequence represented by SEQ ID No: 2, for example, an alkaline protease derived from KP43 [*Bacillus* sp. KSM-KP43 (FERM BP-6532)] can be mentioned (International Publication No. WO99/18218 A).

As the parent alkaline protease consisting of an amino acid sequence having an identity of 80% or more with the amino acid sequence represented by SEQ ID No: 2, an alkaline protease having an amino acid sequence, which differs from the amino acid sequence represented by SEQ ID No: 2 but has a sequence identity of 80% or more, preferably, 85% or more, more preferably, 90% or more, further preferably 95% or more, further more preferably, 97% or more, still preferably, 97.5% or more, still more preferably, 98% or more and still further preferably, 99% or more, with the amino acid sequence represented by SEQ ID No: 2; and an alkaline protease prepared by deletion, substitution or insertion of one to several amino acids in the amino acid sequence represented by SEQ ID No: 2, are mentioned. In the specification, the term "one to several" refers to a number of 1 to 40, preferably, 1 to 20, and more preferably, 1 to 10.

Examples of the parent alkaline protease consisting of an amino acid sequence having an identity of 80% or more with the amino acid sequence represented by SEQ ID No: 2 include protease KP9860 [derived from *Bacillus* sp. KSM-KP9860 (FERM BP-6534), WO99/18218, GenBank accession no. AB046403]; protease E-1 [derived from *Bacillus* No. D-6 (FERM P-1592), JP-A-49-71191, GenBank accession no. AB046402]; protease Ya [derived from *Bacillus* sp. Y (FERM BP-1029), JP-A-61-280268, GenBank accession no. AB046404]; protease SD521 [derived from *Bacillus* SD521 (FERM P-11162), JP-A-3-191781, GenBank accession no. AB046405]; protease A-1 [derived from NCIB12289, WO88/01293, GenBank accession no. AB046406]; protease A-[derived from NCIB12513, WO98/56927]; and protease 9865 [derived from *Bacillus* sp. KSM-9865 (FERN P-18566), GenBank accession no. AB084155].

Further Examples of the parent alkaline protease consisting of an amino acid sequence having an identity of 80% or more with the amino acid sequence represented by SEQ ID No: 2 include alkaline protease mutants prepared by introducing at least one of the mutations described in JP-A-2002-218989, JP-A-2002-306176, JP-A-2003-125783, JP-A-2004-000122, JP-A-2004-057195, JP-A-2004-0305175, JP-A-2004-305176, JP-A-2006-129865, JP-A-2008-212084, JP-A-2009-034063, JP-A-2009-034062, JP-A-2010-273672 or JP-A-2010-273673, in the alkaline protease derived from the KP-43 strain.

Preferably, in the parent alkaline protease consisting of an amino acid sequence having an identity of 80% or more with the amino acid sequence represented by SEQ ID No: 2, at least the amino acid residue corresponding to position 30 of the amino acid sequence represented by SEQ ID No: 2 is aspartic acid, the amino acid residue corresponding to position 68 thereof is histidine and the amino acid residue corresponding to position 255 thereof is serine. It is estimated that these amino acid residues are essential amino acids for an alkaline protease (Saeki et al., Journal of bioscience and Bioengineering, 103, 501-508, 2007).

More preferably, in the parent alkaline protease consisting of an amino acid sequence having an identity of 80% or more with the amino acid sequence represented by SEQ ID No: 2, the amino acid residue at the position corresponding to each position described in the following column (i) of Table 3 of the amino acid sequence represented by SEQ ID No: 2 is the amino acid residue described in column (ii) of Table 3. The positions indicated in the following column (i) of Table 3 are positions of the amino acid residues highly conserved between the parent alkaline proteases mentioned above (Saeki et al., Journal of bioscience and Bioengineering, 103, 501-508, 2007) from which the positions of amino acid residues described in the aforementioned patent Documents and amino acid residues of the present invention are excluded.

TABLE 3

|      | (i) Position | (ii) Amino acid |
|------|--------------|-----------------|
| (a)  | 10           | alanine         |
| (b)  | 18           | glycine         |
| (c)  | 21           | glycine         |
| (d)  | 26           | valine          |
| (e)  | 27           | alanine         |
| (f)  | 28           | valine          |
| (g)  | 30           | aspartic acid   |
| (h)  | 32           | glycine         |
| (i)  | 64           | aspartic acid   |
| (j)  | 68           | histidine       |
| (k)  | 69           | glycine         |
| (l)  | 70           | threonine       |
| (m)  | 72           | valine          |
| (n)  | 73           | alanine         |
| (o)  | 74           | glycine         |
| (p)  | 85           | glycine         |
| (q)  | 87           | alanine         |
| (r)  | 88           | proline         |
| (s)  | 92           | leucine         |
| (t)  | 118          | alanine         |
| (u)  | 129          | serine          |
| (v)  | 131          | glycine         |
| (w)  | 145          | valine          |
| (x)  | 159          | alanine         |
| (y)  | 161          | glycine         |
| (z)  | 162          | asparagine      |
| (aa) | 164          | glycine         |
| (ab) | 173          | proline         |
| (ab) | 182          | valine          |

TABLE 3-continued

|      | (i) Position | (ii) Amino acid |
|------|--------------|-----------------|
| (ad) | 183          | glycine         |
| (ae) | 184          | alanine         |
| (af) | 203          | alanine         |
| (ag) | 206          | serine          |
| (ah) | 209          | glycine         |
| (ai) | 223          | proline         |
| (aj) | 224          | glycine         |
| (ak) | 225          | threonine       |
| (al) | 229          | serine          |
| (am) | 248          | tyro sine       |
| (an) | 254          | threonine       |
| (ao) | 255          | serine          |
| (ap) | 258          | threonine       |
| (aq) | 259          | proline         |
| (ar) | 261          | valine          |
| (as) | 262          | alanine         |
| (at) | 263          | glycine         |
| (au) | 266          | alanine         |
| (av) | 289          | leucine         |

Alternatively, an alkaline protease having any one of the following enzymatic properties which the alkaline protease consisting of the amino acid sequence represented by SEQ ID No: 2 has is more preferable as the parent alkaline protease of the present invention. 1) exhibiting oxidant resistance, exhibiting activity in an alkaline condition (pH 8 or more) and being stable. The phrase "exhibiting oxidant resistance" herein means exhibiting at least 50% of residual alkaline protease activity after incubation of the alkaline protease in a 50 mM hydrogen peroxide (containing 5 mM calcium chloride) solution (20 mM Britton-Robinson buffer, pH 10) at 20° C. for 20 minutes (synthetic substrate method). 2) exhibiting 80% or more of residual activity after treatment of the alkaline protease at 50° C., pH 10 for 10 minutes. 3) inhibited by diisopropyl fluorophosphoric acid (DFP) and phenyl methane sulfonyl fluoride (PMSF). 4) having the molecular weight determined by SDS-PAGE of 43,000±2,000.

In the method of the present invention, the solubility of an alkaline protease is improved by substituting the amino acid residue at a target position of the parent alkaline protease with another amino acid residue. To describe more specifically, in the alkaline protease consisting of the amino acid sequence represented by SEQ ID No: 2, at least one of the amino acid residues at the positions described in the following Tables 4-1 to 4-3 are substituted with the amino acid residue after mutation shown in the Tables. Alternatively, in an alkaline protease consisting of an amino acid sequence having an identity of 80% or more with the amino acid sequence represented by SEQ ID No: 2, at least one of the amino acid residues at the positions corresponding to the positions described in the following Tables 4-1 to 4-3 are substituted with the amino acid residue after mutation shown in the Tables. A mutant alkaline protease having a substitution of the above amino acid can be obtained by the method of the present invention. The mutant alkaline protease exhibits alkaline protease activity and improved solubility in a liquid detergent, preferably, a concentrated liquid detergent compared to the parent alkaline protease.

TABLE 4-1

| Position | Amino acid residue in SEQ ID No: 2 | Amino acid residue after mutation |
|---|---|---|
| 405 | asparagine | leucine, tryptophan, phenylalanine, isoleucine, proline or valine |
| 81 | serine | leucine, proline, tyrosine, tryptophan, phenylalanine, isoleucine or glutamine |
| 40 | serine | isoleucine, phenylalanine, leucine, valine or tryptophan |
| 191 | serine | leucine, valine, phenylalanine, isoleucine or tryptophan |
| 59 | threonine | valine, isoleucine, leucine, phenylalanine, methionine or tryptophan |
| 11 | aspartic acid | glycine, asparagine or serine |
| 16 | serine | isoleucine, leucine, valine or tryptophan |
| 20 | tyro sine | alanine |
| 22 | glutamine | tryptophan |
| 23 | glycine | asparagine |
| 37 | arginine | threonine |
| 41 | serine | isoleucine |
| 52 | alanine | glycine or serine |
| 53 | leucine | alanine, isoleucine or valine |
| 56 | leucine | valine |
| 60 | asparagine | phenylalanine, isoleucine, leucine, valine or tryptophan |
| 63 | asparagine | aspartic acid or leucine |
| 80 | glycine | alanine or histidine |
| 82 | threonine | glutamine |
| 91 | asparagine | cysteine |
| 100 | serine | phenylalanine, isoleucine, leucine or tryptophan |
| 101 | glycine | phenylalanine, isoleucine, leucine, valine, tryptophan or tyrosine |
| 109 | serine | phenylalanine, isoleucine or leucine |
| 113 | threonine | leucine or tryptophan |

TABLE 4-2

| Position | Amino acid residue in SEQ ID No: 2 | Amino acid residue after mutation |
|---|---|---|
| 120 | serine | phenylalanine, isoleucine, tryptophan or tyrosine |
| 135 | asparagine | leucine |
| 140 | threonine | phenylalanine, leucine or tryptophan |
| 151 | lysine | phenylalanine |
| 166 | asparagine | phenylalanine, isoleucine, leucine, valine or tryptophan |
| 194 | serine | tyrosine |
| 200 | asparagine | tryptophan |
| 204 | glutamine | isoleucine, leucine, valine or methionine |
| 212 | lysine | leucine, valine or tryptophan |
| 233 | serine | isoleucine, leucine or tryptophan |
| 238 | serine | leucine |
| 243 | asparagine | isoleucine, leucine or tyrosine |
| 246 | serine | phenylalanine, leucine, valine, tryptophan or tyrosine |
| 275 | asparagine | phenylalanine, leucine or tryptophan |
| 277 | glycine | phenylalanine, isoleucine, leucine or valine |
| 297 | glycine | phenylalanine, leucine or tryptophan |
| 326 | serine | tryptophan |
| 330 | serine | phenylalanine, methionine or tryptophan |
| 332 | lysine | glycine, threonine or valine |
| 334 | threonine | leucine |
| 342 | glycine | glutamic acid, leucine, threonine or tryptophan |
| 343 | lysine | threonine |
| 357 | serine | leucine |
| 359 | threonine | phenylalanine, isoleucine, leucine or glycine |

TABLE 4-3

| Position | Amino acid residue in SEQ ID No: 2 | Amino acid residue after mutation |
|---|---|---|
| 361 | serine | isoleucine, valine or tryptophan |
| 376 | asparagine | tryptophan |
| 378 | threonine | leucine or tryptophan |
| 385 | phenylalanine | methionine, proline or tyrosine |
| 386 | threonine | alanine, isoleucine, leucine or methionine |
| 387 | serine | phenylalanine, glycine, isoleucine, leucine, methionine, valine or tryptophan |
| 390 | asparagine | phenylalanine, glycine, serine, threonine or tyrosine |
| 393 | tryptophan | glutamine |
| 396 | arginine | glycine |
| 403 | phenylalanine | lysine or threonine |
| 406 | alanine | phenylalanine, valine or tryptophan |
| 407 | proline | cysteine or glycine |
| 408 | glutamine | isoleucine, asparagine, tryptophan or tyrosine |
| 409 | serine | tryptophan or tyrosine |
| 411 | threonine | alanine, leucine, proline or valine |
| 427 | threonine | valine |
| 433 | valine | leucine |

In the method of the present invention, the position of the amino acid residue to be substituted in the parent alkaline protease preferably includes at least one position selected from position 405, position 81, position 40, position 191 and position 59 of the amino acid sequence represented by SEQ ID No: 2; more preferably includes at least two of the aforementioned positions; and further preferably includes at least three of the aforementioned positions.

Also preferably, the position to be substituted includes at least a combination of position 405 and position 81, position 40 or position 191; and more preferably, includes a combination of position 405 and position 81, and position 40, position 191 or position 59. Still more preferably, all of position 405, position 81, position 40, position 191 and position 59 are substituted.

In the amino acid sequence having an identity of 80% or more with the amino acid sequence represented by SEQ ID No: 2, the position to be substituted preferably includes at least one position selected from the positions corresponding to position 405, position 81, position 40, position 191 and position 59 of SEQ ID No: 2; more preferably, includes at least two of the aforementioned positions; and further preferably includes at least three of the aforementioned positions.

Also preferably, the positions to be substituted includes at least a combination of the position corresponding to position 405 and the position corresponding to any one of position 81, position 191 and position 40; and more preferably, includes a combination of the positions corresponding to position 405 and position 81 and the position corresponding to any one of position 40, position 191 and position 59. Still more preferably, all positions corresponding to position 405, position 81, position 40, position 191 and position 59 are substituted.

In addition to a single substitution, double- or multiple-substitution of position 405, position 81, position 40, position 191 and position 59 or the positions corresponding thereto, amino acid residues at other positions shown in Tables 4-1 to 4-3 or the portions corresponding thereto may be substituted.

The amino acid residue substituted at position 405 or the corresponding position thereto is preferably leucine or tryptophan; leucine, proline, tyrosine or tryptophan is preferable at position 81 or the corresponding position thereto; isoleucine, phenylalanine or leucine is preferable at position 40 or the corresponding position thereto; leucine or valine is preferable at position 191 or the corresponding position thereto; and valine, isoleucine or leucine is preferable at position 59 or the corresponding position thereto.

In the specification, the "amino acid residue at the corresponding position" is identified by comparing a desired amino acid sequence with a reference sequence (the amino acid sequence represented by SEQ ID No: 2) by using known algorithm and alignment of the sequence such that the conserved amino acid residues present in the amino acid sequence of individual alkaline proteases indicates maximum homology. By alignment of the amino acid sequences of alkaline proteases by such a method, even if the amino acid sequences have an insertion and a deletion, the position of the homologous amino acid residue in the sequences of individual alkaline proteases can be determined. Alignment can be manually performed, for example, based on the Lipman-Pearson method mentioned above; however, can be performed by using the Clustal W multiple alignment program (Thompson, J. D. et al., (1994) Nucleic Acids Res. 22, p. 4673-4680) by default. The Clustal W multiple alignment program is available from websites: for example, European Bioinformatics Institute: (EBI) and DNA Data Bank of Japan (DDBJ) managed by the National Institute of Genetics.

The alignment obtained above can be fine-tuned if necessary so as to obtain an optimal alignment by those skilled in the art. Such an optimal alignment is preferably determined in consideration of similarity of amino acid sequences and the frequency of insertion of a gap. The similarity of amino acid sequences refers to as follows. When two amino acid sequences are aligned, the ratio (%) of the number of positions at which the same or analogous amino acid residue is present in both sequences relative to the number of full-length amino acid residues is referred to as the similarity. The analogous amino acid residues refer to amino acid residues of the 20 amino acids constituting a protein having analogous properties to each other in polarity and charge, more specifically, capable of causing conservative substitution. The groups of such analogous amino acid residues, which are well known to those skilled in the art, are, for example, but not limited to, arginine and lysine or glutamine; glutamic acid and aspartic acid or glutamine; serine and threonine or alanine; glutamine and asparagine or arginine; and leucine and isoleucine.

The position of the amino acid residue of a desired amino acid sequence aligned with the position corresponding to an arbitrary position of a reference sequence by the aforementioned alignment is regarded as the "corresponding position" to the arbitrary position. The amino acid residue is referred to as "the amino acid residue at the corresponding position".

More specifically, according to the above method, it is possible to specify the amino acid residues at the corresponding positions of: (a) the amino acid residue (asparagine residue) at position 405, (b) the amino acid residue (serine residue) at position 81, (c) the amino acid residue (serine residue) at position 40, (d) the amino acid residue (serine residue) at position 191 and (e) the amino acid residue (threonine residue) at position 59 for example, in the amino acid sequence represented by SEQ ID No: 2, as (a) asparagine residue at position 405, (b) alanine residue at position 81, (c) serine residue at position 40, (d) serine residue at position 191 and (e) threonine residue at position 59 in protease KP9860.

Specific examples of the amino acid residues at the corresponding positions to (a) position 405, (b) position 81, (c) position 40, (d) position 191, (e) position 59 of the amino acid sequence (SEQ ID No: 2) of protease KP43 and the positions corresponding thereto of the above mentioned protease KP9860, protease 9865, protease E-1, protease Ya, protease SD521, protease A-1 and protease A-2 are shown below (Table 5). The amino acid residues at these positions are highly conserved or conserved as analogous amino acid residues.

TABLE 5

| | Protease | | | | | | | |
|---|---|---|---|---|---|---|---|---|
| Position | KP43 | KP9860 | 9865 | E-1 | Ya | SD521 | A-1 | A-2 |
| (a) | Asn405 | Asn405 | Asn405 | Asn404 | Asn404 | Asn404 | Asn405 | Asn404 |
| (b) | Ser81 | Ala81 | Ser81 | Ala80 | Ala80 | Ala80 | Thr81 | Ala80 |
| (c) | Ser40 | Ser40 | Ser40 | Ser40 | Ser40 | Ser40 | Ser40 | Ser40 |
| (d) | Ser191 | Ser191 | Ser191 | Ser190 | Ser190 | Ser190 | Ser191 | Ser190 |
| (e) | Thr59 | Thr59 | Thr59 | Thr59 | Thr59 | Thr59 | Thr59 | Thr59 |

Furthermore, for example, in a mutant alkaline protease having a single amino acid residue inserted between position 133 and position 134 of the alkaline protease represented by SEQ ID No: 2, as described in the aforementioned JP-A-2006-129865, the positions corresponding the downstream from the position 134 of the sequence of SEQ ID No: 2 are shifted by insertion of one residue.

The "corresponding position" thus identified shows high amino acid sequence identity and three-dimensional position thereof is predicted to be conserved between alkaline protease proteins. Therefore, same mutations of an amino acid residue present in the corresponding positions affect same specific protease functions.

The alkaline protease mutant obtained by the method of the present invention may optionally have, in addition to substitutions of amino acid residues at the positions described in Tables 4-1 to 4-3 or the portions corresponding thereto, a mutation (for example, deletion, substitution, addition, insertion) at another position, as long as an effect of improving solubility in a liquid detergent is not prevented. The mutation may be a naturally occurring mutation or artificially introduced mutation.

In the method of the present invention, as a means for substituting an amino acid residue of an alkaline protease, various techniques for mutagenesis known in the art may be used. For example, within an alkaline protease gene encoding the amino acid sequence of a parent alkaline protease (hereinafter, referred to as a parent alkaline protease gene), a nucleotide sequence encoding an amino acid residue to be substituted is mutated by substitution with a nucleotide sequence encoding a desired amino acid residue introduced by the substitution; and further, a mutant alkaline protease is expressed from the mutant gene to obtain a mutant alkaline protease having the amino acid sequence in which the amino acid residue substituted with a desired amino acid residue.

An introduction of a desired mutation into a parent alkaline protease gene can be performed, for example, by various site-directed mutagenesis methods known to those skilled in the art based on PCR amplification using the parent alkaline protease gene as template DNA and amplification thereof by various types of DNA polymerases. Site-directed mutagenesis may be performed by suitable method such as the inverse PCR method and the annealing method ("Revised 4th Edition, New Gene Engineering Handbook" edited by Muramatsu et al., published by Yodosha, p. 82-88). If necessary, a commercially available site-directed mutagenesis kit such as QuickChange II Site-Directed Mutagenesis Kit, QuickChange Multi Site-Directed Mutagenesis Kit from Stratagene and others may be used.

The site-directed mutagenesis into the parent alkaline protease gene can be performed most generally by use of a mutation primer containing the nucleotide mutation. Such a mutation primer may be designed in such a manner that it can be annealed with a region containing a nucleotide sequence encoding the amino acid residue to be mutated by substitution in the parent alkaline protease gene, and that it contains a nucleotide sequence (codon) encoding the amino acid residue to be introduced by substitution. The nucleotide sequences (codon) encoding the amino acid residue to be mutated by substitution and the amino acid residue to be introduced by substitution can be appropriately recognized and selected by those skilled in the art based on general protocols and others.

In the present invention, SOE (splicing by overlap extension)-PCR (Horton R. M. et al., Gene (1989) 77 (1), p. 61-68) method may be used, in which two mutation primers complementary to each other containing the nucleotide mutation to be introduced are used to amplify DNA fragments of an upstream side and a downstream side of the mutation site separately, which are ligated into one fragment. The procedure to introduce a mutation using the SOE-PCR method is more specifically described in Examples (described later).

A template DNA comprising the parent alkaline protease gene can be prepared from bacteria such as Bacillus sp. KSM-KP43 (FERM BP-6532), Bacillus sp. KSM-KP9860 (FERM BP-6534), Bacillus No. D-6 (FERM P-1592), Bacillus sp. Y (FERM BP-1029), Bacillus SD521 (FERM P-11162) and Bacillus sp. KSM-9865 (FERM P-18566) as mentioned above, or mutants thereof, by extracting genomic DNA in accordance with a conventional method or by extracting RNA and synthesizing cDNA in accordance with reverse transcription. Alternatively, based on the amino acid sequence of the parent alkaline protease, the corresponding nucleotide sequence may be synthesized and used as the template DNA.

A genomic DNA can be prepared from a strain of the genus Bacillus mentioned above by a method, for example, described in Pitcher et al., Lett. Appl. Microbiol., 1989, 8: p. 151-156. The template DNA comprising the parent alkaline protease gene may be prepared by inserting cDNA or DNA fragment comprising a parent alkaline protease gene obtained from genomic DNA into a suitable vector.

A primer can be prepared by a known oligonucleotide synthesis method such as a phosphoroamidite method (Nucleic Acids Research, 17, 7059-7071, 1989). Such synthesis of a primer may be performed by using, for example, a commercially available oligonucleotide synthesizer (e.g., manufactured by ABI). Using a primer set including a mutation primer and the parent alkaline protease gene as a template DNA, the site-directed mutagenesis as mentioned above is performed to obtain a mutant alkaline protease gene having a desired mutation introduced therein. The present invention is also directed to the mutant alkaline protease gene thus obtained. Note that the "mutant alkaline protease gene" of the present invention refers to a nucleotide fragment (including e.g., DNA, mRNA and an artificial nucleic acid) encoding an amino acid sequence of the mutant alkaline protease. The "gene" according to the present invention may contain another nucleotide sequence such as an untranslated region (UTR) in addition to an open reading frame (ORF).

The obtained mutant alkaline protease gene is inserted into a vector and ligated in accordance with a conventional method. In this manner, a recombinant vector can be prepared. The vector to be used in the present invention is not particularly limited and any vector, such as a plasmid, a phage, a phagemid, a cosmid, a virus, a YAC vector and a shuttle vector, may be used. As such a vector, although it is not limited, a vector capable of amplifying in bacteria, for example, in Bacillus genus bacteria, is more preferable, and an expression vector capable of inducing expression of an introduced gene in a Bacillus genus bacterium is further preferable. Among them, a shuttle vector, which is replicable in both Bacillus genus bacteria and another organism, can be more preferably used in producing a mutant alkaline protease by recombinant technology. Examples of the preferable vector include, but not limited to, shuttle vectors such as pHA3040SP64 (described later), plasmid pHSP64R or pASP64 (JP-B-3492935), pHY300PLK (expression vector capable of transforming both Escherichia coli and Bacillus subtilis; Ishikawa, H. and Shibahara, H., Jpn. J. Genet, (1985) 60, p. 235-243) and pAC3 (Moriyama, H. et al., Nucleic Acids Res. (1988) 16, p. 8732); plasmids available for transformation of Bacillus bacteria, such as pUB110 (Gryczan, T. J. et al., J. Bacteriol. (1978) 134, p. 318-329) and pTA10607 (Bron, S. et al., Plasmid, 18 (1987) p. 8-15); and secretion vectors capable of providing a secretion signal to a recombinant protein (Yamane, et. al., "Fusion Protein by Bacillus subtilis Secretion Vector", Starch Science, 34. (1987), p. 163-170). Furthermore, plasmids derived from Escherichia coli (for example, pET22b (+), pBR322, pBR325, pUC118, pUC119, pUC18, pUC19 and pBluescript) may be used.

In order to produce a mutant alkaline protease by recombinant technique, the vector to be used is preferably an expression vector. The expression vector may contain, other than essential elements for expression in a host organism, such as a transcriptional promoter, a terminator and a ribosome-binding site, useful sequences such as a selection marker gene, a cis-element including a polylinker and an enhancer, a poly-A addition signal and a ribosome binding sequence (SD Sequence), if necessary.

A transformant can be prepared by using a recombinant vector comprising a mutant alkaline protease gene. In the present invention, a recombinant vector (specifically, a recombinant expression vector) comprising the mutant alkaline protease gene according to the present invention is introduced in a host cell to prepare a transformant (transformed cell), which is cultured in the conditions for inducing expression of a recombinant protein to produce the mutant alkaline protease.

As a host cell into which a recombinant vector is to be introduced, microorganisms including bacteria such as Escherichia coli and Bacillus subtilis and yeast cells can be used. Other than these, any cells such as insect cells and animal cells (for example, mammalian cells) and plant cells may be used. For example, in the present invention, use of a *Bacillus* genus bacterium such as *Bacillus subtilis* is preferable.

For transformation, for example, a known transformation technique such as a calcium phosphate method, an electroporation method, a lipofection method, a particle gun method and a PEG method may be used. For example, as a transformation method applicable to *Bacillus* bacteria, a competent cell transformation method (Bott. K. F. and Wilson, G. A., J. Bacteriol. (1967) 93, 1925), an electroporation method (Brigidi. P. et al., FEMS Microbiol. Lett. (1990) 55, 135), a protoplast transformation method (Chang, S. and Cohen, S. N., Mol. Gen. Genet., (1979) 168, p. 111-115) and a Tris-PEG method (Takahashi W. et al., J. Bacteriol. (1983) 156, p. 1130-1134) are mentioned.

The transformant for producing a recombination protein can be cultured in accordance with a general method known to those skilled in the art. As a medium for culturing, for example, a transformant using a microorganism such as *Escherichia coli* and a yeast cell as a host, either a natural medium or a synthetic medium may be used as long as the medium contains a carbon source, a nitrogen source, inorganic salts and others which can be utilized by a host microorganism and the transformant can be efficiently cultured in the medium. To the medium, e.g., ampicillin and tetracycline may be added in accordance with the type of a selection marker if used. In culturing a microorganism transformed by an expression vector using an inducible promoter, an inducer as needed may be added to the medium. To describe it more specifically, in culturing e.g., bacteria transformed by an expression vector using a Lac promoter, e.g., isopropyl-1-thio-β-D-galactoside (IPTG) can be added to a medium. In culturing a microorganism transformed by an expression vector using a trp promoter, e.g., indoleacetic acid (IAA) can be added to a medium. Although the culture conditions are not particularly limited, culture is preferably performed in the conditions suitable for a host organism used for transformation. For example, for culturing a *Bacillus subtilis* transformant to produce a recombination protein, for example, an LB medium, 2×YT medium, 2×L-maltose medium, or CSL fermentation medium may be used.

In the method of the present invention, a mutant alkaline protease may be expressed by using cell-free translation system from a mutant alkaline protease gene or a transcription product thereof. The "cell-free translation system" refers to an in vitro transcription translation system or an in vitro translation system, which is prepared by adding reagents such as amino acids required for translation of a protein to a suspension solution obtained by mechanically homogenized host cells. The alkaline protease mutant expressed can be obtained from a culture solution, a homogenized cells or cell-free translation system by a general method for use in protein purification, for example, centrifugation, ammonium sulfate precipitation, gel chromatography, ion exchange chromatography and affinity-chromatography (These methods may be used alone or in an appropriate combination). A solution such as a culture supernatant and a lysate supernatant separated or concentrated by centrifugation and an ultrafiltration filter can be directly used as a crude enzymatic solution. If the expressed mutant alkaline protease is not secreted out of cells, the cells may be homogenized in order to separate and purify a protein.

Manipulations such as preparation of mRNA, preparation of cDNA, PCR, RT-PCR, preparation of a library, ligation into a vector, transformation of cells, determination of DNA base sequence, chemical synthesis of a nucleic acid, determination of amino acid sequence of the N-terminal side of a protein, induction of a mutation and extraction of a protein used in the present invention may be performed in accordance with the methods described in general protocols. As such a protocol, for example, Sambrook et al., Molecular Cloning, A laboratory manual, (2001) 3rd Ed., (Sambrook, J. & Russell, D W. Cold Spring Harbor Laboratory Press) can be mentioned. Specifically, as to gene recombination experiment for *Bacillus subtilis*, for example, a general protocol on gene manipulation for *Bacillus subtilis* such as "7.2 *Bacillus subtilis* system", "Biochemical Experiment Course, Part II, 1. Gene Study Method II", written by Hirofumi Yoshikawa, (1986) Tokyo Kagaku Dojin (Tokyo), p. 150-169 may be referred to.

The alkaline protease mutant thus obtained by the method of the present invention exhibits an improved solubility in a liquid detergent, preferably, a concentrated liquid detergent, compared to the parent alkaline protease. Accordingly, the present invention further provides a mutant alkaline protease prepared by the method of the present invention for improving solubility of an alkaline protease in a liquid detergent, a gene (polynucleotide) encoding the mutant, a vector comprising the gene, a transformant comprising the vector and a method for producing a mutant alkaline protease using the transformant.

Furthermore, the mutant alkaline protease of the present invention exhibits an improved solubility in a liquid detergent compared to the parent alkaline protease. Accordingly, the mutant alkaline protease of the present invention is useful as an enzyme to be added to powder detergents, preferably useful as an enzyme to be added to liquid detergents, and more preferably, useful as an enzyme to be added to concentrated liquid detergents. A liquid detergent comprising the mutant alkaline protease of the present invention can contain a large amount of alkaline protease compared to a conventional liquid detergent, and thus can possess higher protease activity than a conventional one, with the result that higher detergency due to the enzyme can be exhibited. Accordingly, the invention of the present application further provides a liquid detergent composition comprising the mutant alkaline protease of the present invention.

In the liquid detergent composition of the present invention, the content of the mutant alkaline protease of the present invention is not particularly limited as long as the alkaline protease exhibits activity. The content is preferably 0.1 to 25000 U per kg of the detergent composition, more preferably 0.1 to 5000 U and further preferably 0.1 to 2500 U.

The alkaline protease activity is measured by the following method: A 1/15 M phosphate buffer, pH 7.4 (0.9 mL) and a 40 mM Glt-Ala-Ala-Pro-Leu-p-nitroanilide/dimethyl sulfoxide solution (0.05 mL) are added in a test tube and maintained at 30° C. for 5 minutes. To this mixture, an enzyme liquid (0.05 mL) is added and allowed to react at 30° C. for 10 minutes. Thereafter, a 5% (w/v) aqueous citric acid solution (2.0 mL) is added to terminate the reaction. The absorbance at 420 nm is measured by a spectrophotometer. Herein, one unit (U) of enzyme is defined as the amount of enzyme for producing 1 μmol of p-nitroaniline for one minute in the above reaction.

The liquid detergent composition of the present invention contains a surfactant and water other than the alkaline protease mutant of the present invention. As the surfactant, surfactants such as an anionic surfactant, a nonionic surfactant, an amphoteric surfactant and a cationic surfactant may be used alone or in combination of two or more.

As the nonionic surfactant, any nonionic surfactant may be used as long as it contains a C8 to C22 hydrocarbon group generally contained in a liquid detergent and a C2 oxyalkylene group in an amount of several moles or more is added to the hydrocarbon group. For example, the following nonionic surfactants are mentioned:

$R_1O$-(AO)m-H ($R_1$=a C8-C22 hydrocarbon, AO=a C2-C5 oxyalkylene group, m=16 to 35) [JP-A-2010-275468];

$R_1O$-(EO)l-(AO)m-(EO)n-H ($R_1$=a C8-C18 hydrocarbon, EO=a C2 oxyalkylene group, AO=a C3-C5 oxyalkylene group, l=3 to 30, m=1 to 5, l+n=14 to 50) [JP-A-2010-265445, JP-A-2011-63784];

$R_1O$-(EO)m/(AO)n-H ($R_1$=a C8-C22 hydrocarbon, EO=a C2 oxyalkylene group, AO=a C3-C5 oxyalkylene group, m=10 to 30, n=0 to 5, EO and AO are randomly or block bound) [JP-A-2010-189551];

$R_1(CO)lO$-(EO)m/(AO)n-$R_2$ ($R_1$=a C8-C22 hydrocarbon, EO=a C2 oxyalkylene group, AO=a C3-C5 oxyalkylene group, l=0 to 1, m=14 to 50, n=1 to 5, $R_2$=hydrogen (l=0) or a C1-C3 alkyl group, EO and AO are randomly or block bound) [JP-A-2010-229385];

$R_1O$-(EO)m-(AO)n-H ($R_1$=a C8-C22 hydrocarbon, EO=a C2 oxyalkylene group, AO=a C3-05 oxyalkylene group, m=15 to 30, n=1 to 5) [JP-A-2010-229387];

$R_1O$-(AO)m/(Gly)n-H and/or $R_2$—COO-(AO)p/(Gly)q-H ($R_1$=a C8-C22 hydrocarbon group, $R_2$=a C7-C21 hydrocarbon group, AO=a C2-C3 oxyalkylene group, Gly=a glycerol group, m=0 to 5, n=2 to 10, p=0 to 5, q=2 to 10, AO and Gly are randomly or block bound) [JP-A-2010-254881];

$R_1$—COO—(PO) m/(EO)n-$R_2$ ($R_1$=a C7-C21 hydrocarbon group, COO=a carbonyloxy group, $R_2$=a C1-C3 alkyl group, PO=an oxypropylene group, EO=an oxyethylene group, m=0.3 to 5, n=8 to 25, PO and EO are randomly or block bound) [JP-A-2010-265333];

$R_1O$-(EO)l-(PO)m-(EO)n-H ($R_1$=a C8-C20 hydrocarbon, EO=a C2 oxyalkylene group, PO=an oxypropylene group, l>=1, n>=1, 0<m<1+n, EO and PO are block bound) [WO98/24865];

$R_1O$-(EO)m-(PO)n-H ($R_1$=a C10-C16 alkyl group or alkenyl group, EO=an ethylene oxide group, PO=a propylene oxide group, m=5 to 15, n=1 to 3) [JP-A-8-157867];

$R_1(CO)$-(EO)m-$OR_2$ ($R_1$=a C11-C13 straight or branched alkyl group or alkenyl group, $R_2$=a C1-C3 alkyl group, EO=an ethylene oxide group, m=10 to 20) [JP-A-2008-7706, JP-A-2009-7451, JP-A-2009-155594, JP-A-2009-155606];

$R_1(CO)$-(AO)m-$OR_2$ ($R_1$=a C9-C13 straight or branched alkyl group or alkenyl group, AO=a C2-C4 oxyalkylene group, $R_2$=a C1-C3 alkyl group, m=5 to 30) [JP-A-2009-144002, JP-A-2009-173858, JP-A-2010-189612]; and a fatty acid alkanol amide, a fatty acid alkanol glucamide, and an alkyl polyglucoside.

As the anion surfactant, a carboxylate anion surfactant, a sulfonic acid or sulfuric acid ester anion surfactant, a non-soap based anion surfactant, a straight-chain alkyl benzene sulfonic acid, a benzene sulfonic acid or a salt thereof, a polyoxyethylene alkyl sulfuric acid ester salt, an α-olefin sulfonic acid salt, an alkyl benzene sulfonic acid salt, an α-sulfo fatty acid salt, a fatty acid soap, a phosphoric acid ester salt based surfactant, an acyl alaninate, an acyl taurate, an alkyl ether carboxylic acid, an alcohol sulfuric acid ester and others are mentioned. Preferably, a quaternary ammonium surfactant having a single long-chain alkyl group having 8 to 22 carbon atoms and a tertiary amine having a single long-chain alkyl group having 8 to 22 carbon atoms are mentioned.

As the cationic surfactant, for example, a quaternary ammonium salt having a long-chain alkyl group, a tertiary amine having a single long-chain alkyl group, an alkyltrimethyl ammonium salt, a dialkyldimethyl ammonium salt and an alkylpyridinium salt are mentioned. As the amphoteric surfactant, an alkyl betaine type, alkyl amide betaine type, imidazoline type, alkyl amino sulfone type, alkyl amino carboxylic acid type, alkyl amide carboxylic acid type, amide amino acid type or phosphoric acid type amphoteric surfactants such as an alkylacetic acid betaine, alkanol amide propylacetic acid betaine, alkyl imidazoline and alkyl alanine, are mentioned. Preferably, a sulfobetaine or a carbobetaine having an alkyl group having 10 to 18 carbon atoms may be mentioned.

The liquid detergent composition of the present invention is preferably a concentrated liquid detergent composition. In this specification, the "concentrated liquid detergent" may refer to a liquid detergent comprising a surfactant in a concentration of 40 mass % or more and water in a concentration of less than 60 mass %, preferably, a liquid detergent comprising a surfactant in a concentration of 40 to 90 mass % and water in a concentration of 5 mass % or more and less than 60 mass %, more preferably, a liquid detergent comprising a surfactant in a concentration of 45 to 90 mass % and water in a concentration of 5 mass % or more and less than 55 mass %, further preferably, a liquid detergent comprising a surfactant in a concentration of 50 to 75 mass % and water in a concentration of 5 mass % or more and less than 50 mass %, and further more preferably, a liquid detergent comprising a surfactant in a concentration of 50 to 75 mass % and water in a concentration of 5 mass % or more and less than 30 mass %.

The liquid detergent composition of the present invention may further contain components usually used in a liquid detergent, such as a water-soluble polymer, a water-miscible organic solvent, an alkali agent, a chelating reagent, an organic acid or a salt thereof, an enzyme other than the mutant alkaline protease of the present invention, an enzyme stabilizing agent, a fluorescent agent, an anti-refouling agent, a finish agent, a bleaching agent such as hydrogen peroxide, an antioxidant, a pH adjuster, a buffer, a preservative, a flavor, a salt, an alcohol and a saccharide.

Examples of the water-soluble polymer include a polymer compound (JP-A-2010-275468, JP-A-10-060496) having (i) a polyether chain moiety comprising a polymerization unit derived from an epoxide having 2 to 5 carbon atoms and (ii) a polymer chain moiety comprising a polymerization unit derived from at least one unsaturated carboxylic acid monomer selected from acrylic acid, methacrylic acid and maleic acid, and a graft structure in which either (i) or (ii) serves as a backbone chain and the other serves as a branch chain; and a water soluble polymer (JP-A-2009-155606) having an alkylene terephthalate unit and/or an alkylene isophthalate unit, and an oxyalkylene unit and/or a polyoxyalkylene unit.

Examples of the water-miscible organic solvent include alkylene glycols of alkanols, glycerin, polyalkylene glycols, (poly)alkylene glycol (mono or di)alkylethers, alkylglyceryl ethers and aromatic ethers of (poly)alkylene glycols. An alkylene glycol having 2 to 6 carbon atoms, such as ethylene glycol, propylene glycol, butylene glycol or hexylene glycol, glycerin, polyethylene glycol monophenyl ether, ethylene glycol monobenzyl ether, diethylene glycol monobenzyl ether or the like is preferable. In the liquid detergent composition of the present invention, the content of the water-miscible organic solvent is 1 to 40 mass %, and preferably, 1 to 35 mass %.

Examples of the alkali agent include an alkanol amine having 1 to 3 C2-C4 alkanols such as monoethanol amine, diethanol amine, triethanol amine, polyoxyalkylene amine and dimethyl aminopropyl amine. Monoethanol amine or triethanol amine is preferable. In the liquid detergent composition of the present invention, the content of the alkali agent is 0 to 20 mass %, and preferably, 0 to 10 massa.

As the chelating agent, for example, aminopolyacetic acids such as nitrilotriacetic acid, iminodiacetic acid, ethylenediamineacetic acid, diethylenetriaminepentaacetic acid, glycoletherdiaminetetraacetic acid, hydroxyethyliminodiacetic acid, triethylenetetraminehexaacetic acid and djenkolic acid, or salts of these; organic acids such as diglycol acid, oxydisuccinic acid, carboxymethyloxysuccinic acid, citric acid, lactic acid, tartaric acid, oxalic acid, malic acid, oxydisuccinic acid, gluconic acid, carboxymethylsuccinic acid and carboxymethyltartaric acid or salts of these; and aminotri(methylenephosphonic acid), 1-hydroxyethylidene-1,1-diphosphonic acid, ethylenediaminetetra(methylenephosphonic acid), diethylenetriaminepenta(methylenephosphonic acid), alkali metals of these or lower amine salts are mentioned. In the liquid detergent composition of the present invention, the content of the chelating agent is preferably 0.1 to 5 mass % and more preferably 0.1 to 4 mass %.

As the organic acid or a salt thereof, for example, polyvalent carboxylic acids such as saturated fatty acids, succinic acid, maleic acid, fumaric acid or salts of these; hydroxycarboxylic acids such as citric acid, malic acid, glycol acid, p-hydroxybenzoic acid, benzoic acid or salts thereof are mentioned. Of them, citric acid or a salt thereof is more preferable. In the liquid detergent composition of the present invention, the content of the organic acid or a salt thereof is 0 to 5 mass %, and preferably, 0 to 3 mass %.

Examples of the anti-refouling agent and a dispersant include polyacrylic acid, polymaleic acid, carboxymethylcellulose, polyethylene glycol having an weight average molecular weight of 5000 or more, a maleic anhydride-diisobutylene copolymer, a maleic anhydride-methylvinyl ether copolymer, a maleic anhydride-vinyl acetate copolymer, a naphthalene sulfonate formalin condensation product and polymers described in claims 1 to 21 (page 1, column 3, line 5 to page 3, column 4, line 14) of JP-A-59-62614. If they are not suitable for blending, they may not be added.

As an anti-color staining agent, for example, polyvinylpyrrolidone is mentioned. The content thereof is preferably 0.01 to 10 mass %.

Examples of the bleaching agent include hydrogen peroxide, percarbonate and perborate. The content thereof is preferably 1 to 10 mass %. When a bleaching agent is used, tetraacetylethylenediamine (TAED) and a bleaching activator as described in JP-A-6-316700 can be added in an amount of 0.01 to 10 mass %.

Examples of the fluorescent agent include a biphenyl fluorescent agent (e.g., Tinopal CBS-X) and a stilbene fluorescent agent (e.g., DM fluorescent dye). The content of the fluorescent agent is preferably 0.001 to 2 mass %.

Examples of other enzymes except the mutant alkaline protease of the present invention include other types of proteases and hydrolases such as cellulase, β-glucanase, hemicellulase, lipase, peroxidase, laccase, α-amylase, glucoamylase, cutinase, pectinase, reductase, oxidase, phenol oxidase, ligninase, pullulanase, pectate lyase, xyloglucanase, xylanase, pectin acetylesterase, polygalacturonase, rhamnogalacturonase, pectin lyase, other types of mannanase, pectinmethyl esterase, cellobiohydrolase, and transglutaminase and a mixture of two or more of these enzymes.

As other components, for example, an enzyme stabilizer such as a boron compound, a calcium ion source (calcium ion supplying compound), a bihydroxy compound and formic acid; an antioxidant such as butylhydroxytoluene, distyrenated cresol, sodium sulfite and sodium hydrogen sulfite; a solubilizer such as paratoluenesulfonic acid, cumen sulfonic acid, metaxylenesulfonic acid, benzoate (effective as a preservative), a water-immiscible organic solvent including a paraffin such as octane, decane, dodecane and tridecane; an olefin such as decene and dodecene; a halogenated alkyl such as methylene chloride and 1,1,1-trichloroethane; a terpene such as D-limonene, a pigment, a flavor, an antibiotic preservative and a defoaming agent such as silicone may be added.

As a preferable liquid detergent composition of the present invention, a composition described in Examples of JP-A-2010-189551, JP-A-2010-265333, JP-A-2010-275468, WO2010/058832, WO2010/119935 or WO2010/137635 is mentioned. More specifically, any liquid detergent composition may be used as described in Examples of JP-A-2010-275468. As a specific example, the liquid detergent composition described in Example 3 may be mentioned which can be prepared by adding an enzyme to a composition comprising e.g., 66% of a surfactant (a nonionic surfactant: 46%; an anionic surfactant: 20%), 3% of a water soluble polymer (polyethylene glycol (ethylene oxide average addition mole number: 25), allyl ether/acrylic acid=75/25 (mass ratio) copolymer), 14% of a water miscible organic solvent (diethylene glycol monobutyl ether, propylene glycol), 5% of an alkali agent (monoethanol amine), 11% of an ion exchange water and a pigment, flavor (composition C).

For example, the following commercially available liquid detergent composition is a concentrated liquid detergent comprising a surfactant of 40% or more. The components described in the product labeling will be shown below.

Composition A (Attack Neo; manufactured by Kao Corp.): a surfactant (nonionic surfactant, anionic surfactant: straight alkyl benzene base, fatty acid base) 74%, a stabilizing agent (butyl carbitol), an alkali agent, a dispersant and an enzyme.

Composition B (NANOX; manufactured by Lion Corporation): a surfactant (polyoxyethylenealkyl sulfate) 55%, a stabilizing agent and an enzyme.

The liquid detergent composition of the present invention is preferably used for clothing materials or fabrics (sheets, curtains, carpets, wall cloths), although it is not limited to these. Since the detergent composition according to the present invention can contain the mutant alkaline protease of the present invention in a large amount compared to a conventional one, high enzymatic detergency can be provided.

The present invention further includes the following compositions, production method, uses or methods as exemplified embodiments.

<1> A method of improving solubility of an alkaline protease in a liquid detergent, the method comprising a step of, in an alkaline protease consisting of the amino acid sequence represented by SEQ ID No: 2 or an amino acid sequence having 80% or more identity therewith, substituting at least one amino acid residue selected from the group consisting of the amino acid residues at positions described in column (i) of Tables 1-1 and 1-2 of the amino acid sequence represented by SEQ ID No: 2 or the positions corresponding thereto, with an amino acid residue described in column (ii) of Tables 1-1 and 1-2.

<2> A mutant alkaline protease consisting of the amino acid sequence represented by SEQ ID No: 2 or an amino acid sequence having 80% or more identity therewith, in which at least one amino acid residue selected from the group consisting of the amino acid residues at positions described in column (i) of Tables 2-1 and 2-2 of the amino acid sequence represented by SEQ ID No: 2 or corresponding positions thereto is an amino acid residue described in column (ii) of Tables 2-1 and 2-2.

<3> In the above <1> and <2>, the alkaline protease having an identity of 80% or more with the amino acid sequence represented by SEQ ID No: 2 is an alkaline protease having an identity of preferably 85% or more, more preferably 90% or more, further preferably 95% or more, further more preferably 97% or more, still preferably 97.5% or more, still more preferably 98% or more and still further preferably, 99% or more, with the amino acid sequence represented by SEQ ID No: 2.

<4> In the above <1> to <2>, the alkaline protease having an identity of 80% or more with the amino acid sequence represented by SEQ ID No: 2 is preferably an alkaline protease consisting of the amino acid sequence represented by SEQ ID No: 2 having a deletion, substitution or addition of preferably 1 to 40, more preferably 1 to 20, and further preferably, 1 to 10 amino acids.

<5> In the above <1> to <2>, the alkaline protease having an identity of 80% or more with the amino acid sequence represented by SEQ ID No: 2 is a protease preferably selected from the group consisting of:

Protease KP9860 [derived from *Bacillus* sp. KSM-KP9860 (FERM BP-6534), WO99/18218, GenBank accession no. AB046403];

Protease E-1 [derived from *Bacillus* No. D-6 (FERM P-1592), JP-A-49-71191, GenBank accession no. AB046402];

Protease Ya [derived from *Bacillus* sp. Y (FERM BP-1029), JP-A-61-280268, GenBank accession no. AB046404];

Protease SD521 [derived from *Bacillus* SD521 (FERM P-11162), JP-A-3-191781, GenBank accession no. AB046405];

Protease A-1 [derived from NCIB12289, WO88/01293, GenBank accession no. AB046406];

Protease A-2 [derived from NCIB12513, WO98/56927]; or Protease 9865 [derived from *Bacillus* sp. KSM-9865 (FERM P-18566), GenBank accession no. AB084155].

<6> In the above <1> to <2>, the alkaline protease having an identity of 80% or more with the amino acid sequence represented by SEQ ID No: 2 is an alkaline protease obtained by substituting, preferably, tyrosine at position 195 of the amino acid sequence represented by SEQ ID No: 2, with glutamine, aspartic acid at position 369 with asparagine, threonine at position 65 with proline, valine at position 273 with isoleucine, threonine at position 359 with serine, serine at position 387 with alanine, asparagine at position 166 with glycine, glycine at position 167 with valine, alanine at position 133 with serine and valine at position 134 with threonine, and by inserting serine between position 133 and position 134; more preferably, an alkaline protease consisting of the amino acid sequence represented by SEQ ID No: 250.

<7> In the above <1> to <6>, preferably, the alkaline protease having an identity of 80% or more with the amino acid sequence represented by SEQ ID No: 2 has the following amino acid residues at the positions corresponding to positions 30, 68 and 255 of the amino acid sequence represented by SEQ ID No: 2:

Position corresponding to position 30: aspartic acid
Position corresponding to position 68: histidine
Position corresponding to position 255: serine.

<8> In the above <7>, preferably, the alkaline protease having an identity of 80% or more with the amino acid sequence represented by SEQ ID No: 2 has the amino acid residues described in column (ii) of Table 3 at the positions corresponding to the positions described in column (i) of Table 3 of the amino acid sequence represented by SEQ ID No: 2.

<9> In the above <1> to <8>, preferably, the at least one amino acid residue comprises at least one selected from the group consisting of the amino acid residues at position 405, position 81, position 40, position 191 and position 59 of the amino acid sequence represented by SEQ ID No: 2 or the corresponding positions thereto.

<10> In the above <1> to <9>, preferably, the at least one amino acid residue comprises at least two selected from the group consisting of amino acid residues at position 405, position 81, position 40, position 191 and position 59 of the amino acid sequence represented by SEQ ID No: 2 or the corresponding positions thereto.

<11> In the method for improving solubility of an alkaline protease described in the above <1>, <3> to <10>, preferably, the at least one amino acid residue selected from the group consisting of the amino acid residues at position 405, position 81, position 40, position 191 and position 59 of the amino acid sequence represented by SEQ ID No: 2 or the corresponding positions thereto are substituted with an amino acid residue described below:

Position 405 or the corresponding position thereto: leucine or tryptophan;
Position 81 or the corresponding position thereto: leucine, proline, tyrosine or tryptophan;
Position 40 or the corresponding position thereto: isoleucine, phenylalanine or leucine;
Position 191 or the corresponding position thereto: leucine or valine; and
Position 59 or the corresponding position thereto: valine, isoleucine or leucine.

<12> In the alkaline protease mutant described in the above <2> to <10>, preferably, the at least one amino acid residue selected from the group consisting of amino acid residues at position 405, position 81, position 40, position 191 and position 59 of the amino acid sequence represented by SEQ ID No: 2 or the corresponding positions thereto is an amino acid residue described below:

Position 405 or the corresponding position thereto: leucine or tryptophan;
Position 81 or the corresponding position thereto: leucine, proline, tyrosine or tryptophan;
Position 40 or the corresponding position thereto: isoleucine, phenylalanine or leucine;
Position 191 or the corresponding position thereto: leucine or valine; and
Position 59 or the corresponding position thereto: valine, isoleucine or leucine.

<13> In the above <1>, <3> to <11>, the liquid detergent contains preferably a surfactant in a concentration of 40 mass % or more and water in a concentration of less than 60 mass %, more preferably, a surfactant in a concentration of 40 to 90 mass % and water in a concentration of 5 mass % or more and less than 60 mass %, further preferably, a surfactant in a concentration of 45 to 90 mass % and water in a concentration of 5 mass % or more and less than 55 mass %, further more preferably, a surfactant in a concentration of 50 to 75 mass % and water in a concentration of 5 mass % or more and less than 50 mass %, and sill preferably, a surfactant in a concentration of 50 to 75 mass % and water in a concentration of 5 mass % or more and less than 30 mass %.

<14> A gene encoding the mutant alkaline protease described in any one of the above <2> to <10> and <12>, or an alkaline protease exhibiting an improved solubility described in any one of the above <1> to <11> and <13>.

<15> A recombinant vector comprising a gene described in the above <14>.

<16> A transformant comprising a recombinant vector described in the above <17>.

<17> A method of producing a mutant alkaline protease using a transformant described in the above <16>.

<18> A liquid detergent composition comprising a mutant alkaline protease described in any one of the above <2> to <10> and <12> or an alkaline protease exhibiting an improved solubility described in any one of the above <1> to <11> and <13>.

<19> In the above <18>, the above liquid detergent composition comprises, preferably a surfactant in a concentration of 40 mass % or more and water in a concentration of less than 60 mass %, more preferably, a surfactant in a concentration of 40 to 90 mass % and water in a concentration of 5 mass % or more and less than 60 mass %, further preferably, a surfactant in a concentration of 45 to 90 mass % and water in a concentration of 5 mass % or more and less than 55 mass %, further more preferably, a surfactant in a concentration of 50 to 75 mass % and water in a concentration of 5 mass % or more and less than 50 mass %, and still more preferably, a surfactant in a concentration of 50 to 75 mass % and water in a concentration of 5 mass % or more and less than 30 mass %.

EXAMPLES

The present invention will be more specifically described by way of Examples, below. However, the technical range of the present invention is not limited to these Examples.

Example 1

Preparation of Mutant Alkaline Protease

The method for preparing a mutant alkaline protease of the present invention will be described below by way of preparation of e.g., a mutant "D11G", by mutating the aspartic acid residue (D11) at position 11 of the amino acid sequence (SEQ ID No: 2) of the wild type KP43 protease mature enzyme region with glycine, as an example.

Using plasmid pHA64TSB described in Reference Example 1 (2) (described later) sufficiently diluted as a template; primer KG24S2 (SEQ ID No: 3: ATAAGGATC-CGTGAGGAGGGAACCGA, having a BamHI site), which complementarily anneals to an upstream region of an initiation codon, and primer D11_R (SEQ ID No: 4: CGCTTT-GACAATTCCACGCGCAAC), which complementarily anneals to an upstream region adjacent to D11 codon, PCR was performed to amplify a DNA sequence encoding KP43 protease N-terminal region. Then, using plasmid pHA64TSB as a template, primer D11G_F (SEQ ID No: 5: GGAATTGTCAAAGCGGGAGTGGCTCAGAGCAGC-TAC, part of the 5' side thereof complementarily binds to primer D11_R) for substituting the codon D11 with a glycine codon, and primer KG11S (SEQ ID No: 6: CCCCTCTA-GACGATTACCATATTAATTCCTCTACCC, having an XbaI site), which complementarily anneals to a downstream region of the termination codon, PCR was performed to amplify a DNA sequence encoding a C-terminal region of KP43 protease. Using a mixture of the obtained PCR product encoding the N-terminal region and the obtained PCR product encoding the C-terminal region as a template, and using the previous primer KG24S2 and primer KG11S, PCR was performed to obtain a PCR product having a full-length gene of KP43 protease mutant in which D11 codon is changed with a glycine codon. Subsequently, the PCR product was purified by ethanol precipitation, digested simultaneously with restriction enzyme BamHI and XbaI and mixed with a gene insertion/expression vector described in Reference Example 1 (1) (described later) to perform a ligation reaction by using Ligation High (manufactured by Toyobo Co., Ltd.). The ligation product was purified by ethanol precipitation. Thereafter, a host bacterium, Bacillus sp. KSM-9865 strain (FERM P-18566) was transformed with this in accordance with an electroporation method and smeared onto a skim milk-containing alkali LB agar medium. Several days later, colonies were formed in the agar medium. From the colonies, a transformant having ability to form plaque on the skim milk was separated to obtain the transformant producing mutant KP43 protease "D11G" in which D11 was mutated with glycine.

Similarly, the same operation was repeated by using two primers described in the column "mutation primer R" and the column "mutation primer F" of the following Tables 6-1 to 6-13 respectively in place of primer D11_R and primer D11G_F to obtain transformants producing mutants KP43 protease having mutations described in the column of "KP43 protease mutation" of the following Tables 6-1 to 6-13. The obtained transformants were each cultured in the same method as described in Reference Example 1 (2) to obtain a culture supernatant containing a protease mutant.

TABLE 6-1

| KP43 protease mutation | Mutation primer R | | Mutation primer F | |
|---|---|---|---|---|
| | Primer name | Sequence | Primer name | Sequence |
| D11G | D11_R | CGCTTTGACAATTCCACGCG-CAAC (SEQ ID No: 4) | D11G_F | GGAATTGTCAAAGCGGGAGTGGCTCAGAGCAGC-TAC (SEQ ID No: 5) |
| D11N | D11_R | CGCTTTGACAATTCCACGCG-CAAC (SEQ ID No: 4) | D11N_F | GGAATTGTCAAAGCGAATGTGGCTCAGAGCAGC-TAC (SEQ ID No: 7) |
| D11S | D11_R | CGCTTTGACAATTCCACGCG-CAAC (SEQ ID No: 4) | D11S_F | GGAATTGTCAAAGCGTCCGTGGCTCAGAGCAGC-TAC (SEQ ID No: 8) |

TABLE 6-1-continued

| KP43 protease mutation | Mutation primer R | | Mutation primer F | |
|---|---|---|---|---|
| | Primer name | Sequence | Primer name | Sequence |
| S16I | S16_R | GCTCTGAGCCACATCCGCTTT-GAC (SEQ ID No: 9) | S16I_F | GATGTGGCTCAGAGCATTTACGGGTTGTATGGA-CAA (SEQ ID No: 10) |
| S16L | S16_R | GCTCTGAGCCACATCCGCTTT-GAC (SEQ ID No: 9) | S16L_F | GATGTGGCTCAGAGCCTTTACGGGTTGTATGGA-CAA (SEQ ID No: 11) |
| S16V | S16_R | GCTCTGAGCCACATCCGCTTT-GAC (SEQ ID No: 9) | S16V_F | GATGTGGCTCAGAGCGTGTACGGGTTGTATGGA-CAA (SEQ ID No: 12) |
| S16W | S16_R | GCTCTGAGCCACATCCGCTTT-GAC (SEQ ID No: 9) | S16W_F | GATGTGGCTCAGAGCTGGTACGGGTTGTATGGA-CAA (SEQ ID No: 13) |
| Y20A | Y20_R | CAACCCGTAGCTGCTCTGAGC-CAC (SEQ ID No: 14) | Y20A_F | AGCAGCTACGGGTTGGCAGGACAAGGACA-GATCGTA (SEQ ID No: 15) |
| Q22W | Q22_R | TCCATACAACCCGTAGCT-GCTCTG (SEQ ID No: 16) | Q22W_F | TACGGGTTGTATGGATGGGGACAGATCGTAGCG-GTT (SEQ ID No: 17) |
| G23N | G23_R | TTGTCCATACAACCCGTAGCT-GCT (SEQ ID No: 18) | G23N_F | GGGTTGTATGGACAAAATCAGATCGTAGCGGTT-GCC (SEQ ID No: 19) |
| R37T | R37_R | ACCTGTATCAAGCCCTG-TATCGGC (SEQ ID No: 20) | R37T_F | GGGCTTGATACAGGTACAAATGACAGTTCGATG-CAT (SEQ ID No: 21) |
| S40F | S40_R | GTCATTGCGACCTGTAT-CAAGCCC (SEQ ID No: 22) | S40F_F | ACAGGTCGCAATGACTTCTCGATGCATGAAGC-CTTC (SEQ ID No: 23) |
| S40I | S40_R | GTCATTGCGACCTGTAT-CAAGCCC (SEQ ID No: 22) | S40I_F | ACAGGTCGCAATGACATTTCGATGCATGAAGC-CTTC (SEQ ID No: 24) |
| S40L | S40_R | GTCATTGCGACCTGTAT-CAAGCCC (SEQ ID No: 22) | S40L_F | ACAGGTCGCAATGACCTTTCGATGCATGAAGC-CTTC (SEQ ID No: 25) |

TABLE 6-2

| KP43 protease mutation | Mutation primer R | | Mutation primer F | |
|---|---|---|---|---|
| | Primer name | Sequence | Primer name | Sequence |
| S40V | S40_R | GTCATTGCGACCTGTATCAAGCCC (SEQ ID No: 22) | S40V_F | ACAGGTCGCAATGACGTGTCGATGCATGAAGCCTTC (SEQ ID No: 26) |
| S40W | S40_R | GTCATTGCGACCTGTATCAAGCCC (SEQ ID No: 22) | S40W_F | ACAGGTCGCAATGACTGGTCGATGCATGAAGCCTTC (SEQ ID No: 27) |
| S41I | S41I_R | ACTGTCATTGCGACCTGTATCAAG (SEQ ID No: 28) | S41I_F | GGTCGCAATGACAGTATTATGCATGAAGCCTTCCGC (SEQ ID No: 29) |
| A52G | A52_R | AGTAATTTTCCCGCGGAAGGCTTC (SEQ ID No: 30) | A52G_F | CGCGGGAAAATTACTGGATTATATGCATTGGGACGG (SEQ ID No: 31) |
| A52S | A52_R | AGTAATTTTCCCGCGGAAGGCTTC (SEQ ID No: 30) | A52S_F | CGCGGGAAAATTACTTCCTTATATGCATTGGGACGG (SEQ ID No: 32) |
| L53A | L53_R | TGCAGTAATTTTCCCGCGGAAGGC (SEQ ID No: 33) | L53A_F | GGGAAAATTACTGCAGCATATGCATTGGGACGGACG (SEQ ID No: 34) |
| L53I | L53_R | TGCAGTAATTTTCCCGCGGAAGGC (SEQ ID No: 33) | L53I_F | GGGAAAATTACTGCAATTTATGCATTGGGACGGACG (SEQ ID No: 35) |
| L53V | L53_R | TGCAGTAATTTTCCCGCGGAAGGC (SEQ ID No: 33) | L53V_F | GGGAAAATTACTGCAGTGTATGCATTGGGACGGACG (SEQ ID No: 36) |

TABLE 6-2-continued

| KP43 protease mutation | Mutation primer R | | Mutation primer F | |
|---|---|---|---|---|
| | Primer name | Sequence | Primer name | Sequence |
| L56V | L56_R | TGCATATAATGCAGTAATTTTCCC (SEQ ID No: 37) | L56V_F | ACTGCATTATATGCAGTGGGACGGACGAATAATGCC (SEQ ID No: 38) |
| T59F | T59_R | CCGTCCCAATGCATATAATGCAGT (SEQ ID No: 39) | T59F_F | TATGCATTGGGACGGTTCAATAATGCCAATGATACG (SEQ ID No: 40) |
| T59I | T59_R | CCGTCCCAATGCATATAATGCAGT (SEQ ID No: 39) | T59I_F | TATGCATTGGGACGGATTAATAATGCCAATGATACG (SEQ ID No: 41) |
| T59L | T59_R | CCGTCCCAATGCATATAATGCAGT (SEQ ID No: 39) | T59L_F | TATGCATTGGGACGGCTTAATAATGCCAATGATCCG (SEQ ID No: 42) |
| T59M | T59_R | CCGTCCCAATGCATATAATGCAGT (SEQ ID No: 39) | T59M_F | TATGCATTGGGACGGATGAATAATGCCAATGATACG (SEQ ID No: 43) |

TABLE 6-3

| KP43 protease mutation | Mutation primer R | | Mutation primer F | |
|---|---|---|---|---|
| | Primer name | Sequence | Primer name | Sequence |
| T59V | T59_R | CCGTCCCAATGCATATAATGCAGT (SEQ ID No: 39) | T59V_F | TATGCATTGGGACGGGTGAATAATGCCAATGATACG (SEQ ID No: 44) |
| T59W | T59_R | CCGTCCCAATGCATATAATGCAGT (SEQ ID No: 39) | T59W_F | TATGCATTGGGACGGTGGAATAATGCCAATGATACG (SEQ ID No: 45) |
| N60F | N60_R | CGTCCGTCCCAATGCATATAATGC (SEQ ID No: 46) | N60F_F | GCATTGGGACGGACGTTCAATGCCAATGATACGAAT (SEQ ID No: 47) |
| N60I | N60_R | CGTCCGTCCCAATGCATATAATGC (SEQ ID No: 46) | N60I_F | GCATTGGGACGGACGATTAATGCCAATGATACGAAT (SEQ ID No: 48) |
| N60L | N60_R | CGTCCGTCCCAATGCATATAATGC (SEQ ID No: 46) | N60L_F | GCATTGGGACGGACGCTTAATGCCAATGATACGAAT (SEQ ID No: 49) |
| N60V | N60_R | CGTCCGTCCCAATGCATATAATGC (SEQ ID No: 46) | N60V_F | GCATTGGGACGGACGGTGAATGCCAATGATACGAAT (SEQ ID No: 50) |
| N60W | N60_R | CGTCCGTCCCAATGCATATAATGC (SEQ ID No: 46) | N60W_F | GCATTGGGACGGACGTGGAATGCCAATGATACGAAT (SEQ ID No: 51) |
| N63D | N63_R | GGCATTATTCGTCCGTCCCAATGC (SEQ ID No: 52) | N63D_F | CGGACGAATAATGCCGATGATACGAATGGTCATGGT (SEQ ID No: 53) |
| N63L | N63_R | GGCATTATTCGTCCGTCCCAATGC (SEQ ID No: 52) | N63L_F | CGGACGAATAATGCCCTTGATACGAATGGTCATGGT (SEQ ID No: 54) |
| G80A | G80_R | GTTTCCTAATACGGAGCCAGCCAC (SEQ ID No: 55) | G80A_F | TCCGTATTAGGAAACGCATCCACTAATAAAGGAATG (SEQ ID No: 56) |
| G80H | G80_R | GTTTCCTAATACGGAGCCAGCCAC (SEQ ID No: 55) | G80H_F | TCCGTATTAGGAAACCATTCCACTAATAAAGGAATG (SEQ ID No: 57) |
| S81F | S81_R | GCCGTTTCCTAATACGGAGCCAGC (SEQ ID No: 58) | S81F_F | GTATTAGGAAACGGCTTCACTAATAAAGGAATGGCG (SEQ ID No: 59) |
| S81I | S81_R | GCCGTTTCCTAATACGGAGCCAGC (SEQ ID No: 58) | S81I_F | GTATTAGGAAACGGCATTACTAATAAAGGAATGGCG (SEQ ID No: 60) |
| S81L | S81_R | GCCGTTTCCTAATACGGAGCCAGC (SEQ ID No: 58) | S81L_F | GTATTAGGAAACGGCCTTACTAATAAAGGAATGGCG (SEQ ID No: 61) |

TABLE 6-4

| KP43 protease mutation | Mutation primer R | | Mutation primer F | |
|---|---|---|---|---|
| | Primer name | Sequence | Primer name | Sequence |
| S81Q | S81_R | GCCGTTTCCTAATACGGAGCCAGC (SEQ ID No: 58) | S81Q_F | GTATTAGGAAACGGCCAGACTAATAAAGGAATGGCG (SEQ ID No: 62) |
| S81W | S81_R | GCCGTTTCCTAATACGGAGCCAGC (SEQ ID No: 58) | S81W_F | GTATTAGGAAACGGCTGGACTAATAAAGGAATGGCG (SEQ ID No: 63) |
| S81Y | S81_R | GCCGTTTCCTAATACGGAGCCAGC (SEQ ID No: 58) | S81Y_F | GTATTAGGAAACGGCTATACTAATAAAGGAATGGCG (SEQ ID No: 64) |
| T82Q | T82_R | GGAGCCGTTTCCTAATACGGAGC (SEQ ID No: 65) | T82Q_F | TTAGGAAACGGCTCCCAGAATAAAGGAATGGCGCCT (SEQ ID No: 66) |
| N91C | N91_R | CGCCTGAGGCGCCATTCCTTTATT (SEQ ID No: 67) | N91C_F | ATGGCGCCTCAGGCGTGCCTAGTCTTCCAATCTATC (SEQ ID No: 68) |
| S100F | S100_R | ATCCATGATAGATTGGAAGACTAG (SEQ ID No: 69) | S100F_F | CAATCTATCATGGATTTCGGTGGGGGACTTGGAGGA (SEQ ID No: 70) |
| S100I | S100_R | ATCCATGATAGATTGGAAGACTAG (SEQ ID No: 69) | S100I_F | CAATCTATCATGGATATTGGTGGGGGACTTGGAGGA (SEQ ID No: 71) |
| S100L | S100_R | ATCCATGATAGATTGGAAGACTAG (SEQ ID No: 69) | S100L_F | CAATCTATCATGGATCTTGGTGGGGGACTTGGAGGA (SEQ ID No: 72) |
| S100W | S100_R | ATCCATGATAGATTGGAAGACTAG (SEQ ID No: 69) | S100W_F | CAATCTATCATGGATTGGGGTGGGGGACTTGGAGGA (SEQ ID No: 73) |
| G101F | G101_R | GCTATCCATGATAGATTGGAAGAC (SEQ ID No: 74) | G101F_F | TCTATCATGGATAGCTTCGGGGGACTTGGAGGACTA (SEQ ID No: 75) |
| G101I | G101_R | GCTATCCATGATAGATTGGAAGAC (SEQ ID No: 74) | G101I_F | TCTATCATGGATAGCATTGGGGGACTTGGAGGACTA (SEQ ID No: 76) |
| G101L | G101_R | GCTATCCATGATAGATTGGAAGAC (SEQ ID No: 74) | G101L_F | TCTATCATGGATAGCCTTGGGGGACTTGGAGGACTA (SEQ ID No: 77) |
| G101V | G101_R | GCTATCCATGATAGATTGGAAGAC (SEQ ID No: 74) | G101V_F | TCTATCATGGATAGCGTGGGGGGACTTGGAGGACTA (SEQ ID No: 78) |
| G101W | G101_R | GCTATCCATGATAGATTGGAAGAC (SEQ ID No: 74) | G101W_F | TCTATCATGGATAGCTGGGGGGGACTTGGAGGACTA (SEQ ID No: 79) |

TABLE 6-5

| KP43 protease mutation | Mutation primer R | | Mutation primer F | |
|---|---|---|---|---|
| | Primer name | Sequence | Primer name | Sequence |
| G101Y | G101_R | GCTATCCATGATAGATTGGAAGAC (SEQ ID No: 74) | G101Y_F | TCTATCATGGATAGCTATGGGGGACTTGGAGGACTA (SEQ ID No: 80) |
| S109F | S109_R | AGGTAGTCCTCCAAGTCCCCCACC (SEQ ID No: 81) | S109F_F | CTTGGAGGACTACCTTTCAATCTGCAAACCTTATTC (SEQ ID No: 82) |
| S109I | S109_R | AGGTAGTCCTCCAAGTCCCCCACC (SEQ ID No: 81) | S109I_F | CTTGGAGGACTACCTATTAATCTGCAAACCTTATTC (SEQ ID No: 83) |
| S109L | S109_R | AGGTAGTCCTCCAAGTCCCCCACC (SEQ ID No: 81) | S109L_F | CTTGGAGGACTACCTCTTAATCTGCAAACCTTATTC (SEQ ID No: 84) |
| T113L | T113_R | TTGCAGATTCGAAGGTAGTCCTCC (SEQ ID No: 85) | T113L_F | CCTTCGAATCTGCAACTTTATTCAGCCAAGCATAC (SEQ ID No: 86) |
| T113W | T113_R | TTGCAGATTCGAAGGTAGTCCTCC (SEQ ID No: 85) | T113W_F | CCTTCGAATCTGCAATGGTATTCAGCCAAGCATAC (SEQ ID No: 87) |
| S120F | S120_R | GTATGCTTGGCTGAATAAGGTTTG (SEQ ID No: 88) | S120F_F | TTCAGCCAAGCATACTTCGCTGGTGCCAGAATTCAT (SEQ ID No: 89) |
| S120I | S120_R | GTATGCTTGGCTGAATAAGGTTTG (SEQ ID No: 88) | S120I_F | TTCAGCCAAGCATACATTGCTGGTGCCAGAATTCAT (SEQ ID No: 90) |

TABLE 6-5-continued

| KP43 protease mutation | Mutation primer R | | Mutation primer F | |
|---|---|---|---|---|
| | Primer name | Sequence | Primer name | Sequence |
| S120W | S120_R | GTATGCTTGGCTGAATAAGGTTTG (SEQ ID No: 88) | S120W_F | TTCAGCCAAGCATACTGGGCTGGTGCCAGAATTCAT (SEQ ID No: 91) |
| S120Y | S120_R | GTATGCTTGGCTGAATAAGGTTTG (SEQ ID No: 88) | S120Y_F | TTCAGCCAAGCATACTATGCTGGTGCCAGAATTCAT (SEQ ID No: 92) |
| N135L | N135_R | CACTGCTGCTCCCCAGGAGTTTGT (SEQ ID No: 93) | N135L_F | TGGGGAGCAGCAGTGCTTGGGGCTTACACAACAGAT (SEQ ID No: 94) |
| T140F | T140_R | TGTGTAAGCCCCATTCACTGCTGC (SEQ ID No: 95) | T140F_F | AATGGGGCTTACACATTCGATTCCAGAAATGTGGAT (SEQ ID No: 96) |
| T140L | T140_R | TGTGTAAGCCCCATTCACTGCTGC (SEQ ID No: 95) | T140L_F | AATGGGGCTTACACACTTGATTCCAGAAATGTGGAT (SEQ ID No: 97) |
| T140W | T140_R | TGTGTAAGCCCCATTCACTGCTGC (SEQ ID No: 95) | T140W_F | AATGGGGCTTACACATGGGATTCCAGAAATGTGGAT (SEQ ID No: 98) |

TABLE 6-6

| KP43 protease mutation | Mutation primer R | | Mutation primer F | |
|---|---|---|---|---|
| | Primer name | Sequence | Primer name | Sequence |
| K151F | K151_R | GCGCACATAGTCATCCACATTTCT (SEQ ID No: 99) | K151F_F | GATGACTATGTGCGCTTCAATGATATGACGATCCTT (SEQ ID No: 100) |
| N166F | N166_R | CGGTCCTTCATTCCCGGCAGCGAA (SEQ ID No: 101) | N166F_F | GGGAATGAAGGACCGTTCGGCGGAACCATCAGTGCA (SEQ ID No: 102) |
| N166I | N166_R | CGGTCCTTCATTCCCGGCAGCGAA (SEQ ID No: 101) | N166I_F | GGGAATGAAGGACCGATTGGCGGAACCATCAGTGCA (SEQ ID No: 103) |
| N166L | N166_R | CGGTCCTTCATTCCCGGCAGCGAA (SEQ ID No: 101) | N166L_F | GGGAATGAAGGACCGCTTGGCGGAACCATCAGTGCA (SEQ ID No: 104) |
| N166V | N166_R | CGGTCCTTCATTCCCGGCAGCGAA (SEQ ID No: 101) | N166V_F | GGGAATGAAGGACCGGTGGGCGGAACCATCAGTGCA (SEQ ID No: 105) |
| N166W | N166_R | CGGTCCTTCATTCCCGGCAGCGAA (SEQ ID No: 101) | N166W_F | GGGAATGAAGGACCGTGGGGCGGAACCATCAGTGCA (SEQ ID No: 106) |
| S191F | S191_R | TGGGCGGAGGTTTTCCGTAGCTCC (SEQ ID No: 107) | S191F_F | GAAAACCTCCGCCCATTCTTTGGGTCTTATGCGGAC (SEQ ID No: 108) |
| S191I | S191_R | TGGGCGGAGGTTTTCCGTAGCTCC (SEQ ID No: 107) | S191I_F | GAAAACCTCCGCCCAATTTTTGGGTCTTATGCGGAC (SEQ ID No: 109) |
| S191L | S191_R | TGGGCGGAGGTTTTCCGTAGCTCC (SEQ ID No: 107) | S191L_F | GAAAACCTCCGCCCACTTTTTGGGTCTTATGCGGAC (SEQ ID No: 110) |
| S191V | S191_R | TGGGCGGAGGTTTTCCGTAGCTCC (SEQ ID No: 107) | S191V_F | GAAAACCTCCGCCCAGTGTTTGGGTCTTATGCGGAC (SEQ ID No: 111) |
| S191W | S191_R | TGGGCGGAGGTTTTCCGTAGCTCC (SEQ ID No: 107) | S191W_F | GAAAACCTCCGCCCATGGTTTGGGTCTTATGCGGAC (SEQ ID No: 112) |
| S194Y | S194_R | CCCAAAGCTTGGGCGGAGGTTTTC (SEQ ID No: 113) | S194Y_F | CGCCCAAGCTTGGGTATTATGCGGACAATATCAAC (SEQ ID No: 114) |
| N200W | N200_R | GATATTGTCCGCATAAGACCCAAA (SEQ ID No: 115) | N200W_F | TATGCGGACAATATCTGGCATGTGGCACAGTTCTCT (SEQ ID No: 116) |
| Q204I | Q204_R | TGCCACATGGTTGATATTGTCCGC (SEQ ID No: 117) | Q204I_F | ATCAACCATGTGGCAATTTTCTCTTCACGTGGACCG (SEQ ID No: 118) |

TABLE 6-7

| KP43 protease mutation | Mutation primer R | | Mutation primer F | |
|---|---|---|---|---|
| | Primer name | Sequence | Primer name | Sequence |
| Q204L | Q204_R | TGCCACATGGTTGATATTGTCCGC (SEQ ID No: 117) | Q204L_F | ATCAACCATGTGGCACTTTTCTCTTCACGTGGACCG (SEQ ID No: 119) |
| Q204M | Q204_R | TGCCACATGGTTGATATTGTCCGC (SEQ ID No: 117) | Q204M_F | ATCAACCATGTGGCAATGTTCTCTTCACGTGGACCG (SEQ ID No: 120) |
| Q204V | Q204_R | TGCCACATGGTTGATATTGTCCGC (SEQ ID No: 117) | Q204V_F | ATCAACCATGTGGCAGTGTTCTCTTCACGTGGACCG (SEQ ID No: 121) |
| K212L | K212_R | TGTCGGTCCACGTGAAGAGAACTG (SEQ ID No: 122) | K212L_F | TCACGTGGACCGACACTTGATGGACGGATCAAACCG (SEQ ID No: 123) |
| K212V | K212_R | TGTCGGTCCACGTGAAGAGAACTG (SEQ ID No: 122) | K212V_F | TCACGTGGACCGACAGTGGATGGACGGATCAAACCG (SEQ ID No: 124) |
| K212W | K212_R | TGTCGGTCCACGTGAAGAGAACTG (SEQ ID No: 122) | K212W_F | TCACGTGGACCGACATGGGATGGACGGATCAAACCG (SEQ ID No: 125) |
| S233I | S233_R | AGATCTTGCTGATAGTATGAACGT (SEQ ID No: 126) | S233I_F | CTATCAGCAAGATCTATTCTTGCACCGGATTCCTCC (SEQ ID No: 127) |
| S233L | S233_R | AGATCTTGCTGATAGTATGAACGT (SEQ ID No: 126) | S233L_F | CTATCAGCAAGATCTCTTCTTGCACCGGATTCCTCC (SEQ ID No: 128) |
| S233W | S233_R | AGATCTTGCTGATAGTATGAACGT (SEQ ID No: 126) | S233W_F | CTATCAGCAAGATCTTGGCTTGCACCGGATTCCTCC (SEQ ID No: 129) |
| S238L | S238_R | ATCCGGTGCAAGAGAAGATCTTGC (SEQ ID No: 130) | S238L_F | TCTCTTGCACCGGATCTTTCCTTCTGGGCGAACCAT (SEQ ID No: 131) |
| N243I | N243_R | CGCCCAGAAGGAGGAATCCGGTGC (SEQ ID No: 132) | N243I_F | TCCTCCTTCTGGGCGATTCATGACAGTAAATATGCA (SEQ ID No: 133) |
| N243L | N243_R | CGCCCAGAAGGAGGAATCCGGTGC (SEQ ID No: 132) | N243L_F | TCCTCCTTCTGGGCGCTTCATGACAGTAAATATGCA (SEQ ID No: 134) |
| N243Y | N243_R | CGCCCAGAAGGAGGAATCCGGTGC (SEQ ID No: 132) | N243Y_F | TCCTCCTTCTGGGCGTATCATGACAGTAAATATGCA (SEQ ID No: 135) |
| S246F | S246_R | GTCATGGTTCGCCCAGAAGGAGGA (SEQ ID No: 136) | S246F_F | TGGGCGAACCATGACTTCAAATATGCATACATGGGT (SEQ ID No: 137) |

TABLE 6-8

| KP43 protease mutation | Mutation primer R | | Mutation primer F | |
|---|---|---|---|---|
| | Primer name | Sequence | Primer name | Sequence |
| S246L | S246_R | GTCATGGTTCGCCCAGAAGGAGGA (SEQ ID No: 136) | S246L_F | TGGGCGAACCATGACCTTAAATATGCATACATGGGT (SEQ ID No: 138) |
| S246V | S246_R | GTCATGGTTCGCCCAGAAGGAGGA (SEQ ID No: 136) | S246V_F | TGGGCGAACCATGACGTGAAATATGCATACATGGGT (SEQ ID No: 139) |
| S246W | S246_R | GTCATGGTTCGCCCAGAAGGAGGA (SEQ ID No: 136) | S246W_F | TGGGCGAACCATGACTGGAAATATGCATACATGGGT (SEQ ID No: 140) |
| S246Y | S246_R | GTCATGGTTCGCCCAGAAGGAGGA (SEQ ID No: 136) | S246Y_F | TGGGCGAACCATGACTATAAATATGCATACATGGGT (SEQ ID No: 141) |
| N275F | N275_R | TTTCACAAAATGCTCACGAAGCTG (SEQ ID No: 142) | N275F_F | GAGCATTTTGTGAAATTCAGAGGCATCACACCAAAG (SEQ ID No: 143) |
| N275L | N275_R | TTTCACAAAATGCTCACGAAGCTG (SEQ ID No: 142) | N275L_F | GAGCATTTTGTGAAACTTAGAGGCATCACACCAAAG (SEQ ID No: 144) |
| N275W | N275_R | TTTCACAAAATGCTCACGAAGCTG (SEQ ID No: 142) | N275W_F | GAGCATTTTGTGAAATGGAGAGGCATCACACCAAAG (SEQ ID No: 145) |
| G277F | G277_R | TCTGTTTTTCACAAAATGCTCACG (SEQ ID No: 146) | G277F_F | TTTGTGAAAAACAGATTCATCACACCAAAGCCTTCT (SEQ ID No: 147) |

TABLE 6-8-continued

| KP43 protease mutation | Mutation primer R | | Mutation primer F | |
|---|---|---|---|---|
| | Primer name | Sequence | Primer name | Sequence |
| G277I | G277_R | TCTGTTTTTCACAAAATGCTCACG (SEQ ID No: 146) | G277I_F | TTTGTGAAAAACAGAATTATCACACCAAAGCCTTCT (SEQ ID No: 148) |
| G277L | G277_R | TCTGTTTTTCACAAAATGCTCACG (SEQ ID No: 146) | G277L_F | TTTGTGAAAAACAGACTTATCACACCAAAGCCTTCT (SEQ ID No: 149) |
| G277V | G277_R | TCTGTTTTTCACAAAATGCTCACG (SEQ ID No: 146) | G277V_F | TTTGTGAAAAACAGAGTGATCACACCAAAGCCTTCT (SEQ ID No: 150) |
| G297F | G297_R | GATGTCAGCTGCACCGGCAATCAG (SEQ ID No: 151) | G297F_F | GGTGCAGCTGACATCTTCCTTGGCTACCCGAACGGT (SEQ ID No: 152) |
| G297L | G297_R | GATGTCAGCTGCACCGGCAATCAG (SEQ ID No: 151) | G297L_F | GGTGCAGCTGACATCCTTCTTGGCTACCCGAACGGT (SEQ ID No: 153) |
| G297W | G297_R | GATGTCAGCTGCACCGGCAATCAG (SEQ ID No: 151) | G297W_F | GGTGCAGCTGACATCTGGCTTGGCTACCCGAACGGT (SEQ ID No: 154) |

TABLE 6-9

| KP43 protease mutation | Mutation primer R | | Mutation primer F | |
|---|---|---|---|---|
| | Primer name | Sequence | Primer name | Sequence |
| S326W | S326_R | ACTGGACTCGTTCACATAGGCAAC (SEQ ID No: 155) | S326W_F | GTGAACGAGTCCAGTTGGCTATCCACCAGCCAAAAA (SEQ ID No: 156) |
| S330F | S330_R | GGTGGATAGAGAACTGGACTCGTT (SEQ ID No: 157) | S330F_F | AGTTCTCTATCCACCTTCCAAAAAGCGACGTACTCG (SEQ ID No: 158) |
| S330M | S330_R | GGTGGATAGAGAACTGGACTCGTT (SEQ ID No: 157) | S330M_F | AGTTCTCTATCCACCATGCAAAAAGCGACGTACTCG (SEQ ID No: 159) |
| S330W | S330_R | GGTGGATAGAGAACTGGACTCGTT (SEQ ID No: 157) | S330W_F | AGTTCTCTATCCACCTGGCAAAAAGCGACGTACTCG (SEQ ID No: 160) |
| K332G | K332_R | TTGGCTGGTGGATAGAGAACTGGA (SEQ ID No: 161) | K332G_F | CTATCCACCAGCCAAGGAGCGACGTACTCGTTTACT (SEQ ID No: 162) |
| K332T | K332_R | TTGGCTGGTGGATAGAGAACTGGA (SEQ ID No: 161) | K332T_F | CTATCCACCAGCCAAACAGCGACGTACTCGTTTACT (SEQ ID No: 163) |
| K332V | K332_R | TTGGCTGGTGGATAGAGAACTGGA (SEQ ID No: 161) | K332V_F | CTATCCACCAGCCAAGTGGCGACGTACTCGTTTACT (SEQ ID No: 164) |
| T334L | T334_R | CGCTTTTTGGCTGGTGGATAGAGA (SEQ ID No: 165) | T334L_F | ACCAGCCAAAAGCGCTTTACTCGTTTACTGCTACT (SEQ ID No: 166) |
| G342E | G342_R | GGCAGTAGCAGTAAACGAGTACGT (SEQ ID No: 167) | G342E_F | TTTACTGCTACTGCCGAAAAGCCTTTGAAAATCTCC (SEQ ID No: 168) |
| G342L | G342_R | GGCAGTAGCAGTAAACGAGTACGT (SEQ ID No: 167) | G342L_F | TTTACTGCTACTGCCCTTAAGCCTTTGAAAATCTCC (SEQ ID No: 169) |
| G342T | G342_R | GGCAGTAGCAGTAAACGAGTACGT (SEQ ID No: 167) | G342T_F | TTTACTGCTACTGCCACAAAGCCTTTGAAAATCTCC (SEQ ID No: 170) |
| G342W | G342_R | GGCAGTAGCAGTAAACGAGTACGT (SEQ ID No: 167) | G342W_F | TTTACTGCTACTGCCTGGAAGCCTTTGAAAATCTCC (SEQ ID No: 171) |
| K343T | K343_R | GCCGGCAGTAGCAGTAAACGAGTA (SEQ ID No: 172) | K343T_F | ACTGCTACTGCCGGCACACCTTTGAAAATCTCCCTG (SEQ ID No: 173) |
| S357L | S357_R | CGCAGGGGCATCAGACCATACCAG (SEQ ID No: 174) | S357L_F | TCTGATGCCCCTGCGCTTACAACTGCTTCCGTAACG (SEQ ID No: 175) |

TABLE 6-10

| KP43 protease mutation | Mutation primer R | | Mutation primer F | |
|---|---|---|---|---|
| | Primer name | Sequence | Primer name | Sequence |
| T359F | T359_R | TGTGCTCGCAGGGGCATCAGACCA (SEQ ID No: 176) | T359F_F | GCCCCTGCGAGCACATTCGCTTCCGTAACGCTTGTC (SEQ ID No: 177) |
| T359G | T359_R | TGTGCTCGCAGGGGCATCAGACCA (SEQ ID No: 176) | T359G_F | GCCCCTGCGAGCACAGGAGCTTCCGTAACGCTTGTC (SEQ ID No: 178) |
| T359I | T359_R | TGTGCTCGCAGGGGCATCAGACCA (SEQ ID No: 176) | T359I_F | GCCCCTGCGAGCACAATTGCTTCCGTAACGCTTGTC (SEQ ID No: 179) |
| T359L | T359_R | TGTGCTCGCAGGGGCATCAGACCA (SEQ ID No: 176) | T359L_F | GCCCCTGCGAGCACACTTGCTTCCGTAACGCTTGTC (SEQ ID No: 180) |
| S361I | S361_R | AGCAGTTGTGCTCGCAGGGGCATC (SEQ ID No: 181) | S361I_F | GCGAGCACAACTGCTATTGTAACGCTTGTCAATGAT (SEQ ID No: 182) |
| S361V | S361_R | AGCAGTTGTGCTCGCAGGGGCATC (SEQ ID No: 181) | S361V_F | GCGAGCACAACTGCTGTGGTAACGCTTGTCAATGAT (SEQ ID No: 183) |
| S361W | S361_R | AGCAGTTGTGCTCGCAGGGGCATC (SEQ ID No: 181) | S361W_F | GCGAGCACAACTGCTTGGGTAACGCTTGTCAATGAT (SEQ ID No: 184) |
| N376W | N376_R | TGGAGCGGTAATGACAAGGTCCAG (SEQ ID No: 185) | N376W_F | GTCATTACCGCTCCATGGGGCACACAGTATGTAGGA (SEQ ID No: 186) |
| T378L | T378_R | GCCATTTGGAGCGGTAATGACAAG (SEQ ID No: 187) | T378L_F | ACCGCTCCAAATGGCCTTCAGTATGTAGGAAATGAC (SEQ ID No: 188) |
| T378W | T378_R | GCCATTTGGAGCGGTAATGACAAG (SEQ ID No: 187) | T378W_F | ACCGCTCCAAATGGCTGGCAGTATGTAGGAAATGAC (SEQ ID No: 189) |
| F385M | F385_R | GTCATTTCCTACATACTGTGTGCC (SEQ ID No: 190) | F385M_F | TATGTAGGAAATGACATGACTTCGCCATACAATGAT (SEQ ID No: 191) |
| F385P | F385_R | GTCATTTCCTACATACTGTGTGCC (SEQ ID No: 190) | F385P_F | TATGTAGGAAATGACCCAACTTCGCCATACAATGAT (SEQ ID No: 192) |
| F385Y | F385_R | GTCATTTCCTACATACTGTGTGCC (SEQ ID No: 190) | F385Y_F | TATGTAGGAAATGACTATACTTCGCCATACAATGAT (SEQ ID No: 193) |
| T386A | T386_R | AAAGTCATTTCCTACATACTGTGT (SEQ ID No: 194) | T386A_F | GTAGGAAATGACTTTGCATCGCCATACAATGATAAC (SEQ ID No: 195) |

TABLE 6-11

| KP43 protease mutation | Mutation primer R | | Mutation primer F | |
|---|---|---|---|---|
| | Primer name | Sequence | Primer name | Sequence |
| T386I | T386_R | AAAGTCATTTCCTACATACTGTGT (SEQ ID No: 194) | T386I_F | GTAGGAAATGACTTTATTTCGCCATACAATGATAAC (SEQ ID No: 196) |
| T386L | T386_R | AAAGTCATTTCCTACATACTGTGT (SEQ ID No: 194) | T386L_F | GTAGGAAATGACTTTCTTTCGCCATACAATGATAAC (SEQ ID No: 197) |
| T386M | T386_R | AAAGTCATTTCCTACATACTGTGT (SEQ ID No: 194) | T386M_F | GTAGGAAATGACTTTATGTCGCCATACAATGATAAC (SEQ ID No: 198) |
| S387F | S387_R | AGTAAAGTCATTTCCTACATACTG (SEQ ID No: 199) | S387F_F | GGAAATGACTTTACTTTCCCATACAATGATAACTGG (SEQ ID No: 200) |
| S387G | S387_R | AGTAAAGTCATTTCCTACATACTG (SEQ ID No: 199) | S387G_F | GGAAATGACTTTACTGGACCATACAATGATAACTGG (SEQ ID No: 201) |
| S387I | S387_R | AGTAAAGTCATTTCCTACATACTG (SEQ ID No: 199) | S387I_F | GGAAATGACTTTACTATTCCATACAATGATAACTGG (SEQ ID No: 202) |
| S387L | S387_R | AGTAAAGTCATTTCCTACATACTG (SEQ ID No: 199) | S387L_F | GGAAATGACTTTACTCTTCCATACAATGATAACTGG (SEQ ID No: 203) |
| S387M | S387_R | AGTAAAGTCATTTCCTACATACTG (SEQ ID No: 199) | S387M_F | GGAAATGACTTTACTATGCCATACAATGATAACTGG (SEQ ID No: 204) |

TABLE 6-11-continued

| KP43 protease mutation | Mutation primer R | | Mutation primer F | |
|---|---|---|---|---|
| | Primer name | Sequence | Primer name | Sequence |
| S387V | S387_R | AGTAAAGTCATTTCCTACATACTG (SEQ ID No: 199) | S387V_F | GGAAATGACTTTACTGTGCCATACAATGATAACTGG (SEQ ID No: 205) |
| S387W | S387_R | AGTAAAGTCATTTCCTACATACTG (SEQ ID No: 199) | S387W_F | GGAAATGACTTTACTTGGCCATACAATGATAACTGG (SEQ ID No: 206) |
| N390F | N390_R | GTATGGCGAAGTAAAGTCATTTCC (SEQ ID No: 207) | N390F_F | TTTACTTCGCCATACTTCGATAACTGGGATGGCCGC (SEQ ID No: 208) |
| N390G | N390_R | GTATGGCGAAGTAAAGTCATTTCC (SEQ ID No: 207) | N390G_F | TTTACTTCGCCATACGGAGATAACTGGGATGGCCGC (SEQ ID No: 209) |
| N390S | N390_R | GTATGGCGAAGTAAAGTCATTTCC (SEQ ID No: 207) | N390S_F | TTTACTTCGCCATACTCCGATAACTGGGATGGCCGC (SEQ ID No: 210) |
| N390T | N390_R | GTATGGCGAAGTAAAGTCATTTCC (SEQ ID No: 207) | N390T_F | TTTACTTCGCCATACACAGATAACTGGGATGGCCGC (SEQ ID No: 211) |

TABLE 6-12

| KP43 protease mutation | Mutation primer R | | Mutation primer F | |
|---|---|---|---|---|
| | Primer name | Sequence | Primer name | Sequence |
| N390Y | N390_R | GTATGGCGAAGTAAAGTCATTTCC (SEQ ID No: 207) | N390Y_F | TTTACTTCGCCATACTATGATAACTGGGATGGCCGC (SEQ ID No: 212) |
| W393Q | W393_R | GTTATCATTGTATGGCGAAGTAAA (SEQ ID No: 213) | W393Q_F | CCATACAATGATAACCAGGATGGCCGCAATAACGTA (SEQ ID No: 214) |
| R396G | R396_R | GCCATCCCAGTTATCATTGTATGG (SEQ ID No: 215) | R396G_F | GATAACTGGGATGGCGGAAATAACGTAGAAAATGTA (SEQ ID No: 216) |
| F403K | F403_R | TACATTTTCTACGTTATTGCGGCC (SEQ ID No: 217) | F403K_F | AACGTAGAAAATGTAAAAATTAATGCACCACAAAGC (SEQ ID No: 218) |
| F403T | F403_R | TACATTTTCTACGTTATTGCGGCC (SEQ ID No: 217) | F403T_F | AACGTAGAAAATGTAACAATTAATGCACCACAAAGC (SEQ ID No: 219) |
| N405F | N405_R | AATAAATACATTTTCTACGTTATT (SEQ ID No: 217) | N405F_F | GAAAATGTATTTATTTTCGCACCACAAAGCGGGACG (SEQ ID No: 220) |
| N405I | N405_R | AATAAATACATTTTCTACGTTATT (SEQ ID No: 217) | N405I_F | GAAAATGTATTTATTATTGCACCACAAAGCGGGACG (SEQ ID No: 221) |
| N405L | N405_R | AATAAATACATTTTCTACGTTATT (SEQ ID No: 217) | N405L_F | GAAAATGTATTTATTCTTGCACCACAAAGCGGGACG (SEQ ID No: 222) |
| N405P | N405_R | AATAAATACATTTTCTACGTTATT (SEQ ID No: 217) | N405P_F | GAAAATGTATTTATTCCAGCACCACAAAGCGGGACG (SEQ ID No: 223) |
| N405V | N405_R | AATAAATACATTTTCTACGTTATT (SEQ ID No: 217) | N405V_F | GAAAATGTATTTATTGTGGCACCACAAAGCGGGACG (SEQ ID No: 224) |
| N405W | N405_R | AATAAATACATTTTCTACGTTATT (SEQ ID No: 217) | N405W_F | GAAAATGTATTTATTTGGGCACCACAAAGCGGGACG (SEQ ID No: 225) |
| A406F | A406_R | ATTAATAAATACATTTTCTACGTT (SEQ ID No: 226) | A406F_F | AATGTATTTATTAATTTCCCACAAAGCGGGACGTAT (SEQ ID No: 227) |
| A406V | A406_R | ATTAATAAATACATTTTCTACGTT (SEQ ID No: 226) | A406V_F | AATGTATTTATTAATGTGCCACAAAGCGGGACGTAT (SEQ ID No: 228) |
| A406W | A406_R | ATTAATAAATACATTTTCTACGTT (SEQ ID No: 226) | A406W_F | AATGTATTTATTAATTGGCCACAAAGCGGGACGTAT (SEQ ID No: 229) |

TABLE 6-13

| KP43 protease mutation | Mutation primer R | | Mutation primer F | |
|---|---|---|---|---|
| | Primer name | Sequence | Primer name | Sequence |
| P407C | P407_R | TGCATTAATAAATACATTTTCTAC (SEQ ID No: 230) | P407C_F | GTATTTATTAATGCATGCCAAAGCGGGACGTATACA (SEQ ID No: 231) |
| P407G | P407_R | TGCATTAATAAATACATTTTCTAC (SEQ ID No: 230) | P407G_F | GTATTTATTAATGCAGGACAAAGCGGGACGTATACA (SEQ ID No: 232) |
| Q408I | Q408_R | TGGTGCATTAATAAATACATTTTC (SEQ ID No: 233) | Q408I_F | TTTATTAATGCACCAATTAGCGGGACGTATACAATT (SEQ ID No: 234) |
| Q408N | Q408_R | TGGTGCATTAATAAATACATTTTC (SEQ ID No: 233) | Q408N_F | TTTATTAATGCACCAAATAGCGGGACGTATACAATT (SEQ ID No: 235) |
| Q408W | Q408_R | TGGTGCATTAATAAATACATTTTC (SEQ ID No: 233) | Q408W_F | TTTATTAATGCACCATGGAGCGGGACGTATACAATT (SEQ ID No: 236) |
| Q408Y | Q408_R | TGGTGCATTAATAAATACATTTTC (SEQ ID No: 233) | Q408Y_F | TTTATTAATGCACCATATAGCGGGACGTATACAATT (SEQ ID No: 237) |
| S409W | S409_R | TTGTGGTGCATTAATAAATACATT (SEQ ID No: 233) | S409W_F | ATTAATGCACCACAATGGGGACGTATACAATTGAG (SEQ ID No: 238) |
| S409Y | S409_R | TTGTGGTGCATTAATAAATACATT (SEQ ID No: 239) | S409Y_F | ATTAATGCACCACAATATGGGACGTATACAATTGAG (SEQ ID No: 240) |
| T411A | T411_R | CCCGCTTTGTGGTGCATTAATAAA (SEQ ID No: 241) | T411A_F | GCACCACAAAGCGGGGCATATACAATTGAGGTACAG (SEQ ID No: 242) |
| T411L | T411_R | CCCGCTTTGTGGTGCATTAATAAA (SEQ ID No: 241) | T411L_F | GCACCACAAAGCGGGCTTTATACAATTGAGGTACAG (SEQ ID No: 243) |
| T411P | T411_R | CCCGCTTTGTGGTGCATTAATAAA (SEQ ID No: 241) | T411P_F | GCACCACAAAGCGGGCCATATACAATTGAGGTACAG (SEQ ID No: 244) |
| T411V | T411_R | CCCGCTTTGTGGTGCATTAATAAA (SEQ ID No: 241) | T411V_F | GCACCACAAAGCGGGGTGTATACAATTGAGGTACAG (SEQ ID No: 245) |
| T427V | T427_R | CTGTGGTCCAACCGGTACGTTATA (SEQ ID No: 246) | T427V_F | CCGGTTGGACCACAGGTGTTCTCGTTGGCAATTGTG (SEQ ID No: 247) |
| V433L | V433_R | AATTGCCAACGAGAAGGTCTGTGG (SEQ ID No: 248) | V433L_F | TTCTCGTTGGCAATTCTTAATTAATAGAATAACAGA (SEQ ID No: 249) |

Example 2

Evaluation of Solubility of Mutant Alkaline Protease

The concentration of a protein of the mutant alkaline protease in the culture supernatant obtained in Example 1 was obtained in accordance with the method described in Reference Example 2 (1) (described later). Furthermore, in accordance with the method described in Reference Example 2 (2) (described later), the turbidity of composition C in which the culture supernatant was added in a predetermined amount was measured. From the turbidity, a relative turbidity (%) was obtained. For each alkaline protease mutant, relative turbidity values (N=3 or more) were obtained, averaged and used as the relative turbidity of each mutant alkaline protease.

The results are shown in Table 7. Each of the mutant alkaline protease shows that a relative turbidity to the parent alkaline protease (WT) is 95% or less, demonstrating improvement of solubility.

TABLE 7

| Mutant | Relative turbidity (%) |
|---|---|
| D11G | 79.8 |
| D11N | 83.6 |
| D11S | 93.6 |
| S16I | 81.2 |
| S16L | 88.6 |
| S16V | 93.6 |
| S16W | 79.4 |
| Y20A | 71.8 |
| Q22W | 86.5 |
| G23N | 89.8 |
| R37T | 84.5 |
| S40F | 86.9 |
| S40I | 81.5 |
| S40L | 80.9 |
| S40V | 81.6 |
| S40W | 49.8 |
| S41I | 79.3 |
| A52G | 76.4 |
| A52S | 88.5 |
| L53A | 75.5 |
| L53I | 94.9 |
| L53V | 69.1 |
| L56V | 76.7 |
| T59F | 70.9 |

TABLE 7-continued

| Mutant | Relative turbidity (%) |
|---|---|
| T59I | 69.4 |
| T59L | 68.3 |
| T59M | 69.8 |
| T59V | 89.3 |
| T59W | 58.2 |
| N60F | 73.0 |
| N60I | 70.0 |
| N60L | 63.1 |
| N60V | 74.0 |
| N60W | 77.0 |
| N63D | 89.7 |
| N63L | 75.0 |
| G80A | 79.2 |
| G80H | 91.4 |
| S81F | 82.3 |
| S81I | 83.8 |
| S81L | 83.5 |
| S81Q | 86.1 |
| S81W | 76.4 |
| S81Y | 93.7 |
| T82Q | 85.0 |
| N91C | 89.3 |
| S100F | 68.5 |
| S100I | 62.3 |
| S100L | 68.5 |
| S100W | 75.8 |
| G101F | 69.0 |
| G101I | 72.7 |
| G101L | 68.4 |
| G101V | 74.3 |
| G101W | 56.8 |
| G101Y | 86.0 |
| S109F | 65.7 |
| S109I | 71.6 |
| S109L | 82.6 |
| T113L | 85.1 |
| T113W | 71.3 |
| S120F | 84.0 |
| S120I | 93.7 |
| S120W | 76.5 |
| S120Y | 91.9 |
| N135L | 94.7 |
| T140F | 93.5 |
| T140L | 89.2 |
| T140W | 82.9 |
| K151F | 93.0 |
| N166F | 80.4 |
| N166I | 93.1 |
| N166L | 82.3 |
| N166V | 94.7 |
| N166W | 78.2 |
| S191F | 90.6 |
| S191I | 82.4 |
| S191L | 88.2 |
| S191V | 81.6 |
| S191W | 91.7 |
| S194Y | 87.4 |
| N200W | 84.3 |
| Q204I | 80.1 |
| Q204L | 94.9 |
| Q204M | 82.3 |
| Q204V | 89.5 |
| K212L | 94.2 |
| K212V | 94.0 |
| K212W | 86.8 |
| S233I | 94.3 |
| S233L | 81.9 |
| S233W | 71.4 |
| S238L | 85.9 |
| N243I | 88.5 |
| N243L | 80.8 |
| N243Y | 80.0 |
| S246F | 88.5 |
| S246L | 85.2 |
| S246V | 89.6 |
| S246W | 74.5 |
| S246Y | 92.5 |
| N275F | 87.3 |
| N275L | 92.5 |
| N275W | 82.1 |
| G277F | 83.2 |
| G277I | 91.9 |
| G277L | 84.3 |
| G277V | 92.9 |
| G297F | 75.3 |
| G297L | 78.3 |
| G297W | 69.3 |
| S326W | 95.0 |
| S330F | 92.5 |
| S330M | 85.4 |
| S330W | 88.1 |
| K332G | 90.9 |
| K332T | 90.6 |
| K332V | 92.9 |
| T334L | 85.7 |
| G342E | 85.4 |
| G342L | 81.2 |
| G342T | 90.2 |
| G342W | 77.7 |
| K343T | 75.4 |
| S357L | 84.4 |
| T359F | 76.0 |
| T359G | 74.7 |
| T359I | 85.2 |
| T359L | 84.0 |
| S361I | 77.2 |
| S361V | 84.2 |
| S361W | 60.3 |
| N376W | 52.9 |
| T378L | 79.6 |
| T378W | 68.4 |
| F385M | 94.0 |
| F385P | 75.8 |
| F385Y | 78.8 |
| T386A | 80.4 |
| T386I | 78.2 |
| T386L | 93.8 |
| T386M | 78.2 |
| S387F | 83.7 |
| S387G | 85.9 |
| S387I | 91.5 |
| S387L | 79.7 |
| S387M | 84.9 |
| S387V | 76.1 |
| S387W | 85.0 |
| N390F | 75.3 |
| N390G | 87.9 |
| N390S | 75.1 |
| N390T | 90.4 |
| N390Y | 72.7 |
| W393Q | 84.3 |
| R396G | 70.2 |
| F403K | 93.2 |
| F403T | 80.0 |
| N405F | 84.8 |
| N405I | 80.1 |
| N405L | 82.8 |
| N405P | 78.2 |
| N405V | 86.9 |
| N405W | 76.0 |
| A406F | 94.7 |
| A406V | 86.2 |
| A406W | 86.8 |
| P407C | 82.2 |
| P407G | 88.2 |
| Q408I | 83.8 |
| Q408N | 94.3 |
| Q408W | 90.1 |
| Q408Y | 94.0 |
| S409W | 69.5 |
| S409Y | 87.8 |
| T411A | 82.6 |

TABLE 7-continued

| Mutant | Relative turbidity (%) |
|---|---|
| T411L | 93.5 |
| T411P | 85.1 |
| T411V | 81.0 |
| T427V | 92.4 |
| V433L | 72.1 |

Example 3

Evaluation of Solubility of Multiple Mutant

Mutations for improving solubility found in Example 2 were multiplexed and the effect of thus-obtained multiple mutant was evaluated. To explain more specifically, a plasmid was extracted from a host bacterium producing a protease mutant exhibiting an improved solubility in Example 2. Using this plasmid as a template, another mutation for improving solubility found in Example 2 was introduced in the same manner as in Example 1 to form a double mutant. Furthermore, a plasmid was extracted from the host bacterium producing the double mutant. Using this plasmid as a template, the same procedure was repeated to prepare a triple mutant. With respect to a double mutant and a triple mutant, relative turbidity (%) (average value of N=3 or more) to the parent alkaline protease (WT) was obtained in the same procedure as in Example 2. The results are shown in Table 8.

TABLE 8

| Mutant | Relative turbidity (%) |
|---|---|
| T59L | 68 |
| T59L/S40L | 28 |
| T59L/S40L/N405W | 19 |
| T59L/S40L/S191V | 17 |
| T59L/S40L/S81W | 14 |
| T59L/S40L/S81L | 12 |
| T59L/N405L | 47 |
| T59L/N405L/S81L | 30 |
| T59L/N405L/S191L | 28 |
| T59L/N405L/S40L | 25 |
| T59L/S191L | 28 |
| T59L/S191L/S40L | 21 |
| T59L/S191L/S81W | 21 |
| T59L/S191L/S81L | 16 |
| WT | 100 |

Example 4

Evaluation of Solubility of Multiple Mutants to Commercially Available Concentrated Liquid Detergent As the solubility of the multiple mutant constructed in Example 3 to each of the commercially available concentrated liquid detergents [composition A; Attack Neo (Kao Corp.) and composition B; NANOX (lion), each composition is shown in Table 9], the relative turbidity (%) (average value of N=3 or more) to the parent alkaline protease (WT) was obtained in the same manner as in Example 2. The commercially available detergents were used for evaluation after inactivation of washing enzymes at 70° C. for 8 hours. The results are shown in Table 10.

TABLE 9

| Concentrated liquid detergent | Liquid property | composition |
|---|---|---|
| Composition A | Weak alkali | Surfactant [74%, higher alcohol base (nonion), straight alkyl benzene base, fatty acid base (anion)], stabilizer (butyl carbitol), alkali agent, dispersant, enzyme |
| Composition B | Neutral | Surfactant (55% polyoxyethylene fatty acid methyl ester), stabilizer, alkali agent, enzyme |

TABLE 10

| | Relative turbidity (%) | |
|---|---|---|
| Mutant | Composition A | Composition B |
| T59L/S81W/191V | 23.5 | 38.9 |
| T59L/S81W/191L | 24.7 | 35.8 |
| T59L/S81L/405L | 19.5 | 28.9 |
| T59L/S81L/191V | 36.6 | 32.1 |
| T59L/S81L/191L | 20.5 | 29.2 |
| T59L/S40L/81W | 22.5 | 29.1 |
| T59L/S40L/405W | 24.9 | 34.6 |
| T59L/S40L/405L | 28.4 | 34.4 |
| T59L/S40L/191V | 22.9 | 32.5 |
| T59L/S40L/191L | 22.8 | 29.7 |
| T59L/S191L/405W | 29.3 | 44.6 |
| T59L/S191L/405L | 22.5 | 33.4 |
| WT | 100 | 100 |

Example 5

Evaluation of Solubility of a Mutant Alkaline Protease Derived from Mutant KP43 Protease as a Parent Protease Referring to the descriptions of JP-A-2002-218989, JPA-2002-303176, JP-A-2004-000122, JP-A-2004-35176 and JP-A-2006-129865, the following mutations were successively introduced into KP43 protease (SEQ ID No: 2) to prepare a KP43 protease mutant (SEQ ID No: 250):

Tyrosine at position 195 was substituted with glutamine (JP-A-2002-218989);

Aspartic acid at position 369 was substituted with asparagine (JP-A-2002-303176);

Threonine at position 65 was substituted with proline, valine at position 273 with isoleucine, threonine at position 359 with serine and serine at position 387 with alanine (JP-A-2004-000122);

Asparagine at position 166 was substituted with glycine, and glycine at position 167 with valine (JP-A-2004-35176);

Alanine at position 133 was substituted with serine, valine at position 134 with threonine and serine was inserted between position 133 and position 134 (JP-A-2006-129865).

The amino acid sequence of a KP43 protease mutant (SEQ ID No: 250) having these mutations introduced therein has an identity of 97.5% to wild type KP43; WT.

Using the above-mentioned mutant KP43 protease (mKP43) as a parent, a mutant which has improved solubility was prepared in the same manner as in Example 1. More specifically, a mutation primer for the parent protease was designed and prepared. Using these primers, a mutation was introduced in the same manner as in Example 1 to prepare the mutant alkaline protease. With respect to the obtained alkaline protease mutant, a relative turbidity (%) (average value of N=3 or more) to the parent alkaline protease (mKP43) was obtained in the same procedure as in Example 2 and the solubility in a liquid detergent was evaluated.

The results are shown in Table 11. In the case of mutant KP43 protease (mKP43) used as a parent, the same effect of increasing solubility of the mutant alkaline protease in a liquid detergent as in the case of wild type KP43 protease used as a parent, was confirmed.

TABLE 11

| Mutant | Relative turbidity (%) |
|---|---|
| D11G | 84.2 |
| D11N | 93.5 |
| D11S | 72.5 |
| S16V | 79.9 |
| S16W | 84.1 |
| Y20A | 87.9 |
| Q22W | 84.4 |
| G23N | 60.6 |
| R37T | 75.1 |
| S40F | 71.1 |
| S40I | 78.0 |
| S40L | 73.2 |
| S40W | 87.5 |
| S41I | 92.1 |
| A52G | 74.0 |
| A52S | 85.5 |
| L53A | 90.4 |
| L53I | 86.8 |
| L53V | 93.0 |
| L56V | 76.3 |
| T59F | 80.3 |
| T59I | 89.3 |
| T59L | 89.9 |
| T59M | 78.6 |
| T59V | 69.9 |
| N60F | 88.4 |
| N60I | 93.1 |
| N60L | 88.0 |
| N60W | 83.7 |
| N63D | 85.2 |
| N63L | 94.6 |
| G80A | 97.1 |
| G80H | 68.5 |
| S81F | 63.0 |
| S81Q | 66.5 |
| S81W | 52.4 |
| S81Y | 90.8 |
| T82Q | 84.5 |
| N91C | 88.4 |
| S191F | 80.7 |
| S194Y | 67.9 |
| N200W | 80.1 |
| Q204I | 75.3 |
| Q204L | 74.9 |
| Q204M | 78.9 |
| Q204V | 93.5 |
| S326W | 70.3 |
| S330F | 84.0 |
| S330M | 90.4 |
| S330W | 68.2 |
| K332G | 86.9 |
| K332R | 74.0 |
| K332T | 73.3 |
| K332V | 64.4 |
| T334L | 73.7 |
| T334R | 76.1 |
| G342E | 94.3 |
| G342L | 98.1 |
| G342T | 95.4 |
| G342W | 83.8 |
| K343T | 82.0 |

TABLE 11-continued

| Mutant | Relative turbidity (%) |
|---|---|
| S357L | 94.8 |
| T359G | 93.6 |
| S361W | 77.5 |
| N376W | 53.3 |
| F385M | 75.2 |
| F385P | 74.7 |
| F385R | 70.0 |
| F385Y | 89.6 |
| T386A | 59.8 |
| T386I | 73.2 |
| T386L | 77.2 |
| T386M | 85.9 |
| S387F | 73.8 |
| S387G | 91.0 |
| S387I | 77.4 |
| S387L | 72.9 |
| S387M | 86.5 |
| S387W | 58.3 |
| N390F | 74.1 |
| N390G | 93.1 |
| N390S | 88.3 |
| N390T | 72.3 |
| N390Y | 73.8 |
| W393Q | 60.4 |
| R396G | 91.2 |
| F403K | 79.9 |
| F403R | 82.9 |
| F403T | 88.4 |
| N405F | 69.5 |
| N405V | 68.8 |
| N405W | 43.1 |
| A406W | 52.1 |
| P407C | 92.6 |
| Q408I | 74.7 |
| Q408N | 60.6 |
| Q408W | 76.1 |
| Q408Y | 90.3 |
| S409Y | 73.5 |
| T411A | 74.2 |
| T411L | 87.7 |
| T411P | 83.1 |
| T411V | 84.2 |
| T427V | 77.0 |
| V433L | 73.4 |

Example 6

Evaluation of Solubility of Alkaline Protease Multiple Mutant Derived from Mutant KP43 Protease (mKP43) as a Parent Protease Mutations for improving solubility found in Example 2 and Example 5 were used in combination and the solubility improving effect was evaluated. To explain more specifically, a single mutant, a double mutant, a triple mutant, a tetra mutant and a penta mutant as shown in Table 12 were prepared by using the mutant KP43 protease (mKP43, SEQ ID No: 250) prepared in Example 5 as a parent alkaline protease in the same procedure as in Example 3. The relative turbidity (%) (average value of N=2 or more) of each mutant to the parent alkaline protease was obtained in the same procedure as in Example 2. The results are shown in Table 12.

TABLE 12

| Mutant | Relative turbidity (%) |
|---|---|
| N405L | 74.6 |
| N405L/T59V | 61.8 |
| N405L/T59I/S40F | 26.6 |
| N405L/T59I/S40I | 29.3 |
| N405L/T59I/S81W | 14.9 |
| N405L/T59V/S40F | 24.8 |
| N405L/T59V/S40I | 31.3 |
| N405L/T59V/S81W | 21.1 |
| N405W/S40F/T59I | 21.9 |
| N405W/S40F/T59V | 30.1 |
| N405W/S40I/T59I | 21.8 |
| N405W/S40I/T59V | 22.0 |
| N405L/T59I/S40F/S191L | 10.5 |
| N405L/T59V/S40I/S81L | 8.6 |
| N405L/T59V/S40I/S81Y | 11.0 |
| N405L/T59V/S40I/S191L | 10.1 |
| N405W/T59I/S40F/S191L | 10.9 |
| N405W/T59I/S40I/S191L | 7.9 |
| N405L/T59V/S40I/S191L/S81L | 6.7 |
| N405L/T59V/S40I/S191L/S81P | 10.2 |
| N405L/T59V/S40I/S191L/S81Y | 7.8 |

Example 7

Evaluation of Solubility of Alkaline Protease Multiple Mutant Derived from Mutant KP43 Protease (mKP43) as a Parent Protease by Acceleration Test The multiple mutants derived from the mutant KP43 protease (SEQ ID No: 250) prepared in Example 6 were subjected to an accelerated precipitation formation test by using a liquid detergent in a volume closer to practical use conditions. To explain more specifically, 9 mL of a liquid detergent (for example, the aforementioned composition C; described in Example 3 of JP-A-2010-275468) was put into a glass bottle (Maruemu screw tube No. 5), further, an appropriately diluted alkaline protease multiple mutant was added so as to obtain a final concentration of 0.2 to 0.4 g/L, sufficiently stirred, closed airtight and stored at 40° C. or 50° C. Every week, presence or absence of a precipitation at the bottom of the bottle was checked. The results are shown in Table 13.

TABLE 13

| Mutant | Storage conditions | Final concentration (protein amount in g/L of liquid detergent) | | | | |
|---|---|---|---|---|---|---|
| | | 0.2 | 0.25 | 0.3 | 0.35 | 0.4 |
| N405L/T59V/S40I/S191L | 40° C. 2 weeks | n/o | n/o | n/o | n/o | n/o |
| | 50° C. 2 weeks | n/o | n/o | n/o | o | o |
| N405L/T59V/S40I/S191L/S81L | 40° C. 4 weeks | n/o | n/o | n/o | n/o | n/o |
| | 50° C. 4 weeks | n/o | n/o | n/o | n/o | n/o | o: Precipitation was visually observed
n/o: Precipitation was not visually observed

Example 8

Evaluation of Detergency of Alkaline Protease Multiple Mutant Derived from Mutant KP43 Protease (mKP43) as a Parent Protease The multiple mutants prepared in Example 6 derived from the mutant KP43 protease (mKP43, SEQ ID No: 250) as a parent alkaline protease were evaluated for detergency. Detergency evaluation was performed by a Tergot-O-Meter (manufactured by Ueshima Seisakusho Co., Ltd.). A liquid detergent (for example, the aforementioned composition C described in Example 3 of JP-A-2010-275468)(350 μL) was added to service-water (1 L) to obtain a washing liquid. To this, an enzyme was added so as to obtain a final concentration of 0.0716 mg/L. Subsequently, stained cloth EMPA117 (manufactured by EMPA, blood/milk/carbon), which was previously cut into pieces of 6×6 cm squares, was added and washed (80 rpm) at 20° C. After the stained-cloth pieces were rinsed with service-water and lightness thereof was measured by a color-difference meter (MINOLTA, CM3500d). Based on a change of lightness before and after washing, the washing ratio was calculated (the following formula).

Washing ratio (%)=(L2−L1)/(L0−L1)×100

L0: lightness of original stained cloth
L1: lightness of the stained cloth before washing
L2: lightness of the stained cloth after washing The relative washing ratio is the washing ratio with a mutant based on the washing ratio of the parent alkaline protease regarded as 100. The results are shown in Table 14. Each mutant prepared in the Example 6 exhibits washing ratio equivalent to that of the parent alkaline protease.

TABLE 14

| Mutant | Relative washing ratio (%) |
|---|---|
| Parent mutant alkaline protease (mKP43) | 100.0 |
| N405L/T59V/S40I/S191L | 97.7 |
| N405L/T59V/S40I/S191L/S81L | 101.7 |
| N405L/T59V/S40I/S191L/S81P | 95.7 |
| N405L/T59V/S40I/S191L/S81Y | 94.9 |

Reference Example 1

Method for Preparing Enzyme

A method for preparing an enzyme, which is to be subjected to evaluation of its solubility in a liquid detergent, from e.g., wild type KP43 protease will be described below.

(1) Preparation of Gene Insertion/Expression Vector

Using a commercially available shuttle vector, pHY300PLK (manufactured by Takara Bio Inc.) as a template, a primer pHY+1 (HindIII) F (ggggAAGCTTCTAGA-GATCTGCAGGTCGACGG: SEQ ID No: 251) and a primer pHY+3040 (HindIII) R (ggggaagcttAAGG-TAAAGGATAAAACAGCACAATTCCAAG: SEQ ID No: 252), PCR amplification was performed by means of a PrimeSTAR Mutagenesis basal kit (manufactured by Takara Bio Inc.). The amplified product was digested with a restriction enzyme, HindIII (Roche), intramolecular cyclization was performed by use of Ligation High (manufactured by Toyobo Co., Ltd.) and purification was made through ethanol precipitation. A host bacterium, Bacillus sp. KSM-9865 strain (FERM P-18566) was transformed with this in accordance with an electroporation method and smeared onto a skim milk-containing alkali LB agar medium (containing 1% Bacto tryptone, 0.5% yeast extract, 1% sodium chloride, 1% skim milk, 1.5% agar, 0.05% sodium carbonate and 15 ppm tetracycline). Several days later, colonies formed in the agar medium were separated as a transformant and a plasmid was extracted. The sequence of the full-length plasmid was analyzed by using a DNA sequencer Prism 3100 (manufactured by ABI) to confirm that an unwanted mutation was not introduced by PCR error. This plasmid was designated as pHA3040.

Subsequently, using the genomic DNA of *Bacillus* sp. KSM-64 (FERM P-10482) as a template, primer SP64-F (EcoRI) (gggggaattcGAACAAGTACTTACCATTTTA-GAGTC: SEQ ID No: 253) and primer SP64-R (BamHI) (ggggggatccTTATTAAAGTAATTGAATCAAATAGC: SEQ ID No: 254), PCR amplification was performed to obtain a DNA fragment comprising a promoter region upstream of Endo-1,4-beta-glucanase (Genbank accession no. M84963) derived from *Bacillus* sp. KSM-64. The amplification product and pHA3040 previously constructed were mixed in appropriate amounts, digested doubly with restriction enzymes EcoRI (Roche) and BamHI (Roche), linked with Ligation High, and purified through ethanol precipitation. A host bacterium *Bacillus* spKSM-9865 strain (FERM P-18566) was transformed with this by an electroporation method and smeared on a skim milk-containing alkali LB agar medium. Several days later, colonies formed in the agar medium were separated as a transformant and a plasmid was extracted. The promoter sequence inserted within a multicloning site was analyzed to confirm whether an unwanted mutation was not introduced by PCR error. This plasmid was designated as pHA3040SP64 (SEQ ID No: 255). This was simultaneously digested with restriction enzymes BamHI and XbaI (Roche) to obtain a gene insertion/expression vector.

(2) Preparation of KP43 Protease

DNA comprising the wild type KP43 protease gene sequence (SEQ ID No: 1) (having a BamHI site upstream of the gene, 5'-terminal, and an XbaI site downstream of the gene, 3'-terminal) was simultaneously digested with BamHI and XbaI, mixed with the gene insertion/expression vector previously obtained and subjected to a ligation reaction using Ligation High (manufactured by Toyobo Co., Ltd.). The ligation product was purified through ethanol precipitation, a host bacterium, *Bacillus* sp. KSM-9865 strain (FERM P-18566) was transformed with this in accordance with an electroporation method and smeared onto a skim milk-containing alkali LB agar medium. Several days later, from colonies emerged in the agar medium, a transformant exhibiting a protease gene introduced therein was separated based on the presence or absence of skim milk dissolution plaque. Plasmid DNA was extracted from the transformant and whether the protease gene represented by SEQ ID No: 1 was correctly inserted were checked. The resultant plasmid was designated as pHA64TSB.

The transformant of the KSM-9865 strain harboring pHA64TSB was inoculated in a 5 mL seed stock medium [6.0% (w/v) polypeptone S, 0.1% yeast extract, 1.0% maltose, 0.02% magnesium sulfate.7 hydrate, 0.1% potassium dihydrogen phosphate, 0.3% anhydrous sodium carbonate, 30 ppm tetracycline] and cultured while shaking at 30° C. for 16 hours. Subsequently, to a 30 mL main medium [8% polypeptone S, 0.3% yeast extract, 10% maltose, 0.04% magnesium sulfate.7 hydrates, 0.2% potassium dihydrogenphosphate, 1.5% anhydrous sodium carbonate, 30 ppm tetracycline], the seed stock culture solution (1% (v/v)) was inoculated and cultured while shaking at 30° C. for 3 days. The culture solution containing KP43 protease obtained by culturing was centrifuged to obtain a culture supernatant. Through SDS-polyacrylamide gel electrophoresis, it was confirmed that the protein contained in the culture supernatant is KP43 protease alone. If necessary, purification for desalination was performed by gel filtration column, Econopack 10-DG (Biorad).

Reference Example 2

Method for Evaluating Enzyme Solubility (1) Method for Measuring the Amount of Protease Protein The amount of protease protein contained in the culture supernatant or in the desalted purification sample was measured by using a protein assay rapid kit (manufactured by Wako Pure Chemical Industries Ltd.) as follows. More specifically, to each well of a 96-well plate, a color emission solution (250 µL) of the kit was added, and further an enzyme sample (10 µL) appropriately diluted was mixed and stirred at room temperature for 30 minutes. Thereafter, the absorbance at 660 nm was measured by a microplate reader VersaMax (Molecular Device). From a calibration curve, which was simultaneously prepared by using a bovine thymus albumin (BSA) standard solution attached to the kit, a protease protein concentration (mg/mL in terms of BSA) was calculated.

(2) Evaluation of Solubility of Protease in Liquid Detergent

Using a culture supernatant containing the parent alkaline protease (wild type KP43; WT) or a mutant alkaline protease, the solubility in a liquid detergent was evaluated. More specifically, to each well of a 96-well plate, 150 µL, of a liquid detergent (for example, the aforementioned composition C; described in Example 3 of JP-A-2010-275468) was added. To the well, a culture supernatant containing alkaline protease different in protein concentration or desalted purification sample (6.5 µL) was added and sufficiently stirred. After the mixture was allowed to stand still at room temperature for 2 hours, the absorbance at 650 nm was measured by a microplate reader VersaMax (Molecular Device). As a blank, the absorbance of a solution to which ion exchange water was added instead of the culture supernatant was measured. The absorbance of the blank is subtracted from the absorbance of the mixture to obtain a value, which was determined as a turbidity ($\Delta$OD650 nm) and used as an index for protease solubility. Based on the obtained value at $\Delta$OD650 nm, the relative turbidity of each mutant to the parent alkaline protease (WT) was calculated in accordance with the following equation.

Relative turbidity (%)=(turbidity of mutant/concentration of mutant)/(turbidity of parent alkaline protease/concentration of parent alkaline protease)×100

The turbidity ($\Delta$OD650 nm) of a composition C to which a protease was added bears a proportionate relationship to the protease concentration of the composition. Furthermore, even if a culture supernatant was used as a protease and even if gel filtration purification sample was used, the same proportionate relationship was obtained.

Reference Example 3

Method for Measuring Protease Activity

In Examples, the activity of the obtained alkaline protease was measured by the following procedure. More specifically, 0.9 mL of a 1/15 M phosphate buffer (pH 7.4) and 40 mM Glt-Ala-Ala-Pro-Leu-p-nitroanilide/dimethyl sulfoxide solution (0.05 mL) were added in a test tube and maintained at 30° C. for 5 minutes. To this, an enzyme solution (0.05 mL) was added and a reaction was performed at 30° C. for 10 minutes and thereafter, a 5% (w/v) aqueous citric acid solution (2.0 mL) was added to terminate the reaction. The absorbance at 420 nm was measured by a spectrophotometer. Note that, 1 unit (U) of enzyme was specified as the amount of enzyme for producing 1 μmol of p-nitroaniline per minute in the above reaction.

The embodiments of the present invention are described above. It should be understood that the present invention shall not be limited to the specific embodiments described above. It is obvious for those skilled in the art to make variation or modification of these embodiments within the scope of the invention.

The entire contents of documents and patent applications cited in the specification are incorporated by reference herein.

The invention claimed is:

1. A method of improving solubility of an alkaline protease in a liquid detergent, the method comprising, in a protein comprising the alkaline protease of SEQ ID NO. 2, or in a protein comprising an alkaline protease consisting of an amino acid sequence having 95% or more identity therewith, substituting asparagine at SEQ ID No: 2 position 405, or at the position corresponding thereto, with leucine or tryptophan.

2. The method according to claim 1, wherein the liquid detergent is a concentrated liquid detergent comprising 40 to 90 mass % of a surfactant.

3. The method according to claim 1, wherein the identity is 98% or more.

4. The method according to claim 1, wherein the method comprises substituting asparagine at SEQ ID No: 2 position 405, or positions or at the position corresponding thereto, with leucine.

5. The method according to claim 4, wherein the method further comprises substituting threonine at SEQ ID No. 2 position 59, or the position corresponding thereto, with leucine.

6. The method according to claim 5, wherein the method further comprises substituting serine at SEQ ID No. 2 position 40, or the position corresponding thereto, with leucine.

7. The method according to claim 5, wherein the method further comprises substituting serine at SEQ ID No. 2 position 191, or the position corresponding thereto, with leucine.

8. The method of claim 4, wherein the method comprises substituting asparagine at SEQ ID No: 2 position 405 with leucine.

9. The method according to claim 8, wherein the method further comprises substituting threonine at SEQ ID No. 2 position 59 with leucine.

10. The method according to claim 9, wherein the method further comprises substituting serine at SEQ ID No. 2 position 40 with leucine.

11. The method according to claim 9, wherein the method further comprises substituting serine at SEQ ID No. 2 position 191 with leucine.

* * * * *

SEQUENCE LISTING

<160> NUMBER OF SEQ ID NOS: 255

<210> SEQ ID NO 1
<211> LENGTH: 2040
<212> TYPE: DNA
<213> ORGANISM: Bacillus sp. KSM-KP43

<400> SEQUENCE: 1

```
ggatccgtga ggagggaacc gaatgagaaa gaagaaaaag gtgttttat ctgttttatc      60 agctgcagcg attttgtcga ctgttgcgtt aagtaatcca tctgcaggtg gtgcaaggaa     120
ttttgatctg gatttcaaag gaattcagac aacaactgat gctaaaggtt tctccaagca    180
ggggcagact ggtgctgctg cttttctggt ggaatctgaa aatgtgaaac tcccaaaagg    240
tttgcagaag aagcttgaaa cagtcccggc aaataataaa ctccatatta tccaattcaa    300
tggaccaatt ttagaagaaa caaaacagca gctggaaaaa acaggggcaa agattctcga    360
ctacatacct gattatgctt acattgtcga gtatgagggc gatgttaagt cagcaacaag    420
caccattgag cacgtggaat ccgtggagcc ttatttgccg atatacagaa tagatcccca    480
gcttttcaca aaagggcat cagagcttgt aaaagcagtg gcgcttgata caaagcagaa    540
aaataaagag gtgcaattaa gaggcatcga acaaatcgca caattcgcaa taagcaatga    600
tgtgctatat attacggcaa agcctgagta taaggtgatg aatgatgttg cgcgtggaat    660
tgtcaaagcg gatgtggctc agagcagcta cgggttgtat ggacaaggac agatcgtagc    720
ggttgccgat acagggcttg atacaggtcg caatgacagt tcgatgcatg aagccttccg    780
cgggaaaatt actgcattat atgcattggg acggacgaat aatgccaatg atacgaatgg    840
tcatggtacg catgtggctg gctccgtatt aggaaacggc tccactaata aggaatggc    900 gcctcaggcg aatctagtct tccaatctat catggatagc ggtgggggac ttggaggact    960
accttcgaat ctgcaaacct tattcagcca agcatacagt gctggtgcca gaattcatac   1020
aaactcctgg ggagcagcag tgaatggggc ttacacaaca gattccagaa atgtggatga   1080
ctatgtgcgc aaaaatgata tgacgatcct tttcgctgcc gggaatgaag gaccgaacgg   1140
cggaaccatc agtgcaccag gcacagctaa aaatgcaata acagtcggag ctacggaaaa   1200
cctccgccca agctttgggt cttatgcgga caatatcaac catgtggcac agttctcttc   1260
acgtggaccg acaaaggatg gacggatcaa accggatgtc atggcaccgg gaacgttcat   1320
actatcagca agatcttctc ttgcaccgga ttcctccttc tgggcgaacc atgacagtaa   1380
atatgcatac atgggtggaa cgtccatggc tacaccgatc gttgctggaa acgtggcaca   1440
gcttcgtgag catttttgtga aaaacagagg catcacacca aagccttctc tattaaaagc   1500
ggcactgatt gccggtgcag ctgacatcgg ccttggctac ccgaacggta accaaggatg   1560
gggacgagtg acattggata aatccctgaa cgttgcctat gtgaacgagt ccagttctct   1620
atccaccagc caaaaagcga cgtactcgtt tactgctact gccggcaagc ctttgaaaat   1680
ctccctggta tggtctgatg ccctgcgag cacaactgct tccgtaacgc ttgtcaatga   1740
```

-continued

```
tctggacctt gtcattaccg ctccaaatgg cacacagtat gtaggaaatg actttacttc    1800
gccatacaat gataactggg atggccgcaa taacgtagaa aatgtattta ttaatgcacc    1860
acaaagcggg acgtatacaa ttgaggtaca ggcttataac gtaccggttg gaccacagac    1920
cttctcgttg gcaattgtga attaataaga taacagacaa aaaacgctgg cgtatgccag    1980 ggttttttg tttgaaatca agaaaaaagg gtagaggaat taatatggta atcgtctaga    2040
```

<210> SEQ ID NO 2
<211> LENGTH: 434
<212> TYPE: PRT
<213> ORGANISM: Bacillus sp. KSM-KP43

<400> SEQUENCE: 2

```
Asn Asp Val Ala Arg Gly Ile Val Lys Ala Asp Val Ala Gln Ser Ser
 1               5                  10                  15

Tyr Gly Leu Tyr Gly Gln Gly Gln Ile Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
 50                  55                  60

Thr Asn Gly His Gly Thr His Val Ala Gly Ser Val Leu Gly Asn Gly
 65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320
```

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
        340                 345                 350

Asp Ala Pro Ala Ser Thr Thr Ala Ser Val Thr Leu Val Asn Asp Leu
    355                 360                 365

Asp Leu Val Ile Thr Ala Pro Asn Gly Thr Gln Tyr Val Gly Asn Asp
370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide as PCR primer KG24S2

<400> SEQUENCE: 3
ataaggatcc gtgaggaggg aaccga                                        26

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide as PCR primer D11_R

<400> SEQUENCE: 4
cgctttgaca attccacgcg caac                                          24

<210> SEQ ID NO 5
<211> LENGTH: 36
<212> TYPE: DNA
<213> ORGANISM: Artificial Sequence
<220> FEATURE:
<223> OTHER INFORMATION: Oligonucleotide as PCR primer D11G_F

<400> SEQUENCE: 5
ggaattgtca aagcgggagt ggctcagagc agctac                             36

<210> SEQ ID NO 6
<211> LENGTH: 36
<212> TYPE: DNA
<213> ORGANISM: Artificial Sequence
<220> FEATURE:
<223> OTHER INFORMATION: Oligonucleotide as PCR primer KG11S

<400> SEQUENCE: 6
cccctctaga cgattaccat attaattcct ctaccc                             36

<210> SEQ ID NO 7
<211> LENGTH: 36
<212> TYPE: DNA
<213> ORGANISM: Artificial Sequence
<220> FEATURE:
<223> OTHER INFORMATION: Oligonucleotide as PCR primer D11N_F

<400> SEQUENCE: 7
ggaattgtca aagcgaatgt ggctcagagc agctac                       36

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide as PCR primer D11S_F

<400> SEQUENCE: 8
ggaattgtca aagcgtccgt ggctcagagc agctac                       36

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide as PCR primer S16_R

<400> SEQUENCE: 9
gctctgagcc acatccgctt tgac                                    24

<210> SEQ ID NO 10
<211> LENGTH: 36
<212> TYPE: DNA
<213> ORGANISM: Artificial Sequence
<220> FEATURE:
<223> OTHER INFORMATION: Oligonucleotide as PCR primer S16I_F

<400> SEQUENCE: 10
gatgtggctc agagcattta cgggttgtat ggacaa                       36

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide as PCR primer S16L_F

<400> SEQUENCE: 11
gatgtggctc agagcctttacgggttgtat ggacaa                        36

<210> SEQ ID NO 12
<211> LENGTH: 36
<212> TYPE: DNA
<213> ORGANISM: Artificial Sequence
<220> FEATURE:
<223> OTHER INFORMATION: Oligonucleotide as PCR primer S16V_F

<400> SEQUENCE: 12
gatgtggctc agagcgtgta cgggttgtat ggacaa                       36

<210> SEQ ID NO 13
<211> LENGTH: 36
<212> TYPE: DNA
<213> ORGANISM: Artificial Sequence
<220> FEATURE:
<223> OTHER INFORMATION: Oligonucleotide as PCR primer S16W_F

<400> SEQUENCE: 13
gatgtggctc agagctggta cgggttgtat ggacaa                       36

<210> SEQ ID NO 14
<211> LENGTH: 24

-continued

```
<212> TYPE: DNA
<213> ORGANISM: Artificial Sequence
<220> FEATURE:
<223> OTHER INFORMATION: Oligonucleotide as PCR primer Y20_R

<400> SEQUENCE: 14
caacccgtag ctgctctgag ccac                                              24

<210> SEQ ID NO 15
<211> LENGTH: 36
<212> TYPE: DNA
<213> ORGANISM: Artificial Sequence
<220> FEATURE:
<223> OTHER INFORMATION: Oligonucleotide as PCR primer Y20A_F

<400> SEQUENCE: 15
agcagctacg ggttggcagg acaaggacag atcgta                                 36

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide as PCR primer Q22_R

<400> SEQUENCE: 16
tccatacaac ccgtagctgc tctg                                              24

<210> SEQ ID NO 17
<211> LENGTH: 36
<212> TYPE: DNA
<213> ORGANISM: Artificial Sequence
<220> FEATURE:
<223> OTHER INFORMATION: Oligonucleotide as PCR primer Q22W_F

<400> SEQUENCE: 17
tacgggttgt atggatgggg acagatcgta gcggtt                                 36

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide as PCR primer G23_R

<400> SEQUENCE: 18
ttgtccatac aacccgtagc tgct                                              24

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide as PCR primer G23N_F

<400> SEQUENCE: 19
gggttgtatg gacaaaatca gatcgtagcg gttgcc                                 36

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide as PCR primer R37_R

<400> SEQUENCE: 20
```
acctgtatca agccctgtat cggc                                              24

<210> SEQ ID NO 21
<211> LENGTH: 36
<212> TYPE: DNA
<213> ORGANISM: Artificial Sequence
<220> FEATURE:
<223> OTHER INFORMATION: Oligonucleotide as PCR primer R37T_F

<400> SEQUENCE: 21
gggcttgata caggtacaaa tgacagttcg atgcat                                 36

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide as PCR primer S40_R

<400> SEQUENCE: 22
gtcattgcga cctgtatcaa gccc                                              24

<210> SEQ ID NO 23
<211> LENGTH: 36
<212> TYPE: DNA
<213> ORGANISM: Artificial Sequence
<220> FEATURE:
<223> OTHER INFORMATION: Oligonucleotide as PCR primer S40F_F

<400> SEQUENCE: 23
acaggtcgca atgacttctc gatgcatgaa gccttc                                 36

<210> SEQ ID NO 24
<211> LENGTH: 36
<212> TYPE: DNA
<213> ORGANISM: Artificial Sequence
<220> FEATURE:
<223> OTHER INFORMATION: Oligonucleotide as PCR primer S40I_F

<400> SEQUENCE: 24
acaggtcgca atgacatttc gatgcatgaa gccttc                                 36

<210> SEQ ID NO 25
<211> LENGTH: 36
<212> TYPE: DNA
<213> ORGANISM: Artificial Sequence
<220> FEATURE:
<223> OTHER INFORMATION: Oligonucleotide as PCR primer S40L_F

<400> SEQUENCE: 25
acaggtcgca atgacctttc gatgcatgaa gccttc                                 36

<210> SEQ ID NO 26
<211> LENGTH: 36
<212> TYPE: DNA
<213> ORGANISM: Artificial Sequence
<220> FEATURE:
<223> OTHER INFORMATION: Oligonucleotide as PCR primer S40V_F

<400> SEQUENCE: 26
acaggtcgca atgacgtgtc gatgcatgaa gccttc                                 36

<210> SEQ ID NO 27
<211> LENGTH: 36
<212> TYPE: DNA
<213> ORGANISM: Artificial Sequence

```
<220> FEATURE:
<223> OTHER INFORMATION: Oligonucleotide as PCR primer S40W_F

<400> SEQUENCE: 27
acaggtcgca atgactggtc gatgcatgaa gccttc                                36

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide as PCR primer S41I_R

<400> SEQUENCE: 28
actgtcattg cgacctgtat caag                                            24

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide as PCR primer S41I_F

<400> SEQUENCE: 29
ggtcgcaatg acagtattat gcatgaagcc ttccgc                               36

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide as PCR primer A52_R

<400> SEQUENCE: 30
agtaattttc ccgcggaagg cttc                                            24

<210> SEQ ID NO 31
<211> LENGTH: 36
<212> TYPE: DNA
<213> ORGANISM: Artificial Sequence
<220> FEATURE:
<223> OTHER INFORMATION: Oligonucleotide as PCR primer A52G_F

<400> SEQUENCE: 31
cgcgggaaaa ttactggatt atatgcattg gacgg                                36

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide as PCR primer A52S_F

<400> SEQUENCE: 32
cgcgggaaaa ttacttcctt atatgcattg gacgg                                36

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide as PCR primer L53_R

<400> SEQUENCE: 33
tgcagtaatt ttcccgcgga aggc                                            24
```

<210> SEQ ID NO 34
<211> LENGTH: 36
<212> TYPE: DNA
<213> ORGANISM: Artificial Sequence
<220> FEATURE:
<223> OTHER INFORMATION: Oligonucleotide as PCR primer L53A_F

<400> SEQUENCE: 34
gggaaaatta ctgcagcata tgcattggga cggacg        36

<210> SEQ ID NO 35
<211> LENGTH: 36
<212> TYPE: DNA
<213> ORGANISM: Artificial Sequence
<220> FEATURE:
<223> OTHER INFORMATION: Oligonucleotide as PCR primer L53I_F

<400> SEQUENCE: 35
gggaaaatta ctgcaattta tgcattggga cggacg        36

<210> SEQ ID NO 36
<211> LENGTH: 36
<212> TYPE: DNA
<213> ORGANISM: Artificial Sequence
<220> FEATURE:
<223> OTHER INFORMATION: Oligonucleotide as PCR primer L53V_F

<400> SEQUENCE: 36
gggaaaatta ctgcagtgta tgcattggga cggacg        36

<210> SEQ ID NO 37
<211> LENGTH: 24
<212> TYPE: DNA
<213> ORGANISM: Artificial Sequence
<220> FEATURE:
<223> OTHER INFORMATION: Oligonucleotide as PCR primer L56_R

<400> SEQUENCE: 37
tgcatataat gcagtaattt tccc        24

<210> SEQ ID NO 38
<211> LENGTH: 36
<212> TYPE: DNA
<213> ORGANISM: Artificial Sequence
<220> FEATURE:
<223> OTHER INFORMATION: Oligonucleotide as PCR primer L56V_F

<400> SEQUENCE: 38
actgcattat atgcagtggg acggacgaat aatgcc        36

<210> SEQ ID NO 39
<211> LENGTH: 24
<212> TYPE: DNA
<213> ORGANISM: Artificial Sequence
<220> FEATURE:
<223> OTHER INFORMATION: Oligonucleotide as PCR primer T59_R

<400> SEQUENCE: 39
ccgtcccaat gcatataatg cagt        24

<210> SEQ ID NO 40
<211> LENGTH: 36
<212> TYPE: DNA
<213> ORGANISM: Artificial Sequence
<220> FEATURE:
<223> OTHER INFORMATION: Oligonucleotide as PCR primer T59F_F

```
<400> SEQUENCE: 40
tatgcattgg gacggttcaa taatgccaat gatacg                              36

<210> SEQ ID NO 41
<211> LENGTH: 36
<212> TYPE: DNA
<213> ORGANISM: Artificial Sequence
<220> FEATURE:
<223> OTHER INFORMATION: Oligonucleotide as PCR primer T59I_F

<400> SEQUENCE: 41
tatgcattgg gacggattaa taatgccaat gatacg                              36

<210> SEQ ID NO 42
<211> LENGTH: 36
<212> TYPE: DNA
<213> ORGANISM: Artificial Sequence
<220> FEATURE:
<223> OTHER INFORMATION: Oligonucleotide as PCR primer T59L_F

<400> SEQUENCE: 42
tatgcattgg gacggcttaa taatgccaat gatccg                              36

<210> SEQ ID NO 43
<211> LENGTH: 36
<212> TYPE: DNA
<213> ORGANISM: Artificial Sequence
<220> FEATURE:
<223> OTHER INFORMATION: Oligonucleotide as PCR primer T59M_F

<400> SEQUENCE: 43
tatgcattgg gacggatgaa taatgccaat gatacg                              36

<210> SEQ ID NO 44
<211> LENGTH: 36
<212> TYPE: DNA
<213> ORGANISM: Artificial Sequence
<220> FEATURE:
<223> OTHER INFORMATION: Oligonucleotide as PCR primer T59V_F

<400> SEQUENCE: 44
tatgcattgg gacgggtgaa taatgccaat gatacg                              36

<210> SEQ ID NO 45
<211> LENGTH: 36
<212> TYPE: DNA
<213> ORGANISM: Artificial Sequence
<220> FEATURE:
<223> OTHER INFORMATION: Oligonucleotide as PCR primer T59W_F

<400> SEQUENCE: 45
tatgcattgg gacggtggaa taatgccaat gatacg                              36

<210> SEQ ID NO 46
<211> LENGTH: 24
<212> TYPE: DNA
<213> ORGANISM: Artificial Sequence
<220> FEATURE:
<223> OTHER INFORMATION: Oligonucleotide as PCR primer N60_R

<400> SEQUENCE: 46
cgtccgtccc aatgcatata atgc                                           24

<210> SEQ ID NO 47
```

<210> SEQ ID NO 47
<211> LENGTH: 36
<212> TYPE: DNA
<213> ORGANISM: Artificial Sequence
<220> FEATURE:
<223> OTHER INFORMATION: Oligonucleotide as PCR primer N60F_F

<400> SEQUENCE: 47
gcattgggac ggacgttcaa tgccaatgat acgaat                    36

<210> SEQ ID NO 48
<211> LENGTH: 36
<212> TYPE: DNA
<213> ORGANISM: Artificial Sequence
<220> FEATURE:
<223> OTHER INFORMATION: Oligonucleotide as PCR primer N60I_F

<400> SEQUENCE: 48
gcattgggac ggacgattaa tgccaatgat acgaat                    36

<210> SEQ ID NO 49
<211> LENGTH: 36
<212> TYPE: DNA
<213> ORGANISM: Artificial Sequence
<220> FEATURE:
<223> OTHER INFORMATION: Oligonucleotide as PCR primer N60L_F

<400> SEQUENCE: 49
gcattgggac ggacgcttaa tgccaatgat acgaat                    36

<210> SEQ ID NO 50
<211> LENGTH: 36
<212> TYPE: DNA
<213> ORGANISM: Artificial Sequence
<220> FEATURE:
<223> OTHER INFORMATION: Oligonucleotide as PCR primer N60V_F

<400> SEQUENCE: 50
gcattgggac ggacggtgaa tgccaatgat acgaat                    36

<210> SEQ ID NO 51
<211> LENGTH: 36
<212> TYPE: DNA
<213> ORGANISM: Artificial Sequence
<220> FEATURE:
<223> OTHER INFORMATION: Oligonucleotide as PCR primer N60W_F

<400> SEQUENCE: 51
gcattgggac ggacgtggaa tgccaatgat acgaat                    36

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide as PCR primer N63_R

<400> SEQUENCE: 52
ggcattattc gtccgtccca atgc                                 24

<210> SEQ ID NO 53
<211> LENGTH: 36
<212> TYPE: DNA
<213> ORGANISM: Artificial Sequence
<220> FEATURE:
<223> OTHER INFORMATION: Oligonucleotide as PCR primer N63D_F

<400> SEQUENCE: 53
cggacgaata atgccgatga tacgaatggt catggt                                36

<210> SEQ ID NO 54
<211> LENGTH: 36
<212> TYPE: DNA
<213> ORGANISM: Artificial Sequence
<220> FEATURE:
<223> OTHER INFORMATION: Oligonucleotide as PCR primer N63L_F

<400> SEQUENCE: 54
cggacgaata atgcccttga tacgaatggt catggt                                36

<210> SEQ ID NO 55
<211> LENGTH: 24
<212> TYPE: DNA
<213> ORGANISM: Artificial Sequence
<220> FEATURE:
<223> OTHER INFORMATION: Oligonucleotide as PCR primer G80_R

<400> SEQUENCE: 55
gtttcctaat acggagccag ccac                                             24

<210> SEQ ID NO 56
<211> LENGTH: 36
<212> TYPE: DNA
<213> ORGANISM: Artificial Sequence
<220> FEATURE:
<223> OTHER INFORMATION: Oligonucleotide as PCR primer G80A_F

<400> SEQUENCE: 56
tccgtattag gaaacgcatc cactaataaa ggaatg                                36

<210> SEQ ID NO 57
<211> LENGTH: 36
<212> TYPE: DNA
<213> ORGANISM: Artificial Sequence
<220> FEATURE:
<223> OTHER INFORMATION: Oligonucleotide as PCR primer G80H_F

<400> SEQUENCE: 57
tccgtattag gaaaccattc cactaataaa ggaatg                                36

<210> SEQ ID NO 58
<211> LENGTH: 24
<212> TYPE: DNA
<213> ORGANISM: Artificial Sequence
<220> FEATURE:
<223> OTHER INFORMATION: Oligonucleotide as PCR primer S81_R

<400> SEQUENCE: 58
gccgtttcct aatacggagc cagc                                             24

<210> SEQ ID NO 59
<211> LENGTH: 36
<212> TYPE: DNA
<213> ORGANISM: Artificial Sequence
<220> FEATURE:
<223> OTHER INFORMATION: Oligonucleotide as PCR primer S81F_F

<400> SEQUENCE: 59
gtattaggaa acggcttcac taataaagga atggcg                                36

<210> SEQ ID NO 60
<211> LENGTH: 36
<212> TYPE: DNA

```
<213> ORGANISM: Artificial Sequence
<220> FEATURE:
<223> OTHER INFORMATION: Oligonucleotide as PCR primer S81I_F

<400> SEQUENCE: 60
gtattaggaa acggcattac taataaagga atggcg                                    36

<210> SEQ ID NO 61
<211> LENGTH: 36
<212> TYPE: DNA
<213> ORGANISM: Artificial Sequence
<220> FEATURE:
<223> OTHER INFORMATION: Oligonucleotide as PCR primer S81L_F

<400> SEQUENCE: 61
gtattaggaa acggccttac taataaagga atggcg                                    36

<210> SEQ ID NO 62
<211> LENGTH: 36
<212> TYPE: DNA
<213> ORGANISM: Artificial Sequence
<220> FEATURE:
<223> OTHER INFORMATION: Oligonucleotide as PCR primer S81Q_F

<400> SEQUENCE: 62
gtattaggaa acggccagac taataaagga atggcg                                    36

<210> SEQ ID NO 63
<211> LENGTH: 36
<212> TYPE: DNA
<213> ORGANISM: Artificial Sequence
<220> FEATURE:
<223> OTHER INFORMATION: Oligonucleotide as PCR primer S81W_F

<400> SEQUENCE: 63
gtattaggaa acggctggac taataaagga atggcg                                    36

<210> SEQ ID NO 64
<211> LENGTH: 36
<212> TYPE: DNA
<213> ORGANISM: Artificial Sequence
<220> FEATURE:
<223> OTHER INFORMATION: Oligonucleotide as PCR primer S81Y_F

<400> SEQUENCE: 64
gtattaggaa acggctatac taataaagga atggcg                                    36

<210> SEQ ID NO 65
<211> LENGTH: 24
<212> TYPE: DNA
<213> ORGANISM: Artificial Sequence
<220> FEATURE:
<223> OTHER INFORMATION: Oligonucleotide as PCR primer T82_R

<400> SEQUENCE: 65
ggagccgttt cctaatacgg agcc                                                 24

<210> SEQ ID NO 66
<211> LENGTH: 36
<212> TYPE: DNA
<213> ORGANISM: Artificial Sequence
<220> FEATURE:
<223> OTHER INFORMATION: Oligonucleotide as PCR primer T82Q_F

<400> SEQUENCE: 66
ttaggaaacg gctcccagaa taaggaatg gcgcct                                     36
```

<210> SEQ ID NO 67
<211> LENGTH: 24
<212> TYPE: DNA
<213> ORGANISM: Artificial Sequence
<220> FEATURE:
<223> OTHER INFORMATION: Oligonucleotide as PCR primer N91_R

<400> SEQUENCE: 67
cgcctgaggc gccattcctt tatt                                          24

<210> SEQ ID NO 68
<211> LENGTH: 36
<212> TYPE: DNA
<213> ORGANISM: Artificial Sequence
<220> FEATURE:
<223> OTHER INFORMATION: Oligonucleotide as PCR primer N91C_F

<400> SEQUENCE: 68
atggcgcctc aggcgtgcct agtcttccaa tctatc                             36

<210> SEQ ID NO 69
<211> LENGTH: 24
<212> TYPE: DNA
<213> ORGANISM: Artificial Sequence
<220> FEATURE:
<223> OTHER INFORMATION: Oligonucleotide as PCR primer S100_R

<400> SEQUENCE: 69
atccatgata gattggaaga ctag                                          24

<210> SEQ ID NO 70
<211> LENGTH: 36
<212> TYPE: DNA
<213> ORGANISM: Artificial Sequence
<220> FEATURE:
<223> OTHER INFORMATION: Oligonucleotide as PCR primer S100F_F

<400> SEQUENCE: 70
caatctatca tggatttcgg tggggacttg gagga                              36

<210> SEQ ID NO 71
<211> LENGTH: 36
<212> TYPE: DNA
<213> ORGANISM: Artificial Sequence
<220> FEATURE:
<223> OTHER INFORMATION: Oligonucleotide as PCR primer S100I_F

<400> SEQUENCE: 71
caatctatca tggatattgg tggggacttg gagga                              36

<210> SEQ ID NO 72
<211> LENGTH: 36
<212> TYPE: DNA
<213> ORGANISM: Artificial Sequence
<220> FEATURE:
<223> OTHER INFORMATION: Oligonucleotide as PCR primer S100L_F

<400> SEQUENCE: 72
caatctatca tggatcttgg tggggacttg gagga                              36

<210> SEQ ID NO 73
<211> LENGTH: 36
<212> TYPE: DNA
<213> ORGANISM: Artificial Sequence
<220> FEATURE:

<223> OTHER INFORMATION: Oligonucleotide as PCR primer S100W_F

<400> SEQUENCE: 73
caatctatca tggattgggg tggggggactt ggagga                                    36

<210> SEQ ID NO 74
<211> LENGTH: 24
<212> TYPE: DNA
<213> ORGANISM: Artificial Sequence
<220> FEATURE:
<223> OTHER INFORMATION: Oligonucleotide as PCR primer G101_R

<400> SEQUENCE: 74
gctatccatg atagattgga agac                                                 24

<210> SEQ ID NO 75
<211> LENGTH: 36
<212> TYPE: DNA
<213> ORGANISM: Artificial Sequence
<220> FEATURE:
<223> OTHER INFORMATION: Oligonucleotide as PCR primer G101F_F

<400> SEQUENCE: 75
tctatcatgg atagcttcgg gggacttgga ggacta                                    36

<210> SEQ ID NO 76
<211> LENGTH: 36
<212> TYPE: DNA
<213> ORGANISM: Artificial Sequence
<220> FEATURE:
<223> OTHER INFORMATION: Oligonucleotide as PCR primer G101I_F

<400> SEQUENCE: 76
tctatcatgg atagcattgg gggacttgga ggacta                                    36

<210> SEQ ID NO 77
<211> LENGTH: 36
<212> TYPE: DNA
<213> ORGANISM: Artificial Sequence
<220> FEATURE:
<223> OTHER INFORMATION: Oligonucleotide as PCR primer G101L_F

<400> SEQUENCE: 77
tctatcatgg atagccttgg gggacttgga ggacta                                    36

<210> SEQ ID NO 78
<211> LENGTH: 36
<212> TYPE: DNA
<213> ORGANISM: Artificial Sequence
<220> FEATURE:
<223> OTHER INFORMATION: Oligonucleotide as PCR primer G101V_F

<400> SEQUENCE: 78
tctatcatgg atagcgtggg gggacttgga ggacta                                    36

<210> SEQ ID NO 79
<211> LENGTH: 36
<212> TYPE: DNA
<213> ORGANISM: Artificial Sequence
<220> FEATURE:
<223> OTHER INFORMATION: Oligonucleotide as PCR primer G101W_F

<400> SEQUENCE: 79
tctatcatgg atagctgggg gggacttgga ggacta                                    36

```
<210> SEQ ID NO 80
<211> LENGTH: 36
<212> TYPE: DNA
<213> ORGANISM: Artificial Sequence
<220> FEATURE:
<223> OTHER INFORMATION: Oligonucleotide as PCR primer G101Y_F

<400> SEQUENCE: 80
tctatcatgg atagctatgg gggacttgga ggacta                              36

<210> SEQ ID NO 81
<211> LENGTH: 24
<212> TYPE: DNA
<213> ORGANISM: Artificial Sequence
<220> FEATURE:
<223> OTHER INFORMATION: Oligonucleotide as PCR primer S109_R

<400> SEQUENCE: 81
aggtagtcct ccaagtcccc cacc                                           24

<210> SEQ ID NO 82
<211> LENGTH: 36
<212> TYPE: DNA
<213> ORGANISM: Artificial Sequence
<220> FEATURE:
<223> OTHER INFORMATION: Oligonucleotide as PCR primer S109F_F

<400> SEQUENCE: 82
cttggaggac tacctttcaa tctgcaaacc ttattc                              36

<210> SEQ ID NO 83
<211> LENGTH: 36
<212> TYPE: DNA
<213> ORGANISM: Artificial Sequence
<220> FEATURE:
<223> OTHER INFORMATION: Oligonucleotide as PCR primer S109I_F

<400> SEQUENCE: 83
cttggaggac tacctattaa tctgcaaacc ttattc                              36

<210> SEQ ID NO 84
<211> LENGTH: 36
<212> TYPE: DNA
<213> ORGANISM: Artificial Sequence
<220> FEATURE:
<223> OTHER INFORMATION: Oligonucleotide as PCR primer S109L_F

<400> SEQUENCE: 84
cttggaggac tacctcttaa tctgcaaacc ttattc                              36

<210> SEQ ID NO 85
<211> LENGTH: 24
<212> TYPE: DNA
<213> ORGANISM: Artificial Sequence
<220> FEATURE:
<223> OTHER INFORMATION: Oligonucleotide as PCR primer T113_R

<400> SEQUENCE: 85
ttgcagattc gaaggtagtc ctcc                                           24

<210> SEQ ID NO 86
<211> LENGTH: 36
<212> TYPE: DNA
<213> ORGANISM: Artificial Sequence
<220> FEATURE:
<223> OTHER INFORMATION: Oligonucleotide as PCR primer T113L_F
```

<400> SEQUENCE: 86
ccttcgaatc tgcaactttt attcagccaa gcatac    36

<210> SEQ ID NO 87
<211> LENGTH: 36
<212> TYPE: DNA
<213> ORGANISM: Artificial Sequence
<220> FEATURE:
<223> OTHER INFORMATION: Oligonucleotide as PCR primer T113W_F

<400> SEQUENCE: 87
ccttcgaatc tgcaatggtt attcagccaa gcatac    36

<210> SEQ ID NO 88
<211> LENGTH: 24
<212> TYPE: DNA
<213> ORGANISM: Artificial Sequence
<220> FEATURE:
<223> OTHER INFORMATION: Oligonucleotide as PCR primer S120_R

<400> SEQUENCE: 88
gtatgcttgg ctgaataagg tttg    24

<210> SEQ ID NO 89
<211> LENGTH: 36
<212> TYPE: DNA
<213> ORGANISM: Artificial Sequence
<220> FEATURE:
<223> OTHER INFORMATION: Oligonucleotide as PCR primer S120F_F

<400> SEQUENCE: 89
ttcagccaag catacttcgc tggtgccaga attcat    36

<210> SEQ ID NO 90
<211> LENGTH: 36
<212> TYPE: DNA
<213> ORGANISM: Artificial Sequence
<220> FEATURE:
<223> OTHER INFORMATION: Oligonucleotide as PCR primer S120I_F

<400> SEQUENCE: 90
ttcagccaag catacattgc tggtgccaga attcat    36

<210> SEQ ID NO 91
<211> LENGTH: 36
<212> TYPE: DNA
<213> ORGANISM: Artificial Sequence
<220> FEATURE:
<223> OTHER INFORMATION: Oligonucleotide as PCR primer S120W_F

<400> SEQUENCE: 91
ttcagccaag catactgggc tggtgccaga attcat    36

<210> SEQ ID NO 92
<211> LENGTH: 36
<212> TYPE: DNA
<213> ORGANISM: Artificial Sequence
<220> FEATURE:
<223> OTHER INFORMATION: Oligonucleotide as PCR primer S120Y_F

<400> SEQUENCE: 92
ttcagccaag catactatgc tggtgccaga attcat    36

<210> SEQ ID NO 93
<211> LENGTH: 24

```
<212> TYPE: DNA
<213> ORGANISM: Artificial Sequence
<220> FEATURE:
<223> OTHER INFORMATION: Oligonucleotide as PCR primer N135_R

<400> SEQUENCE: 93
cactgctgct ccccaggagt ttgt                                           24

<210> SEQ ID NO 94
<211> LENGTH: 36
<212> TYPE: DNA
<213> ORGANISM: Artificial Sequence
<220> FEATURE:
<223> OTHER INFORMATION: Oligonucleotide as PCR primer N135L_F

<400> SEQUENCE: 94
tggggagcag cagtgcttgg ggcttacaca acagat                              36

<210> SEQ ID NO 95
<211> LENGTH: 24
<212> TYPE: DNA
<213> ORGANISM: Artificial Sequence
<220> FEATURE:
<223> OTHER INFORMATION: Oligonucleotide as PCR primer T140_R

<400> SEQUENCE: 95
tgtgtaagcc ccattcactg ctgc                                           24

<210> SEQ ID NO 96
<211> LENGTH: 36
<212> TYPE: DNA
<213> ORGANISM: Artificial Sequence
<220> FEATURE:
<223> OTHER INFORMATION: Oligonucleotide as PCR primer T140F_F

<400> SEQUENCE: 96
aatggggctt acacattcga ttccagaaat gtggat                              36

<210> SEQ ID NO 97
<211> LENGTH: 36
<212> TYPE: DNA
<213> ORGANISM: Artificial Sequence
<220> FEATURE:
<223> OTHER INFORMATION: Oligonucleotide as PCR primer T140L_F

<400> SEQUENCE: 97
aatggggctt acacacttga ttccagaaat gtggat                              36

<210> SEQ ID NO 98
<211> LENGTH: 36
<212> TYPE: DNA
<213> ORGANISM: Artificial Sequence
<220> FEATURE:
<223> OTHER INFORMATION: Oligonucleotide as PCR primer T140W_F

<400> SEQUENCE: 98
aatggggctt acacatggga ttccagaaat gtggat                              36

<210> SEQ ID NO 99
<211> LENGTH: 24
<212> TYPE: DNA
<213> ORGANISM: Artificial Sequence
<220> FEATURE:
<223> OTHER INFORMATION: Oligonucleotide as PCR primer K151_R

<400> SEQUENCE: 99
```

```
gcgcacatag tcatccacat ttct                                            24

<210> SEQ ID NO 100
<211> LENGTH: 36
<212> TYPE: DNA
<213> ORGANISM: Artificial Sequence
<220> FEATURE:
<223> OTHER INFORMATION: Oligonucleotide as PCR primer K151F_F

<400> SEQUENCE: 100
gatgactatg tgcgcttcaa tgatatgacg atcctt                               36

<210> SEQ ID NO 101
<211> LENGTH: 24
<212> TYPE: DNA
<213> ORGANISM: Artificial Sequence
<220> FEATURE:
<223> OTHER INFORMATION: Oligonucleotide as PCR primer N166_R

<400> SEQUENCE: 101
cggtccttca ttcccggcag cgaa                                            24

<210> SEQ ID NO 102
<211> LENGTH: 36
<212> TYPE: DNA
<213> ORGANISM: Artificial Sequence
<220> FEATURE:
<223> OTHER INFORMATION: Oligonucleotide as PCR primer N166F_F

<400> SEQUENCE: 102
gggaatgaag gaccgttcgg cggaaccatc agtgca                               36

<210> SEQ ID NO 103
<211> LENGTH: 36
<212> TYPE: DNA
<213> ORGANISM: Artificial Sequence
<220> FEATURE:
<223> OTHER INFORMATION: Oligonucleotide as PCR primer N166I_F

<400> SEQUENCE: 103
gggaatgaag gaccgattgg cggaaccatc agtgca                               36

<210> SEQ ID NO 104
<211> LENGTH: 36
<212> TYPE: DNA
<213> ORGANISM: Artificial Sequence
<220> FEATURE:
<223> OTHER INFORMATION: Oligonucleotide as PCR primer N166L_F

<400> SEQUENCE: 104
gggaatgaag gaccgcttgg cggaaccatc agtgca                               36

<210> SEQ ID NO 105
<211> LENGTH: 36
<212> TYPE: DNA
<213> ORGANISM: Artificial Sequence
<220> FEATURE:
<223> OTHER INFORMATION: Oligonucleotide as PCR primer N166V_F

<400> SEQUENCE: 105
gggaatgaag gaccggtggg cggaaccatc agtgca                               36

<210> SEQ ID NO 106
<211> LENGTH: 36
<212> TYPE: DNA
<213> ORGANISM: Artificial Sequence
```

```
<220> FEATURE:
<223> OTHER INFORMATION: Oligonucleotide as PCR primer N166W_F

<400> SEQUENCE: 106
gggaatgaag gaccgtgggg cggaaccatc agtgca                                    36

<210> SEQ ID NO 107
<211> LENGTH: 24
<212> TYPE: DNA
<213> ORGANISM: Artificial Sequence
<220> FEATURE:
<223> OTHER INFORMATION: Oligonucleotide as PCR primer S191_R

<400> SEQUENCE: 107
tgggcggagg ttttccgtag ctcc                                                 24

<210> SEQ ID NO 108
<211> LENGTH: 36
<212> TYPE: DNA
<213> ORGANISM: Artificial Sequence
<220> FEATURE:
<223> OTHER INFORMATION: Oligonucleotide as PCR primer S191F_F

<400> SEQUENCE: 108
gaaaacctcc gcccattctt tgggtcttat gcggac                                    36

<210> SEQ ID NO 109
<211> LENGTH: 36
<212> TYPE: DNA
<213> ORGANISM: Artificial Sequence
<220> FEATURE:
<223> OTHER INFORMATION: Oligonucleotide as PCR primer S191I_F

<400> SEQUENCE: 109
gaaaacctcc gcccaatttt tgggtcttat gcggac                                    36

<210> SEQ ID NO 110
<211> LENGTH: 36
<212> TYPE: DNA
<213> ORGANISM: Artificial Sequence
<220> FEATURE:
<223> OTHER INFORMATION: Oligonucleotide as PCR primer S191L_F

<400> SEQUENCE: 110
gaaaacctcc gcccactttt tgggtcttat gcggac                                    36

<210> SEQ ID NO 111
<211> LENGTH: 36
<212> TYPE: DNA
<213> ORGANISM: Artificial Sequence
<220> FEATURE:
<223> OTHER INFORMATION: Oligonucleotide as PCR primer S191V_F

<400> SEQUENCE: 111
gaaaacctcc gcccagtgtt tgggtcttat gcggac                                    36

<210> SEQ ID NO 112
<211> LENGTH: 36
<212> TYPE: DNA
<213> ORGANISM: Artificial Sequence
<220> FEATURE:
<223> OTHER INFORMATION: Oligonucleotide as PCR primer S191W_F

<400> SEQUENCE: 112
gaaaacctcc gcccatggtt tgggtcttat gcggac                                    36
```

<210> SEQ ID NO 113
<211> LENGTH: 24
<212> TYPE: DNA
<213> ORGANISM: Artificial Sequence
<220> FEATURE:
<223> OTHER INFORMATION: Oligonucleotide as PCR primer S194_R

<400> SEQUENCE: 113
cccaaagctt gggcggaggt tttc                                          24

<210> SEQ ID NO 114
<211> LENGTH: 36
<212> TYPE: DNA
<213> ORGANISM: Artificial Sequence
<220> FEATURE:
<223> OTHER INFORMATION: Oligonucleotide as PCR primer S194Y_F

<400> SEQUENCE: 114
cgcccaagct tgggtatta tgcggacaat atcaac                              36

<210> SEQ ID NO 115
<211> LENGTH: 24
<212> TYPE: DNA
<213> ORGANISM: Artificial Sequence
<220> FEATURE:
<223> OTHER INFORMATION: Oligonucleotide as PCR primer N200_R

<400> SEQUENCE: 115
gatattgtcc gcataagacc caaa                                          24

<210> SEQ ID NO 116
<211> LENGTH: 36
<212> TYPE: DNA
<213> ORGANISM: Artificial Sequence
<220> FEATURE:
<223> OTHER INFORMATION: Oligonucleotide as PCR primer N200W_F

<400> SEQUENCE: 116
tatgcggaca atatctggca tgtggcacag ttctct                             36

<210> SEQ ID NO 117
<211> LENGTH: 24
<212> TYPE: DNA
<213> ORGANISM: Artificial Sequence
<220> FEATURE:
<223> OTHER INFORMATION: Oligonucleotide as PCR primer Q204_R

<400> SEQUENCE: 117
tgccacatgg ttgatattgt ccgc                                          24

<210> SEQ ID NO 118
<211> LENGTH: 36
<212> TYPE: DNA
<213> ORGANISM: Artificial Sequence
<220> FEATURE:
<223> OTHER INFORMATION: Oligonucleotide as PCR primer Q204I_F

<400> SEQUENCE: 118
atcaaccatg tggcaattt ctcttcacgt ggaccg                              36

<210> SEQ ID NO 119
<211> LENGTH: 36
<212> TYPE: DNA
<213> ORGANISM: Artificial Sequence
<220> FEATURE:
<223> OTHER INFORMATION: Oligonucleotide as PCR primer Q204L_F

<400> SEQUENCE: 119
atcaaccatg tggcactttt ctcttcacgt ggaccg					36

<210> SEQ ID NO 120
<211> LENGTH: 36
<212> TYPE: DNA
<213> ORGANISM: Artificial Sequence
<220> FEATURE:
<223> OTHER INFORMATION: Oligonucleotide as PCR primer Q204M_F

<400> SEQUENCE: 120
atcaaccatg tggcaatgtt ctcttcacgt ggaccg					36

<210> SEQ ID NO 121
<211> LENGTH: 36
<212> TYPE: DNA
<213> ORGANISM: Artificial Sequence
<220> FEATURE:
<223> OTHER INFORMATION: Oligonucleotide as PCR primer Q204V_F

<400> SEQUENCE: 121
atcaaccatg tggcagtgtt ctcttcacgt ggaccg					36

<210> SEQ ID NO 122
<211> LENGTH: 24
<212> TYPE: DNA
<213> ORGANISM: Artificial Sequence
<220> FEATURE:
<223> OTHER INFORMATION: Oligonucleotide as PCR primer K212_R

<400> SEQUENCE: 122
tgtcggtcca cgtgaagaga actg					24

<210> SEQ ID NO 123
<211> LENGTH: 36
<212> TYPE: DNA
<213> ORGANISM: Artificial Sequence
<220> FEATURE:
<223> OTHER INFORMATION: Oligonucleotide as PCR primer K212L_F

<400> SEQUENCE: 123
tcacgtggac cgacacttga tggacggatc aaaccg					36

<210> SEQ ID NO 124
<211> LENGTH: 36
<212> TYPE: DNA
<213> ORGANISM: Artificial Sequence
<220> FEATURE:
<223> OTHER INFORMATION: Oligonucleotide as PCR primer K212V_F

<400> SEQUENCE: 124
tcacgtggac cgacagtgga tggacggatc aaaccg					36

<210> SEQ ID NO 125
<211> LENGTH: 36
<212> TYPE: DNA
<213> ORGANISM: Artificial Sequence
<220> FEATURE:
<223> OTHER INFORMATION: Oligonucleotide as PCR primer K212W_F

<400> SEQUENCE: 125
tcacgtggac cgacatggga tggacggatc aaaccg					36

<210> SEQ ID NO 126

```
<211> LENGTH: 24
<212> TYPE: DNA
<213> ORGANISM: Artificial Sequence
<220> FEATURE:
<223> OTHER INFORMATION: Oligonucleotide as PCR primer S233_R

<400> SEQUENCE: 126
agatcttgct gatagtatga acgt                                              24

<210> SEQ ID NO 127
<211> LENGTH: 36
<212> TYPE: DNA
<213> ORGANISM: Artificial Sequence
<220> FEATURE:
<223> OTHER INFORMATION: Oligonucleotide as PCR primer S233I_F

<400> SEQUENCE: 127
ctatcagcaa gatctattct tgcaccggat cctcc                                  36

<210> SEQ ID NO 128
<211> LENGTH: 36
<212> TYPE: DNA
<213> ORGANISM: Artificial Sequence
<220> FEATURE:
<223> OTHER INFORMATION: Oligonucleotide as PCR primer S233L_F

<400> SEQUENCE: 128
ctatcagcaa gatctcttct tgcaccggat cctcc                                  36

<210> SEQ ID NO 129
<211> LENGTH: 36
<212> TYPE: DNA
<213> ORGANISM: Artificial Sequence
<220> FEATURE:
<223> OTHER INFORMATION: Oligonucleotide as PCR primer S233W_F

<400> SEQUENCE: 129
ctatcagcaa gatcttggct tgcaccggat cctcc                                  36

<210> SEQ ID NO 130
<211> LENGTH: 24
<212> TYPE: DNA
<213> ORGANISM: Artificial Sequence
<220> FEATURE:
<223> OTHER INFORMATION: Oligonucleotide as PCR primer S238_R

<400> SEQUENCE: 130
atccggtgca agagaagatc ttgc                                              24

<210> SEQ ID NO 131
<211> LENGTH: 36
<212> TYPE: DNA
<213> ORGANISM: Artificial Sequence
<220> FEATURE:
<223> OTHER INFORMATION: Oligonucleotide as PCR primer S238L_F

<400> SEQUENCE: 131
tctcttgcac cggatctttc cttctgggcg aaccat                                 36

<210> SEQ ID NO 132
<211> LENGTH: 24
<212> TYPE: DNA
<213> ORGANISM: Artificial Sequence
<220> FEATURE:
<223> OTHER INFORMATION: Oligonucleotide as PCR primer N243_R

<400> SEQUENCE: 132
```

```
cgcccagaag gaggaatccg gtgc                                            24

<210> SEQ ID NO 133
<211> LENGTH: 36
<212> TYPE: DNA
<213> ORGANISM: Artificial Sequence
<220> FEATURE:
<223> OTHER INFORMATION: Oligonucleotide as PCR primer N243I_F

<400> SEQUENCE: 133
tcctccttct gggcgattca tgacagtaaa tatgca                               36

<210> SEQ ID NO 134
<211> LENGTH: 36
<212> TYPE: DNA
<213> ORGANISM: Artificial Sequence
<220> FEATURE:
<223> OTHER INFORMATION: Oligonucleotide as PCR primer N243L_F

<400> SEQUENCE: 134
tcctccttct gggcgcttca tgacagtaaa tatgca                               36

<210> SEQ ID NO 135
<211> LENGTH: 36
<212> TYPE: DNA
<213> ORGANISM: Artificial Sequence
<220> FEATURE:
<223> OTHER INFORMATION: Oligonucleotide as PCR primer N243Y_F

<400> SEQUENCE: 135
tcctccttct gggcgtatca tgacagtaaa tatgca                               36

<210> SEQ ID NO 136
<211> LENGTH: 24
<212> TYPE: DNA
<213> ORGANISM: Artificial Sequence
<220> FEATURE:
<223> OTHER INFORMATION: Oligonucleotide as PCR primer S246_R

<400> SEQUENCE: 136
gtcatggttc gcccagaagg agga                                            24

<210> SEQ ID NO 137
<211> LENGTH: 36
<212> TYPE: DNA
<213> ORGANISM: Artificial Sequence
<220> FEATURE:
<223> OTHER INFORMATION: Oligonucleotide as PCR primer S246F_F

<400> SEQUENCE: 137
tgggcgaacc atgacttcaa atatgcatac atgggt                               36

<210> SEQ ID NO 138
<211> LENGTH: 36
<212> TYPE: DNA
<213> ORGANISM: Artificial Sequence
<220> FEATURE:
<223> OTHER INFORMATION: Oligonucleotide as PCR primer S246L_F

<400> SEQUENCE: 138
tgggcgaacc atgaccttaa atatgcatac atgggt                               36

<210> SEQ ID NO 139
<211> LENGTH: 36
<212> TYPE: DNA
```

<213> ORGANISM: Artificial Sequence
<220> FEATURE:
<223> OTHER INFORMATION: Oligonucleotide as PCR primer S246V_F

<400> SEQUENCE: 139
tgggcgaacc atgacgtgaa atatgcatac atgggt         36

<210> SEQ ID NO 140
<211> LENGTH: 36
<212> TYPE: DNA
<213> ORGANISM: Artificial Sequence
<220> FEATURE:
<223> OTHER INFORMATION: Oligonucleotide as PCR primer S246W_F

<400> SEQUENCE: 140
tgggcgaacc atgactggaa atatgcatac atgggt         36

<210> SEQ ID NO 141
<211> LENGTH: 36
<212> TYPE: DNA
<213> ORGANISM: Artificial Sequence
<220> FEATURE:
<223> OTHER INFORMATION: Oligonucleotide as PCR primer S246Y_F

<400> SEQUENCE: 141
tgggcgaacc atgactataa atatgcatac atgggt         36

<210> SEQ ID NO 142
<211> LENGTH: 24
<212> TYPE: DNA
<213> ORGANISM: Artificial Sequence
<220> FEATURE:
<223> OTHER INFORMATION: Oligonucleotide as PCR primer N275_R

<400> SEQUENCE: 142
tttcacaaaa tgctcacgaa gctg         24

<210> SEQ ID NO 143
<211> LENGTH: 36
<212> TYPE: DNA
<213> ORGANISM: Artificial Sequence
<220> FEATURE:
<223> OTHER INFORMATION: Oligonucleotide as PCR primer N275F_F

<400> SEQUENCE: 143
gagcattttg tgaaattcag aggcatcaca ccaaag         36

<210> SEQ ID NO 144
<211> LENGTH: 36
<212> TYPE: DNA
<213> ORGANISM: Artificial Sequence
<220> FEATURE:
<223> OTHER INFORMATION: Oligonucleotide as PCR primer N275L_F

<400> SEQUENCE: 144
gagcattttg tgaaacttag aggcatcaca ccaaag         36

<210> SEQ ID NO 145
<211> LENGTH: 36
<212> TYPE: DNA
<213> ORGANISM: Artificial Sequence
<220> FEATURE:
<223> OTHER INFORMATION: Oligonucleotide as PCR primer N275W_F

<400> SEQUENCE: 145
gagcattttg tgaaatggag aggcatcaca ccaaag         36

<210> SEQ ID NO 146
<211> LENGTH: 24
<212> TYPE: DNA
<213> ORGANISM: Artificial Sequence
<220> FEATURE:
<223> OTHER INFORMATION: Oligonucleotide as PCR primer G277_R

<400> SEQUENCE: 146
tctgtttttc acaaaatgct cacg                                         24

<210> SEQ ID NO 147
<211> LENGTH: 36
<212> TYPE: DNA
<213> ORGANISM: Artificial Sequence
<220> FEATURE:
<223> OTHER INFORMATION: Oligonucleotide as PCR primer G277F_F

<400> SEQUENCE: 147
tttgtgaaaa acagattcat cacaccaaag ccttct                            36

<210> SEQ ID NO 148
<211> LENGTH: 36
<212> TYPE: DNA
<213> ORGANISM: Artificial Sequence
<220> FEATURE:
<223> OTHER INFORMATION: Oligonucleotide as PCR primer G277I_F

<400> SEQUENCE: 148
tttgtgaaaa acagaattat cacaccaaag ccttct                            36

<210> SEQ ID NO 149
<211> LENGTH: 36
<212> TYPE: DNA
<213> ORGANISM: Artificial Sequence
<220> FEATURE:
<223> OTHER INFORMATION: Oligonucleotide as PCR primer G277L_F

<400> SEQUENCE: 149
tttgtgaaaa acagacttat cacaccaaag ccttct                            36

<210> SEQ ID NO 150
<211> LENGTH: 36
<212> TYPE: DNA
<213> ORGANISM: Artificial Sequence
<220> FEATURE:
<223> OTHER INFORMATION: Oligonucleotide as PCR primer G277V_F

<400> SEQUENCE: 150
tttgtgaaaa acagagtgat cacaccaaag ccttct                            36

<210> SEQ ID NO 151
<211> LENGTH: 24
<212> TYPE: DNA
<213> ORGANISM: Artificial Sequence
<220> FEATURE:
<223> OTHER INFORMATION: Oligonucleotide as PCR primer G297_R

<400> SEQUENCE: 151
gatgtcagct gcaccggcaa tcag                                         24

<210> SEQ ID NO 152
<211> LENGTH: 36
<212> TYPE: DNA
<213> ORGANISM: Artificial Sequence
<220> FEATURE:

<223> OTHER INFORMATION: Oligonucleotide as PCR primer G297F_F

<400> SEQUENCE: 152
ggtgcagctg acatcttcct tggctacccg aacggt            36

<210> SEQ ID NO 153
<211> LENGTH: 36
<212> TYPE: DNA
<213> ORGANISM: Artificial Sequence
<220> FEATURE:
<223> OTHER INFORMATION: Oligonucleotide as PCR primer G297L_F

<400> SEQUENCE: 153
ggtgcagctg acatccttct tggctacccg aacggt            36

<210> SEQ ID NO 154
<211> LENGTH: 36
<212> TYPE: DNA
<213> ORGANISM: Artificial Sequence
<220> FEATURE:
<223> OTHER INFORMATION: Oligonucleotide as PCR primer G297W_F

<400> SEQUENCE: 154
ggtgcagctg acatctggct tggctacccg aacggt            36

<210> SEQ ID NO 155
<211> LENGTH: 24
<212> TYPE: DNA
<213> ORGANISM: Artificial Sequence
<220> FEATURE:
<223> OTHER INFORMATION: Oligonucleotide as PCR primer S326_R

<400> SEQUENCE: 155
actggactcg ttcacatagg caac            24

<210> SEQ ID NO 156
<211> LENGTH: 36
<212> TYPE: DNA
<213> ORGANISM: Artificial Sequence
<220> FEATURE:
<223> OTHER INFORMATION: Oligonucleotide as PCR primer S326W_F

<400> SEQUENCE: 156
gtgaacgagt ccagttggct atccaccagc caaaaa            36

<210> SEQ ID NO 157
<211> LENGTH: 24
<212> TYPE: DNA
<213> ORGANISM: Artificial Sequence
<220> FEATURE:
<223> OTHER INFORMATION: Oligonucleotide as PCR primer S330_R

<400> SEQUENCE: 157
ggtggataga gaactggact cgtt            24

<210> SEQ ID NO 158
<211> LENGTH: 36
<212> TYPE: DNA
<213> ORGANISM: Artificial Sequence
<220> FEATURE:
<223> OTHER INFORMATION: Oligonucleotide as PCR primer S330F_F

<400> SEQUENCE: 158
agttctctat ccaccttcca aaagcgacg tactcg            36

```
<210> SEQ ID NO 159
<211> LENGTH: 36
<212> TYPE: DNA
<213> ORGANISM: Artificial Sequence
<220> FEATURE:
<223> OTHER INFORMATION: Oligonucleotide as PCR primer S330M_F

<400> SEQUENCE: 159
agttctctat ccaccatgca aaaagcgacg tactcg                              36

<210> SEQ ID NO 160
<211> LENGTH: 36
<212> TYPE: DNA
<213> ORGANISM: Artificial Sequence
<220> FEATURE:
<223> OTHER INFORMATION: Oligonucleotide as PCR primer S330W_F

<400> SEQUENCE: 160
agttctctat ccacctggca aaaagcgacg tactcg                              36

<210> SEQ ID NO 161
<211> LENGTH: 24
<212> TYPE: DNA
<213> ORGANISM: Artificial Sequence
<220> FEATURE:
<223> OTHER INFORMATION: Oligonucleotide as PCR primer K332_R

<400> SEQUENCE: 161
ttggctggtg gatagagaac tgga                                           24

<210> SEQ ID NO 162
<211> LENGTH: 36
<212> TYPE: DNA
<213> ORGANISM: Artificial Sequence
<220> FEATURE:
<223> OTHER INFORMATION: Oligonucleotide as PCR primer K332G_F

<400> SEQUENCE: 162
ctatccacca gccaaggagc gacgtactcg tttact                              36

<210> SEQ ID NO 163
<211> LENGTH: 36
<212> TYPE: DNA
<213> ORGANISM: Artificial Sequence
<220> FEATURE:
<223> OTHER INFORMATION: Oligonucleotide as PCR primer K332T_F

<400> SEQUENCE: 163
ctatccacca gccaaacagc gacgtactcg tttact                              36

<210> SEQ ID NO 164
<211> LENGTH: 36
<212> TYPE: DNA
<213> ORGANISM: Artificial Sequence
<220> FEATURE:
<223> OTHER INFORMATION: Oligonucleotide as PCR primer K332V_F

<400> SEQUENCE: 164
ctatccacca gccaagtggc gacgtactcg tttact                              36

<210> SEQ ID NO 165
<211> LENGTH: 24
<212> TYPE: DNA
<213> ORGANISM: Artificial Sequence
<220> FEATURE:
<223> OTHER INFORMATION: Oligonucleotide as PCR primer T334_R
```

```
<400> SEQUENCE: 165 cgcttttttgg ctggtggata gaga                                        24

<210> SEQ ID NO 166
<211> LENGTH: 36
<212> TYPE: DNA
<213> ORGANISM: Artificial Sequence
<220> FEATURE:
<223> OTHER INFORMATION: Oligonucleotide as PCR primer T334L_F

<400> SEQUENCE: 166
accagccaaa aagcgcttta ctcgtttact gctact                            36

<210> SEQ ID NO 167
<211> LENGTH: 24
<212> TYPE: DNA
<213> ORGANISM: Artificial Sequence
<220> FEATURE:
<223> OTHER INFORMATION: Oligonucleotide as PCR primer G342_R

<400> SEQUENCE: 167
ggcagtagca gtaaacgagt acgt                                         24

<210> SEQ ID NO 168
<211> LENGTH: 36
<212> TYPE: DNA
<213> ORGANISM: Artificial Sequence
<220> FEATURE:
<223> OTHER INFORMATION: Oligonucleotide as PCR primer G342E_F

<400> SEQUENCE: 168
tttactgcta ctgccgaaaa gcctttgaaa atctcc                            36

<210> SEQ ID NO 169
<211> LENGTH: 36
<212> TYPE: DNA
<213> ORGANISM: Artificial Sequence
<220> FEATURE:
<223> OTHER INFORMATION: Oligonucleotide as PCR primer G342L_F

<400> SEQUENCE: 169
tttactgcta ctgccccttaa gcctttgaaa atctcc                           36

<210> SEQ ID NO 170
<211> LENGTH: 36
<212> TYPE: DNA
<213> ORGANISM: Artificial Sequence
<220> FEATURE:
<223> OTHER INFORMATION: Oligonucleotide as PCR primer G342T_F

<400> SEQUENCE: 170
tttactgcta ctgccacaaa gcctttgaaa atctcc                            36

<210> SEQ ID NO 171
<211> LENGTH: 36
<212> TYPE: DNA
<213> ORGANISM: Artificial Sequence
<220> FEATURE:
<223> OTHER INFORMATION: Oligonucleotide as PCR primer G342W_F

<400> SEQUENCE: 171
tttactgcta ctgcctggaa gcctttgaaa atctcc                            36

<210> SEQ ID NO 172
<211> LENGTH: 24
```

```
<212> TYPE: DNA
<213> ORGANISM: Artificial Sequence
<220> FEATURE:
<223> OTHER INFORMATION: Oligonucleotide as PCR primer K343_R

<400> SEQUENCE: 172
gccggcagta gcagtaaacg agta                                              24

<210> SEQ ID NO 173
<211> LENGTH: 36
<212> TYPE: DNA
<213> ORGANISM: Artificial Sequence
<220> FEATURE:
<223> OTHER INFORMATION: Oligonucleotide as PCR primer K343T_F

<400> SEQUENCE: 173
actgctactg ccggcacacc tttgaaaatc tccctg                                 36

<210> SEQ ID NO 174
<211> LENGTH: 24
<212> TYPE: DNA
<213> ORGANISM: Artificial Sequence
<220> FEATURE:
<223> OTHER INFORMATION: Oligonucleotide as PCR primer S357_R

<400> SEQUENCE: 174
cgcaggggca tcagaccata ccag                                              24

<210> SEQ ID NO 175
<211> LENGTH: 36
<212> TYPE: DNA
<213> ORGANISM: Artificial Sequence
<220> FEATURE:
<223> OTHER INFORMATION: Oligonucleotide as PCR primer S357L_F

<400> SEQUENCE: 175
tctgatgccc ctgcgcttac aactgcttcc gtaacg                                 36

<210> SEQ ID NO 176
<211> LENGTH: 24
<212> TYPE: DNA
<213> ORGANISM: Artificial Sequence
<220> FEATURE:
<223> OTHER INFORMATION: Oligonucleotide as PCR primer T359_R

<400> SEQUENCE: 176
tgtgctcgca ggggcatcag acca                                              24

<210> SEQ ID NO 177
<211> LENGTH: 36
<212> TYPE: DNA
<213> ORGANISM: Artificial Sequence
<220> FEATURE:
<223> OTHER INFORMATION: Oligonucleotide as PCR primer T359F_F

<400> SEQUENCE: 177
gcccctgcga gcacattcgc ttccgtaacg cttgtc                                 36

<210> SEQ ID NO 178
<211> LENGTH: 36
<212> TYPE: DNA
<213> ORGANISM: Artificial Sequence
<220> FEATURE:
<223> OTHER INFORMATION: Oligonucleotide as PCR primer T359G_F

<400> SEQUENCE: 178
``` gccccctgcga gcacaggagc ttccgtaacg cttgtc         36

<210> SEQ ID NO 179
<211> LENGTH: 36
<212> TYPE: DNA
<213> ORGANISM: Artificial Sequence
<220> FEATURE:
<223> OTHER INFORMATION: Oligonucleotide as PCR primer T359I_F

<400> SEQUENCE: 179 gccccctgcga gcacaattgc ttccgtaacg cttgtc         36

<210> SEQ ID NO 180
<211> LENGTH: 36
<212> TYPE: DNA
<213> ORGANISM: Artificial Sequence
<220> FEATURE:
<223> OTHER INFORMATION: Oligonucleotide as PCR primer T359L_F

<400> SEQUENCE: 180 gccccctgcga gcacacttgc ttccgtaacg cttgtc         36

<210> SEQ ID NO 181
<211> LENGTH: 24
<212> TYPE: DNA
<213> ORGANISM: Artificial Sequence
<220> FEATURE:
<223> OTHER INFORMATION: Oligonucleotide as PCR primer S361_R

<400> SEQUENCE: 181
agcagttgtg ctcgcagggg catc                       24

<210> SEQ ID NO 182
<211> LENGTH: 36
<212> TYPE: DNA
<213> ORGANISM: Artificial Sequence
<220> FEATURE:
<223> OTHER INFORMATION: Oligonucleotide as PCR primer S361I_F

<400> SEQUENCE: 182
gcgagcacaa ctgctattgt aacgcttgtc aatgat          36

<210> SEQ ID NO 183
<211> LENGTH: 36
<212> TYPE: DNA
<213> ORGANISM: Artificial Sequence
<220> FEATURE:
<223> OTHER INFORMATION: Oligonucleotide as PCR primer S361V_F

<400> SEQUENCE: 183
gcgagcacaa ctgctgtggt aacgcttgtc aatgat          36

<210> SEQ ID NO 184
<211> LENGTH: 36
<212> TYPE: DNA
<213> ORGANISM: Artificial Sequence
<220> FEATURE:
<223> OTHER INFORMATION: Oligonucleotide as PCR primer S361W_F

<400> SEQUENCE: 184
gcgagcacaa ctgcttgggt aacgcttgtc aatgat          36

<210> SEQ ID NO 185
<211> LENGTH: 24
<212> TYPE: DNA
<213> ORGANISM: Artificial Sequence
<220> FEATURE:
<223> OTHER INFORMATION: Oligonucleotide as PCR primer N376_R

<400> SEQUENCE: 185
tggagcggta atgacaaggt ccag                                          24

<210> SEQ ID NO 186
<211> LENGTH: 36
<212> TYPE: DNA
<213> ORGANISM: Artificial Sequence
<220> FEATURE:
<223> OTHER INFORMATION: Oligonucleotide as PCR primer N376W_F

<400> SEQUENCE: 186
gtcattaccg ctccatgggg cacacagtat gtagga                             36

<210> SEQ ID NO 187
<211> LENGTH: 24
<212> TYPE: DNA
<213> ORGANISM: Artificial Sequence
<220> FEATURE:
<223> OTHER INFORMATION: Oligonucleotide as PCR primer T378_R

<400> SEQUENCE: 187
gccatttgga gcggtaatga caag                                          24

<210> SEQ ID NO 188
<211> LENGTH: 36
<212> TYPE: DNA
<213> ORGANISM: Artificial Sequence
<220> FEATURE:
<223> OTHER INFORMATION: Oligonucleotide as PCR primer T378L_F

<400> SEQUENCE: 188
accgctccaa atggccttca gtatgtagga aatgac                             36

<210> SEQ ID NO 189
<211> LENGTH: 36
<212> TYPE: DNA
<213> ORGANISM: Artificial Sequence
<220> FEATURE:
<223> OTHER INFORMATION: Oligonucleotide as PCR primer T378W_F

<400> SEQUENCE: 189
accgctccaa atggctggca gtatgtagga aatgac                             36

<210> SEQ ID NO 190
<211> LENGTH: 24
<212> TYPE: DNA
<213> ORGANISM: Artificial Sequence
<220> FEATURE:
<223> OTHER INFORMATION: Oligonucleotide as PCR primer F385_R

<400> SEQUENCE: 190
gtcatttcct acatactgtg tgcc                                          24

<210> SEQ ID NO 191
<211> LENGTH: 36
<212> TYPE: DNA
<213> ORGANISM: Artificial Sequence
<220> FEATURE:
<223> OTHER INFORMATION: Oligonucleotide as PCR primer F385M_F

<400> SEQUENCE: 191
tatgtaggaa atgacatgac ttcgccatac aatgat                             36

-continued

<210> SEQ ID NO 192
<211> LENGTH: 36
<212> TYPE: DNA
<213> ORGANISM: Artificial Sequence
<220> FEATURE:
<223> OTHER INFORMATION: Oligonucleotide as PCR primer F385P_F

<400> SEQUENCE: 192
tatgtaggaa atgacccaac ttcgccatac aatgat                              36

<210> SEQ ID NO 193
<211> LENGTH: 36
<212> TYPE: DNA
<213> ORGANISM: Artificial Sequence
<220> FEATURE:
<223> OTHER INFORMATION: Oligonucleotide as PCR primer F385Y_F

<400> SEQUENCE: 193
tatgtaggaa atgactatac ttcgccatac aatgat                              36

<210> SEQ ID NO 194
<211> LENGTH: 24
<212> TYPE: DNA
<213> ORGANISM: Artificial Sequence
<220> FEATURE:
<223> OTHER INFORMATION: Oligonucleotide as PCR primer T386_R

<400> SEQUENCE: 194
aaagtcattt cctacatact gtgt                                           24

<210> SEQ ID NO 195
<211> LENGTH: 36
<212> TYPE: DNA
<213> ORGANISM: Artificial Sequence
<220> FEATURE:
<223> OTHER INFORMATION: Oligonucleotide as PCR primer T386A_F

<400> SEQUENCE: 195
gtaggaaatg actttgcatc gccatacaat gataac                              36

<210> SEQ ID NO 196
<211> LENGTH: 36
<212> TYPE: DNA
<213> ORGANISM: Artificial Sequence
<220> FEATURE:
<223> OTHER INFORMATION: Oligonucleotide as PCR primer T386I_F

<400> SEQUENCE: 196
gtaggaaatg actttatttc gccatacaat gataac                              36

<210> SEQ ID NO 197
<211> LENGTH: 36
<212> TYPE: DNA
<213> ORGANISM: Artificial Sequence
<220> FEATURE:
<223> OTHER INFORMATION: Oligonucleotide as PCR primer T386L_F

<400> SEQUENCE: 197
gtaggaaatg actttctttc gccatacaat gataac                              36

<210> SEQ ID NO 198
<211> LENGTH: 36
<212> TYPE: DNA
<213> ORGANISM: Artificial Sequence
<220> FEATURE:
<223> OTHER INFORMATION: Oligonucleotide as PCR primer T386M_F

```
<400> SEQUENCE: 198
gtaggaaatg actttatgtc gccatacaat gataac                               36

<210> SEQ ID NO 199
<211> LENGTH: 24
<212> TYPE: DNA
<213> ORGANISM: Artificial Sequence
<220> FEATURE:
<223> OTHER INFORMATION: Oligonucleotide as PCR primer S387_R

<400> SEQUENCE: 199
agtaaagtca tttcctacat actg                                            24

<210> SEQ ID NO 200
<211> LENGTH: 36
<212> TYPE: DNA
<213> ORGANISM: Artificial Sequence
<220> FEATURE:
<223> OTHER INFORMATION: Oligonucleotide as PCR primer S387F_F

<400> SEQUENCE: 200
ggaaatgact ttactttccc atacaatgat aactgg                               36

<210> SEQ ID NO 201
<211> LENGTH: 36
<212> TYPE: DNA
<213> ORGANISM: Artificial Sequence
<220> FEATURE:
<223> OTHER INFORMATION: Oligonucleotide as PCR primer S387G_F

<400> SEQUENCE: 201
ggaaatgact ttactggacc atacaatgat aactgg                               36

<210> SEQ ID NO 202
<211> LENGTH: 36
<212> TYPE: DNA
<213> ORGANISM: Artificial Sequence
<220> FEATURE:
<223> OTHER INFORMATION: Oligonucleotide as PCR primer S387I_F

<400> SEQUENCE: 202
ggaaatgact ttactattcc atacaatgat aactgg                               36

<210> SEQ ID NO 203
<211> LENGTH: 36
<212> TYPE: DNA
<213> ORGANISM: Artificial Sequence
<220> FEATURE:
<223> OTHER INFORMATION: Oligonucleotide as PCR primer S387L_F

<400> SEQUENCE: 203
ggaaatgact ttactcttcc atacaatgat aactgg                               36

<210> SEQ ID NO 204
<211> LENGTH: 36
<212> TYPE: DNA
<213> ORGANISM: Artificial Sequence
<220> FEATURE:
<223> OTHER INFORMATION: Oligonucleotide as PCR primer S387M_F

<400> SEQUENCE: 204
ggaaatgact ttactatgcc atacaatgat aactgg                               36

<210> SEQ ID NO 205
```

```
<210> SEQ ID NO 205
<211> LENGTH: 36
<212> TYPE: DNA
<213> ORGANISM: Artificial Sequence
<220> FEATURE:
<223> OTHER INFORMATION: Oligonucleotide as PCR primer S387V_F

<400> SEQUENCE: 205
ggaaatgact ttactgtgcc atacaatgat aactgg                            36

<210> SEQ ID NO 206
<211> LENGTH: 36
<212> TYPE: DNA
<213> ORGANISM: Artificial Sequence
<220> FEATURE:
<223> OTHER INFORMATION: Oligonucleotide as PCR primer S387W_F

<400> SEQUENCE: 206
ggaaatgact ttacttggcc atacaatgat aactgg                            36

<210> SEQ ID NO 207
<211> LENGTH: 24
<212> TYPE: DNA
<213> ORGANISM: Artificial Sequence
<220> FEATURE:
<223> OTHER INFORMATION: Oligonucleotide as PCR primer N390_R

<400> SEQUENCE: 207
gtatggcgaa gtaaagtcat ttcc                                         24

<210> SEQ ID NO 208
<211> LENGTH: 36
<212> TYPE: DNA
<213> ORGANISM: Artificial Sequence
<220> FEATURE:
<223> OTHER INFORMATION: Oligonucleotide as PCR primer N390F_F

<400> SEQUENCE: 208
tttacttcgc catacttcga taactgggat ggccgc                            36

<210> SEQ ID NO 209
<211> LENGTH: 36
<212> TYPE: DNA
<213> ORGANISM: Artificial Sequence
<220> FEATURE:
<223> OTHER INFORMATION: Oligonucleotide as PCR primer N390G_F

<400> SEQUENCE: 209
tttacttcgc catacggaga taactgggat ggccgc                            36

<210> SEQ ID NO 210
<211> LENGTH: 36
<212> TYPE: DNA
<213> ORGANISM: Artificial Sequence
<220> FEATURE:
<223> OTHER INFORMATION: Oligonucleotide as PCR primer N390S_F

<400> SEQUENCE: 210
tttacttcgc catactccga taactgggat ggccgc                            36

<210> SEQ ID NO 211
<211> LENGTH: 36
<212> TYPE: DNA
<213> ORGANISM: Artificial Sequence
<220> FEATURE:
<223> OTHER INFORMATION: Oligonucleotide as PCR primer N390T_F

<400> SEQUENCE: 211
```
tttacttcgc catacacaga taactgggat ggccgc    36

<210> SEQ ID NO 212
<211> LENGTH: 36
<212> TYPE: DNA
<213> ORGANISM: Artificial Sequence
<220> FEATURE:
<223> OTHER INFORMATION: Oligonucleotide as PCR primer N390Y_F

<400> SEQUENCE: 212
tttacttcgc catactatga taactgggat ggccgc    36

<210> SEQ ID NO 213
<211> LENGTH: 24
<212> TYPE: DNA
<213> ORGANISM: Artificial Sequence
<220> FEATURE:
<223> OTHER INFORMATION: Oligonucleotide as PCR primer W393_R

<400> SEQUENCE: 213
gttatcattg tatggcgaag taaa    24

<210> SEQ ID NO 214
<211> LENGTH: 36
<212> TYPE: DNA
<213> ORGANISM: Artificial Sequence
<220> FEATURE:
<223> OTHER INFORMATION: Oligonucleotide as PCR primer W393Q_F

<400> SEQUENCE: 214
ccatacaatg ataaccagga tggccgcaat aacgta    36

<210> SEQ ID NO 215
<211> LENGTH: 24
<212> TYPE: DNA
<213> ORGANISM: Artificial Sequence
<220> FEATURE:
<223> OTHER INFORMATION: Oligonucleotide as PCR primer R396_R

<400> SEQUENCE: 215
gccatcccag ttatcattgt atgg    24

<210> SEQ ID NO 216
<211> LENGTH: 36
<212> TYPE: DNA
<213> ORGANISM: Artificial Sequence
<220> FEATURE:
<223> OTHER INFORMATION: Oligonucleotide as PCR primer R396G_F

<400> SEQUENCE: 216
gataactggg atggcggaaa taacgtagaa aatgta    36

<210> SEQ ID NO 217
<211> LENGTH: 24
<212> TYPE: DNA
<213> ORGANISM: Artificial Sequence
<220> FEATURE:
<223> OTHER INFORMATION: Oligonucleotide as PCR primer F403_R

<400> SEQUENCE: 217
tacattttct acgttattgc ggcc    24

<210> SEQ ID NO 218
<211> LENGTH: 36
<212> TYPE: DNA

```
<213> ORGANISM: Artificial Sequence
<220> FEATURE:
<223> OTHER INFORMATION: Oligonucleotide as PCR primer F403K_F

<400> SEQUENCE: 218
aacgtagaaa atgtaaaaat taatgcacca caaagc                          36

<210> SEQ ID NO 219
<211> LENGTH: 36
<212> TYPE: DNA
<213> ORGANISM: Artificial Sequence
<220> FEATURE:
<223> OTHER INFORMATION: Oligonucleotide as PCR primer F403T_F

<400> SEQUENCE: 219
aacgtagaaa atgtaacaat taatgcacca caaagc                          36

<210> SEQ ID NO 220
<211> LENGTH: 36
<212> TYPE: DNA
<213> ORGANISM: Artificial Sequence
<220> FEATURE:
<223> OTHER INFORMATION: Oligonucleotide as PCR primer N405F_F

<400> SEQUENCE: 220
gaaaatgtat ttattttcgc accacaaagc gggacg                          36

<210> SEQ ID NO 221
<211> LENGTH: 36
<212> TYPE: DNA
<213> ORGANISM: Artificial Sequence
<220> FEATURE:
<223> OTHER INFORMATION: Oligonucleotide as PCR primer N405I_F

<400> SEQUENCE: 221
gaaaatgtat ttattattgc accacaaagc gggacg                          36

<210> SEQ ID NO 222
<211> LENGTH: 36
<212> TYPE: DNA
<213> ORGANISM: Artificial Sequence
<220> FEATURE:
<223> OTHER INFORMATION: Oligonucleotide as PCR primer N405L_F

<400> SEQUENCE: 222
gaaaatgtat ttattcttgc accacaaagc gggacg                          36

<210> SEQ ID NO 223
<211> LENGTH: 36
<212> TYPE: DNA
<213> ORGANISM: Artificial Sequence
<220> FEATURE:
<223> OTHER INFORMATION: Oligonucleotide as PCR primer N405P_F

<400> SEQUENCE: 223
gaaaatgtat ttattccagc accacaaagc gggacg                          36

<210> SEQ ID NO 224
<211> LENGTH: 36
<212> TYPE: DNA
<213> ORGANISM: Artificial Sequence
<220> FEATURE:
<223> OTHER INFORMATION: Oligonucleotide as PCR primer N405V_F

<400> SEQUENCE: 224
gaaaatgtat ttattgtggc accacaaagc gggacg                          36
```

```
<210> SEQ ID NO 225
<211> LENGTH: 36
<212> TYPE: DNA
<213> ORGANISM: Artificial Sequence
<220> FEATURE:
<223> OTHER INFORMATION: Oligonucleotide as PCR primer N405W_F

<400> SEQUENCE: 225
gaaaatgtat ttatttgggc accacaaagc gggacg                              36

<210> SEQ ID NO 226
<211> LENGTH: 24
<212> TYPE: DNA
<213> ORGANISM: Artificial Sequence
<220> FEATURE:
<223> OTHER INFORMATION: Oligonucleotide as PCR primer A406_R

<400> SEQUENCE: 226
attaataaat acattttcta cgtt                                           24

<210> SEQ ID NO 227
<211> LENGTH: 36
<212> TYPE: DNA
<213> ORGANISM: Artificial Sequence
<220> FEATURE:
<223> OTHER INFORMATION: Oligonucleotide as PCR primer A406F_F

<400> SEQUENCE: 227
aatgtattta ttaatttccc acaaagcggg acgtat                              36

<210> SEQ ID NO 228
<211> LENGTH: 36
<212> TYPE: DNA
<213> ORGANISM: Artificial Sequence
<220> FEATURE:
<223> OTHER INFORMATION: Oligonucleotide as PCR primer A406V_F

<400> SEQUENCE: 228
aatgtattta ttaatgtgcc acaaagcggg acgtat                              36

<210> SEQ ID NO 229
<211> LENGTH: 36
<212> TYPE: DNA
<213> ORGANISM: Artificial Sequence
<220> FEATURE:
<223> OTHER INFORMATION: Oligonucleotide as PCR primer A406W_F

<400> SEQUENCE: 229
aatgtattta ttaattggcc acaaagcggg acgtat                              36

<210> SEQ ID NO 230
<211> LENGTH: 24
<212> TYPE: DNA
<213> ORGANISM: Artificial Sequence
<220> FEATURE:
<223> OTHER INFORMATION: Oligonucleotide as PCR primer P407_R

<400> SEQUENCE: 230
tgcattaata aatacatttt ctac                                           24

<210> SEQ ID NO 231
<211> LENGTH: 36
<212> TYPE: DNA
<213> ORGANISM: Artificial Sequence
<220> FEATURE:
```

-continued

<223> OTHER INFORMATION: Oligonucleotide as PCR primer P407C_F

<400> SEQUENCE: 231
gtatttatta atgcatgcca aagcgggacg tataca                              36

<210> SEQ ID NO 232
<211> LENGTH: 36
<212> TYPE: DNA
<213> ORGANISM: Artificial Sequence
<220> FEATURE:
<223> OTHER INFORMATION: Oligonucleotide as PCR primer P407G_F

<400> SEQUENCE: 232
gtatttatta atgcaggaca aagcgggacg tataca                              36

<210> SEQ ID NO 233
<211> LENGTH: 24
<212> TYPE: DNA
<213> ORGANISM: Artificial Sequence
<220> FEATURE:
<223> OTHER INFORMATION: Oligonucleotide as PCR primer Q408_R

<400> SEQUENCE: 233
tggtgcatta ataaatacat tttc                                           24

<210> SEQ ID NO 234
<211> LENGTH: 36
<212> TYPE: DNA
<213> ORGANISM: Artificial Sequence
<220> FEATURE:
<223> OTHER INFORMATION: Oligonucleotide as PCR primer Q408I_F

<400> SEQUENCE: 234
tttattaatg caccaattag cgggacgtat acaatt                              36

<210> SEQ ID NO 235
<211> LENGTH: 36
<212> TYPE: DNA
<213> ORGANISM: Artificial Sequence
<220> FEATURE:
<223> OTHER INFORMATION: Oligonucleotide as PCR primer Q408N_F

<400> SEQUENCE: 235
tttattaatg caccaaatag cgggacgtat acaatt                              36

<210> SEQ ID NO 236
<211> LENGTH: 36
<212> TYPE: DNA
<213> ORGANISM: Artificial Sequence
<220> FEATURE:
<223> OTHER INFORMATION: Oligonucleotide as PCR primer Q408W_F

<400> SEQUENCE: 236
tttattaatg caccatggag cgggacgtat acaatt                              36

<210> SEQ ID NO 237
<211> LENGTH: 36
<212> TYPE: DNA
<213> ORGANISM: Artificial Sequence
<220> FEATURE:
<223> OTHER INFORMATION: Oligonucleotide as PCR primer Q408Y_F

<400> SEQUENCE: 237
tttattaatg caccatatag cgggacgtat acaatt                              36

-continued

```
<210> SEQ ID NO 238
<211> LENGTH: 36
<212> TYPE: DNA
<213> ORGANISM: Artificial Sequence
<220> FEATURE:
<223> OTHER INFORMATION: Oligonucleotide as PCR primer S409W_F

<400> SEQUENCE: 238
attaatgcac cacaatgggg gacgtataca attgag                                    36

<210> SEQ ID NO 239
<211> LENGTH: 24
<212> TYPE: DNA
<213> ORGANISM: Artificial Sequence
<220> FEATURE:
<223> OTHER INFORMATION: Oligonucleotide as PCR primer S409_R

<400> SEQUENCE: 239
ttgtggtgca ttaataaata catt                                                 24

<210> SEQ ID NO 240
<211> LENGTH: 36
<212> TYPE: DNA
<213> ORGANISM: Artificial Sequence
<220> FEATURE:
<223> OTHER INFORMATION: Oligonucleotide as PCR primer S409Y_F

<400> SEQUENCE: 240
attaatgcac cacaatatgg gacgtataca attgag                                    36

<210> SEQ ID NO 241
<211> LENGTH: 24
<212> TYPE: DNA
<213> ORGANISM: Artificial Sequence
<220> FEATURE:
<223> OTHER INFORMATION: Oligonucleotide as PCR primer T411_R

<400> SEQUENCE: 241
cccgctttgt ggtgcattaa taaa                                                 24

<210> SEQ ID NO 242
<211> LENGTH: 36
<212> TYPE: DNA
<213> ORGANISM: Artificial Sequence
<220> FEATURE:
<223> OTHER INFORMATION: Oligonucleotide as PCR primer T411A_F

<400> SEQUENCE: 242
gcaccacaaa gcggggcata tacaattgag gtacag                                    36

<210> SEQ ID NO 243
<211> LENGTH: 36
<212> TYPE: DNA
<213> ORGANISM: Artificial Sequence
<220> FEATURE:
<223> OTHER INFORMATION: Oligonucleotide as PCR primer T411L_F

<400> SEQUENCE: 243
gcaccacaaa gcgggcttta tacaattgag gtacag                                    36

<210> SEQ ID NO 244
<211> LENGTH: 36
<212> TYPE: DNA
<213> ORGANISM: Artificial Sequence
<220> FEATURE:
<223> OTHER INFORMATION: Oligonucleotide as PCR primer T411P_F
```

<400> SEQUENCE: 244
gcaccacaaa gcgggccata tacaattgag gtacag                                    36

<210> SEQ ID NO 245
<211> LENGTH: 36
<212> TYPE: DNA
<213> ORGANISM: Artificial Sequence
<220> FEATURE:
<223> OTHER INFORMATION: Oligonucleotide as PCR primer T411V_F

<400> SEQUENCE: 245
gcaccacaaa gcggggtgta tacaattgag gtacag                                    36

<210> SEQ ID NO 246
<211> LENGTH: 24
<212> TYPE: DNA
<213> ORGANISM: Artificial Sequence
<220> FEATURE:
<223> OTHER INFORMATION: Oligonucleotide as PCR primer T427_R

<400> SEQUENCE: 246
ctgtggtcca accggtacgt tata                                                 24

<210> SEQ ID NO 247
<211> LENGTH: 36
<212> TYPE: DNA
<213> ORGANISM: Artificial Sequence
<220> FEATURE:
<223> OTHER INFORMATION: Oligonucleotide as PCR primer T427V_F

<400> SEQUENCE: 247
ccggttggac cacaggtgtt ctcgttggca attgtg                                    36

<210> SEQ ID NO 248
<211> LENGTH: 24
<212> TYPE: DNA
<213> ORGANISM: Artificial Sequence
<220> FEATURE:
<223> OTHER INFORMATION: Oligonucleotide as PCR primer V433_R

<400> SEQUENCE: 248
aattgccaac gagaaggtct gtgg                                                 24

<210> SEQ ID NO 249
<211> LENGTH: 36
<212> TYPE: DNA
<213> ORGANISM: Artificial Sequence
<220> FEATURE:
<223> OTHER INFORMATION: Oligonucleotide as PCR primer V433L_F

<400> SEQUENCE: 249
ttctcgttgg caattcttaa ttaatagaat aacaga                                    36

<210> SEQ ID NO 250
<211> LENGTH: 435
<212> TYPE: PRT
<213> ORGANISM: Bacillus sp. modified KSM-KP43

<400> SEQUENCE: 250

Asn Asp Val Ala Arg Gly Ile Val Lys Ala Asp Val Ala Gln Ser Ser
 1               5                  10                  15

Tyr Gly Leu Tyr Gly Gln Gly Gln Ile Val Ala Val Ala Asp Thr Gly
             20                  25                  30

Leu Asp Thr Gly Arg Asn Asp Ser Ser Met His Glu Ala Phe Arg Gly

```
            35                  40                  45
Lys Ile Thr Ala Leu Tyr Ala Leu Gly Arg Thr Asn Ala Asn Asp
 50                  55                  60

Pro Asn Gly His Gly Thr His Val Ala Gly Ser Val Leu Gly Asn Gly
 65                  70                  75                  80

Ser Thr Asn Lys Gly Met Ala Pro Gln Ala Asn Leu Val Phe Gln Ser
                 85                  90                  95

Ile Met Asp Ser Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ser Ser Thr Asn Gly Ala Tyr Thr Thr Asp Ser Arg
        130                 135                 140

Asn Val Asp Asp Tyr Val Arg Lys Asn Asp Met Thr Ile Leu Phe Ala
145                 150                 155                 160

Ala Gly Asn Glu Gly Pro Gly Val Gly Thr Ile Ser Ala Pro Gly Thr
                165                 170                 175

Ala Lys Asn Ala Ile Thr Val Gly Ala Thr Glu Asn Leu Arg Pro Ser
            180                 185                 190

Phe Gly Ser Gln Ala Asp Asn Ile Asn His Val Ala Gln Phe Ser Ser
        195                 200                 205

Arg Gly Pro Thr Lys Asp Gly Arg Ile Lys Pro Asp Val Met Ala Pro
210                 215                 220

Gly Thr Phe Ile Leu Ser Ala Arg Ser Ser Leu Ala Pro Asp Ser Ser
225                 230                 235                 240

Phe Trp Ala Asn His Asp Ser Lys Tyr Ala Tyr Met Gly Gly Thr Ser
                245                 250                 255

Met Ile Thr Pro Ile Val Ala Gly Asn Val Ala Gln Leu Arg Glu His
            260                 265                 270

Phe Ile Lys Asn Arg Gly Ile Thr Pro Lys Pro Ser Leu Leu Lys Ala
        275                 280                 285

Ala Leu Ile Ala Gly Ala Ala Asp Ile Gly Leu Gly Tyr Pro Asn Gly
290                 295                 300

Asn Gln Gly Trp Gly Arg Val Thr Leu Asp Lys Ser Leu Asn Val Ala
305                 310                 315                 320

Tyr Val Asn Glu Ser Ser Leu Ser Thr Ser Gln Lys Ala Thr Tyr
                325                 330                 335

Ser Phe Thr Ala Thr Ala Gly Lys Pro Leu Lys Ile Ser Leu Val Trp
            340                 345                 350

Ser Asp Ala Pro Ala Ser Thr Ser Ala Ser Val Thr Leu Val Asn Asp
        355                 360                 365

Leu Asn Leu Val Ile Thr Ala Pro Asn Gly Thr Gln Tyr Val Gly Asn
        370                 375                 380

Asp Phe Thr Ala Pro Tyr Asn Asp Asn Trp Asp Gly Arg Asn Asn Val
385                 390                 395                 400

Glu Asn Val Phe Ile Asn Ala Pro Gln Ser Gly Thr Tyr Thr Ile Glu
                405                 410                 415

Val Gln Ala Tyr Asn Val Pro Val Gly Pro Gln Thr Phe Ser Leu Ala
            420                 425                 430

Ile Val Asn
        435

<210> SEQ ID NO 251
```

```
<211> LENGTH: 32
<212> TYPE: DNA
<213> ORGANISM: Artificial Sequence
<220> FEATURE:
<223> OTHER INFORMATION: Oligonucleotide as PCR primer pHY+1(HindIII)F

<400> SEQUENCE: 251
ggggaagctt ctagagatct gcaggtcgac gg                                  32

<210> SEQ ID NO 252
<211> LENGTH: 41
<212> TYPE: DNA
<213> ORGANISM: Artificial Sequence
<220> FEATURE:
<223> OTHER INFORMATION: Oligonucleotide as PCR primer
      pHY+3040(HindIII)R

<400> SEQUENCE: 252
ggggaagctt aaggtaaagg ataaaacagc acaattccaa g                        41

<210> SEQ ID NO 253
<211> LENGTH: 36
<212> TYPE: DNA
<213> ORGANISM: Artificial Sequence
<220> FEATURE:
<223> OTHER INFORMATION: Oligonucleotide as PCR primer SP64-F(EcoRI)

<400> SEQUENCE: 253
gggggaattc gaacaagtac ttaccatttt agagtc                              36

<210> SEQ ID NO 254
<211> LENGTH: 36
<212> TYPE: DNA
<213> ORGANISM: Artificial Sequence
<220> FEATURE:
<223> OTHER INFORMATION: Oligonucleotide as PCR primer SP64-R(BamHI)

<400> SEQUENCE: 254
ggggggatcc ttattaaagt aattgaatca aatagc                              36

<210> SEQ ID NO 255
<211> LENGTH: 3636
<212> TYPE: DNA
<213> ORGANISM: Artificial Sequence
<220> FEATURE:
<223> OTHER INFORMATION: Oligonucleotide vector pHA3040SP64

<400> SEQUENCE: 255
aagcttctag agatctgcag gtcgacggat ccttattaaa gtaattgaat caaatagcta    60
aattcataag cataaccgaa agtgctttcg ataatgtttt aaaaaacttg tgagtaaccc   120
agattctctc ctgcttctca acaacttata agttatctaa attatgacta cttgactcaa   180 tctacccccct tcctaaatcg gcatatagca caaggttaac cgcttacaaa tatcataaaa   240
aaaagatgta tattgcgtct tacaaattta ttatagcatg ttgaaattag aatactagag   300
tgaattttca ccccctgttt aaaaaagag ccggaatata aggttttata gtaaaccgct   360
ttcgaaacag tattttcgtt ctaggtataa ataattatag aaaagcgttt tctataatta   420
aaactaatac aattttctta tgtccgttgt cttctacttc tatttcaatc tttagttctc   480
aaaaaaattc aaaaaaataa aatcaggacc tgtttacctg attttattcc gtattcaatt   540 taaaagaaa ttccctctaa atataagccg gttgcatcgg caaatcctgc ttggcttcta   600 tctttttgact ctaaaatggt aagtacttgt tcgaattcct gttataaaaa aaggatcaat   660
```

```
tttgaactct ctcccaaagt tgatcccctta acgatttaga aatccctttg agaatgttta    720
tatacattca aggtaaccag ccaactaatg acaatgattc ctgaaaaaag taataacaaa    780
ttactataca gataagttga ctgatcaact tccataggta acaacctttg atcaagtaag    840
ggtatggata taaaccacc tacaattgca atacctgttc cctctgataa aaagctggta    900
aagttaagca aactcattcc agcaccagct tcctgctgtt tcaagctact tgaaacaatt    960
gttgatataa ctgttttggt gaacgaaagc ccacctaaaa caaatacgat tataattgtc   1020
atgaaccatg atgttgtttc taaaagaaag gaagcagtta aaaagctaac agaaagaaat   1080
gtaactccga tgtttaacac gtataaagga cctcttctat caacaagtat cccaccaatg   1140
tagccgaaaa taatgacact cattgttcca gggaaaataa ttacacttcc gatttcggca   1200
gtacttagct ggtgaacatc tttcatcata taaggaacca tagagacaaa ccctgctact   1260
gttccaaata taattccccc acaaagaact ccaatcataa aaggtatatt tttcccctaat   1320
ccgggatcaa caaaaggatc tgttactttc ctgatatgtt ttacaaatat caggaatgac   1380
agcacgctaa cgataagaaa agaaatgcta tatgatgttg taaacaacat aaaaaataca   1440
atgcctacag acattagtat aattcctttg atatcaaaat gacctttttat ccttacttct   1500
ttctttaata atttcataag aaacggaaca gtgataattg ttatcatagg aatgagtaga   1560
agataggacc aatgaatata atgggctatc attccaccaa tcgctggacc gactccttct   1620
cccatggcta ctatcgatcc aataagacca atgctttac ccctattttc ctttggaata   1680
tagcgcgcaa ctacaaccat tacgagtgct ggaaatgcag ctgcaccagc cccttgaata   1740
aaacgagcca taataagtaa ggaaaagaaa gaatggccaa caaacccaat taccgacccg   1800
aaacaattta ttataattcc aaataggagt aaccttttga tgcctaattg atcagatagc   1860
tttccatata cagctgttcc aatggaaaag gttaacataa aggctgtgtt cacccagttt   1920
gtactcgcag gtggtttatt aaaatcattt gcaatatcag gtaatgagac gttcaaaacc   1980
atttcattta atacgctaaa aaaagataaa atgcaaagcc aaattaaaat ttggttgtgt   2040
cgtaaattcg attgtgaata ggatgtattc acatttcacc ctccaataat gagggcagac   2100
gtagtttata gggttaatga tacgcttccc tcttttaatt gaaccctgtt acattcatta   2160
ttcattacac ttcataatta attcctccta aacttgatta aaacatttta ccacatataa   2220
actaagtttt aaattcagta tttcatcact tatacaacaa tatggcccgt ttgttgaact   2280
actctttaat aaaataattt ttccgttccc aattccacat tgcaataata gaaaatccat   2340
cttcatcggc ttttttcgtca tcatctgtat gaatcaaatc gccttcttct gtgtcatcaa   2400
ggtttaattt tttatgtatt tcttttaaca aaccaccata ggagattaac cttttacggt   2460
gtaaaccttc ctccaaatca gacaaacgtt tcaaattctt ttcttcatca tcggtcataa   2520
aatccgtatc ctttacagga tatttgtcag tttcgtcaat tgccgattgt atatccgatt   2580
tatatttatt tttcggtcga atcatttgaa cttttacatt tggatcatag tctaatttca   2640
ttgccttttt ccaaaattga atccattgtt tttgattcac gtagttttct gtattcttaa   2700
aataagttgg ttccacacat accaatacat gcatgtgctg attataagaa ttatctttat   2760
tatttattgt cacttccgtt gcacgcataa aaccaacaag attttttatta attttttttat   2820
attgcatcat tcggcgaaat ccttgagcca tatctgacaa actcttattt aattcttcgc   2880
catcataaac attttttaact gttaatgtga gaaacaacca acgaactgtt ggcttttgtt   2940
taataacttc agcaacaacc ttttgtgact gaatgccatg tttcattgct ctcctccagt   3000
tgcacattgg acaaagcctg gatttacaaa accacactcg atacaacttt ctttcgcctg   3060
```

```
tttcacgatt ttgtttatac tctaatattt cagcacaatc ttttactctt tcagcctttt    3120
taaattcaag aatatgcaga agttcaaagt aatcaacatt agcgattttc ttttctctcc    3180
atggtctcac ttttccactt tttgtcttgt ccactaaaac ccttgatttt tcatctgaat    3240
aaatgctact attaggacac ataatattaa aagaaacccc catctattta gttatttgtt    3300
tggtcactta taactttaac agatggggtt tttctgtgca accaatttta agggttttcc    3360
aatactttaa aacacataca taccaacact tcaacgcacc tttcagcaac taaaataaaa    3420
atgacgttat ttctatatgt atcaagataa gaaagaacaa gttcaaaacc atcaaaaaaa    3480 gacaccttt  caggtgcttt ttttatttta taaactcatt ccctgatctc gacttcgttc    3540 ttttttacc  tctcggttat gagttagttc aaattcgttc tttttaggtt ctaaatcgtg    3600 ttttcttgg  aattgtgctg ttttatcctt tacctt                              3636
```